(12) United States Patent
Kimura

(10) Patent No.: US 7,187,446 B2
(45) Date of Patent: Mar. 6, 2007

(54) MEASURING APPARATUS

(75) Inventor: Toshihito Kimura, Kanagawa-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 394 days.

(21) Appl. No.: 10/898,566

(22) Filed: Jul. 26, 2004

(65) Prior Publication Data

US 2006/0017931 A1   Jan. 26, 2006

(51) Int. Cl.
  *G01N 21/55* (2006.01)
(52) U.S. Cl. ................. 356/445; 250/572; 250/573
(58) Field of Classification Search ........ 356/445–448; 250/573
  See application file for complete search history.

(56) References Cited

U.S. PATENT DOCUMENTS

| 4,889,427 | A | * | 12/1989 | Van Veen et al. | 356/445 |
|---|---|---|---|---|---|
| 5,055,265 | A | * | 10/1991 | Finlan | 422/82.05 |
| 5,255,075 | A | * | 10/1993 | Cush | 356/445 |
| 5,341,215 | A | * | 8/1994 | Seher | 356/445 |
| 5,485,277 | A | * | 1/1996 | Foster | 356/445 |
| 5,991,048 | A | * | 11/1999 | Karlson et al. | 356/445 |
| 6,417,925 | B1 | * | 7/2002 | Naya | 356/445 |
| 6,570,657 | B1 | * | 5/2003 | Hoppe et al. | 356/445 |
| 6,597,456 | B2 | * | 7/2003 | Kubo et al. | 356/445 |
| 6,597,721 | B1 | * | 7/2003 | Hutchinson et al. | 372/98 |
| 6,667,807 | B2 | * | 12/2003 | Lieberman | 356/445 |
| 6,741,352 | B2 | * | 5/2004 | Naya | 356/445 |
| 6,891,620 | B2 | * | 5/2005 | Mukai et al. | 356/445 |
| 7,030,988 | B2 | * | 4/2006 | Kubo et al. | 356/445 |
| 7,075,657 | B2 | * | 7/2006 | Sato | 356/455 |
| 2003/0075697 | A1 | * | 4/2003 | Ohtsuka et al. | 250/573 |

FOREIGN PATENT DOCUMENTS

JP         6-167443 A     6/1994

OTHER PUBLICATIONS

"Surface Refracto-sensor using Evanescent Waves: Principles and Instrumentations" by Takayuki Okamoto (Spectrum Researches, vol. 47, No. 1 (1998), pp. 21 to 23 & pp. 26 and 27).
"Porous Gold in Surface Plasmon Resonance Measurement" by D.V. Noort, K. Johansen, and C.F. Mandenius (EUROSENSORS XIII, 1999, pp. 585-588).
Surface Plasmon Resonance Interferometry for Micro-Array Biosensing by P.I. Nikitin, A.N. Grigorenko, A.A. Beloglazov, M.V. Valeiko, A.I. Savchuk, and O.A. Savchuk (EUROSENSORS XIII, 1999, pp. 235-238).

* cited by examiner

*Primary Examiner*—Layla G. Lauchman
*Assistant Examiner*—Jarreas Underwood
(74) *Attorney, Agent, or Firm*—Sughrue Mion, PLLC

(57) ABSTRACT

A measuring apparatus includes a sensor well unit having a plurality of sample wells, which are formed in a dielectric block and a thin film layer provided on the inner bottom surface of each sample well. A light beam projector causes a plurality of light beams to impinge upon the interfaces of the inner bottom surfaces of one-dimensionally arranged sample wells out of the plurality of sample wells and the thin film layers at various angles of incidence so that total internal reflection conditions are satisfied at each of the interfaces, and the light beams reflected at the respective interfaces are received by a photodetector. A longitudinal tilt measuring system measures a longitudinal tilt of the interface from a predetermined reference position, and a corrected measured value corrected according to the longitudinal tilt measured by the longitudinal tilt measuring system is obtained.

32 Claims, 36 Drawing Sheets

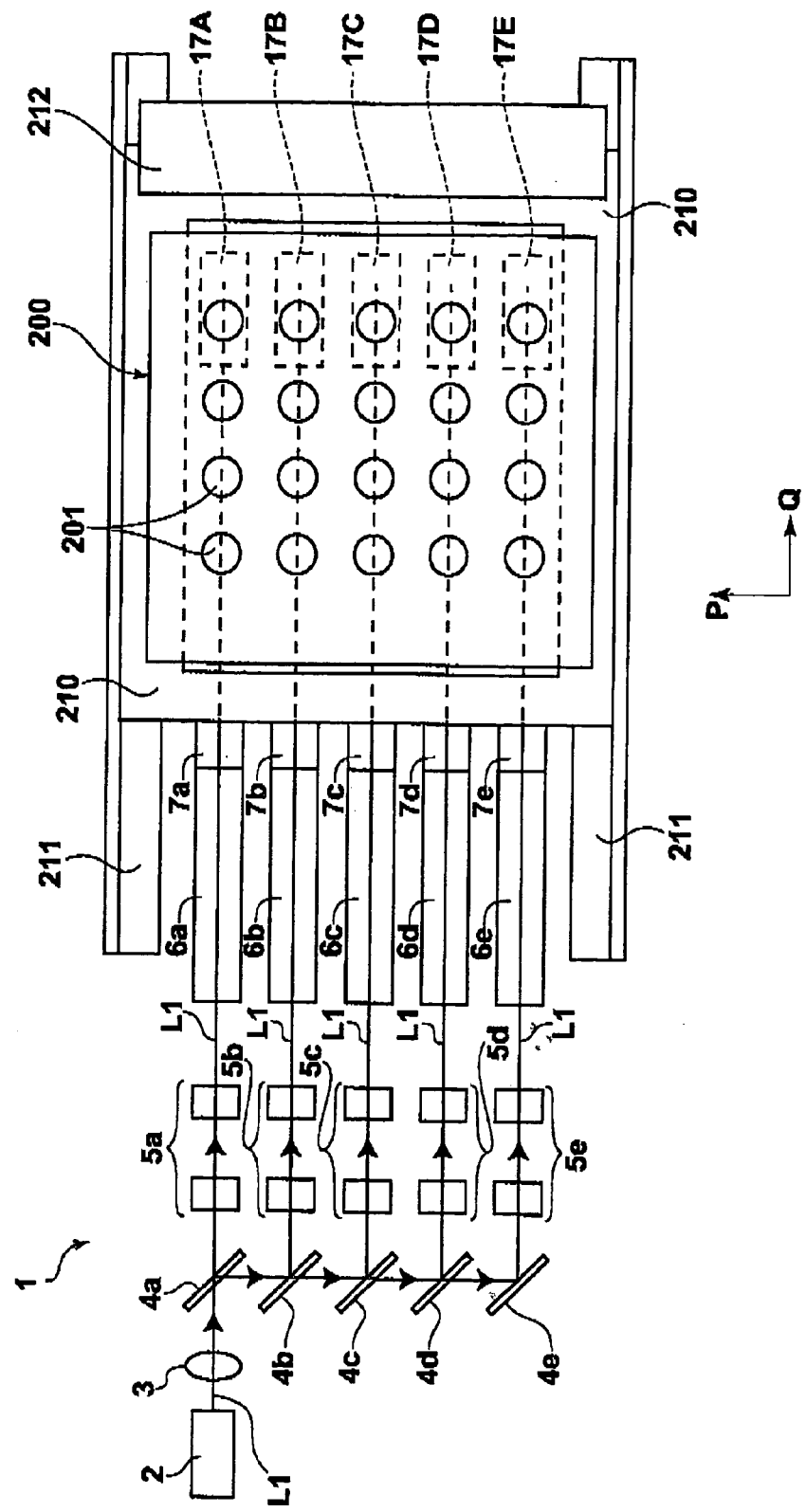

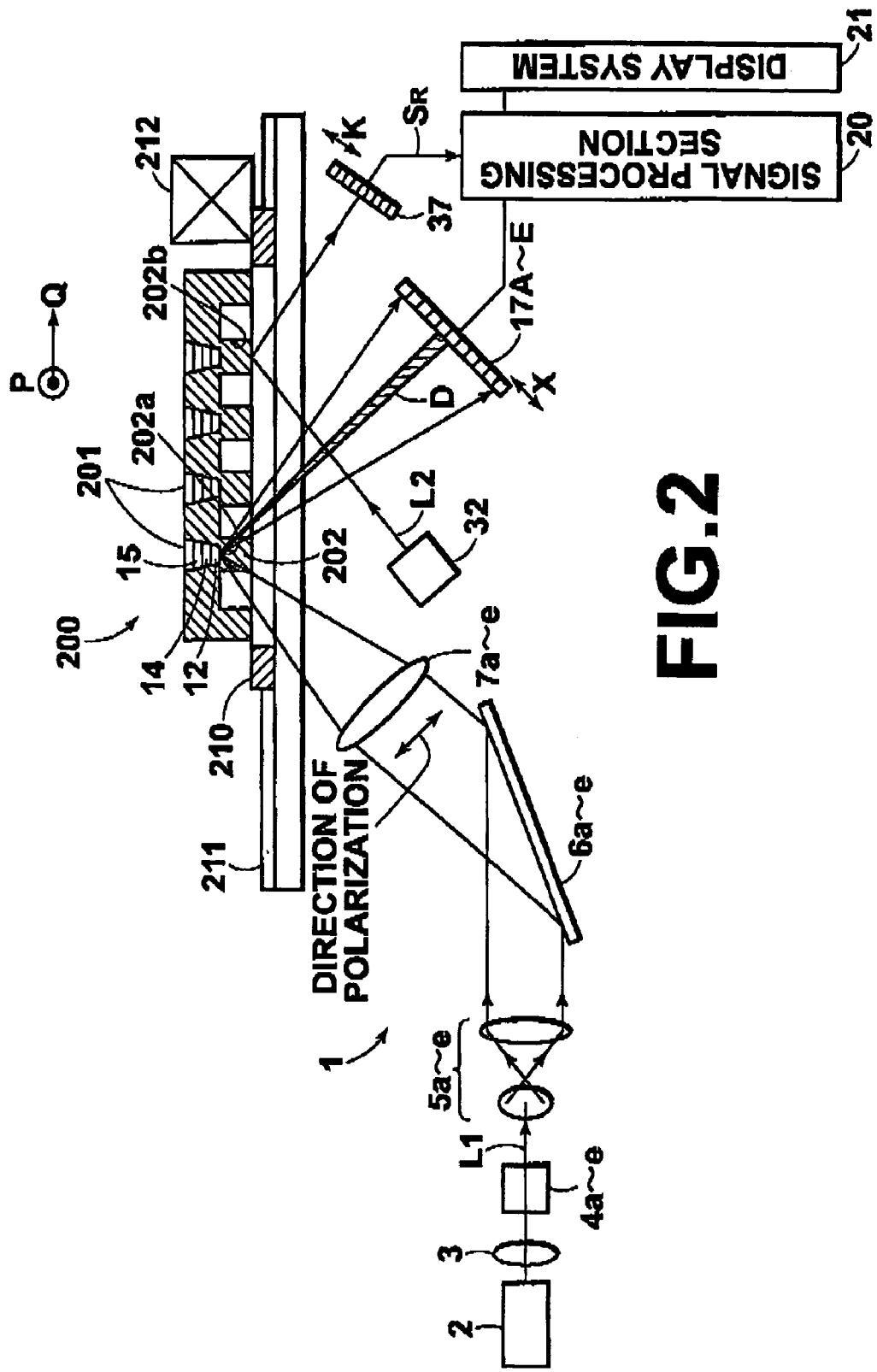

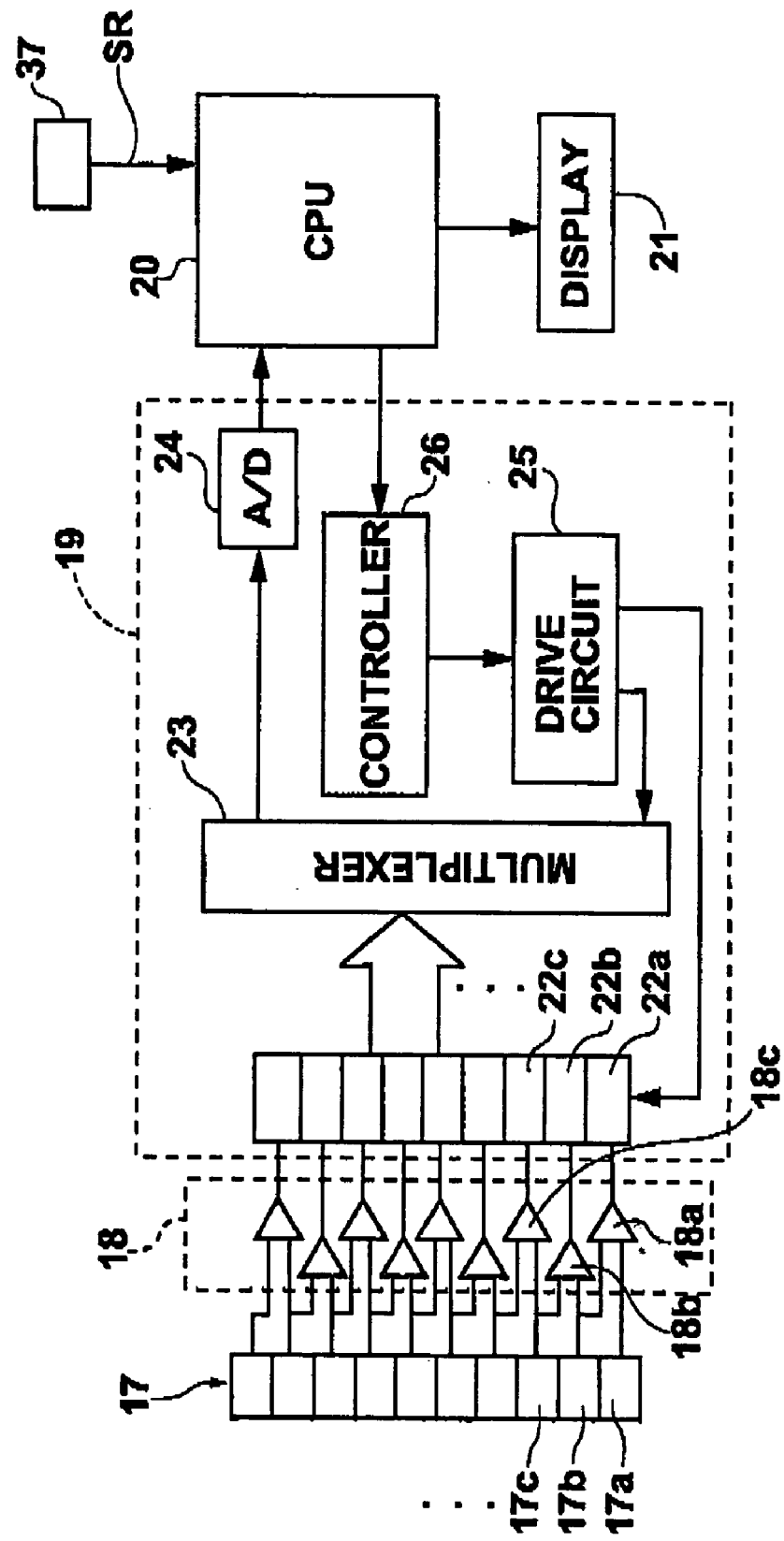

MEASURING APPARATUS

BACKGROUND OF THE INVENTION

1. Field of the Invention

This invention relates to a measuring apparatus such as a surface plasmon resonance sensor for quantitatively analyzing a material in a sample on the basis of generation of surface plasmon, and more particularly to a measuring apparatus in which a light beam is caused to reflect in total reflection at the interface between metal film or a clad layer in contact with a sample and a dielectric body to generate evanescent waves and the sample is analyzed on the basis of change in intensity of the light beam reflected in total reflection.

2. Description of the Related Art

In metal, free electrons vibrate in a group to generate compression waves called plasma waves. The compression waves generated in a metal surface are quantized into surface plasmon.

There have been proposed various surface plasmon resonance sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The surface plasmon resonance sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block at various angles of incidence so that total internal reflection conditions are satisfied at the interface of the dielectric block and the metal film and various angles of incidence of the light beam to the interface of the dielectric block and the metal film including an angle of incidence at which attenuation in total internal reflection is generated due to surface plasmon resonance can be obtained, and a photodetector means which detects the intensity of the light beam reflected in total internal reflection at the interface and detects a state of surface plasmon resonance, i.e., a state of attenuation in total internal reflection.

In order to obtain various angles of incidence of the light beam to the interface, a relatively thin incident light beam may be caused to impinge upon the interface changing the angle of incidence or a relatively thick incident light beam may be caused to impinge upon the interface in the form of convergent light or divergent light so that the incident light beam includes components impinging upon the interface at various angles. In the former case, the light beam which is reflected from the interface at an angle which varies as the angle of incidence changes may be detected by a photodetector which is moved in synchronization with the change of the angle of incidence or by an area sensor extending in the direction in which reflected light beam is moved as the angle of incidence changes. In the latter case, an area sensor which extends in directions so that all the components of light reflected from the interface at various angles can be detected by the area sensor may be used.

In such a surface plasmon resonance sensor, when a light beam impinges upon the metal film at a particular angle of incidence θsp not smaller than the angle of total internal reflection, evanescent waves having an electric field distribution in the sample in contact with the metal film are generated and surface plasmon is excited in the interface between the metal film and the sample. When the wave vector of the evanescent light is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the surface plasmon sensor so that the light beam impinges upon the interface in the form of p-polarized light or p-polarized components are only detected.

When the wave number of the surface plasmon can be known from the angle of incidence θsp at which the phenomenon of attenuation in total internal reflection (ATR) takes place, the dielectric constant of the sample can be obtained. That is $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, ω represents the angular frequency of the surface plasmon, c represents the speed of light in a vacuum, and ⊂m and ∈s respectively represent the dielectric constants of the metal and the sample.

When the dielectric constant ∈s of the sample is known, the concentration of a specific material in the sample can be determined on the basis of a predetermined calibration curve or the like. Accordingly, a property related to the dielectric constant (refractive index) of the sample can be detected by detecting the angle of incidence θsp at which the intensity of light reflected in total internal reflection from the interface of the prism and the metal film sharply drops (this angel θsp will be referred to as "the attenuation angle θsp", hereinbelow).

As a similar apparatus utilizing the phenomenon of attenuation in total internal reflection (ATR), there has been known a leaky mode sensor described in, for instance, "Surface Refracto-sensor using Evanescent Waves: Principles and Instrumentations" by Takayuki Okamoto (Spectrum Researches, Vol. 47, No. 1 (1998), pp. 21 to 23 & pp. 26 and 27). The leaky mode sensor basically comprises a dielectric block shaped, for instance, like a prism, a clad layer which is formed on one face of the dielectric block, an optical waveguide layer which is formed on the clad layer and is brought into contact with a sample, a light source emitting a light beam, an optical system which causes the light beam to enter the dielectric block at various angles of incidence so that total internal reflection conditions are satisfied at the interface of the dielectric block and the clad layer and various angles of incidence of the light beam to the interface of the dielectric block and the clad layer including an angle of incidence at which attenuation in total internal reflection is generated due to optical waveguide mode excitation can be obtained, and a photodetector means which detects the intensity of the light beam reflected in total internal reflection at the interface and detects a state of waveguide mode excitation, i.e., a state of attenuation in total internal reflection (ATR).

In the leaky mode sensor with this arrangement, when the light beam is caused to impinge upon the clad layer through the dielectric block at an angle not smaller than an angle of total internal reflection, only light having a particular wave number and impinging upon the optical waveguide layer at a particular angle of incidence comes to propagate through the optical waveguide layer in a waveguide mode after passing through the clad layer. When the waveguide mode is thus excited, almost all the incident light is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer in a waveguide mode depends upon the refractive index of the sample on the optical waveguide layer, the refractive index and/or the properties of the sample related to the refractive index can be detected on the basis of the attenuation angle θsp at which the attenuation in total internal reflection occurs.

There have been known various types of measuring apparatuses such as a surface plasmon resonance sensor or a leaky mode sensor utilizing the phenomenon of attenuation in total internal reflection (ATR). The type of such measuring apparatuses depends upon the manner in which the properties of the sample are analyzed on the basis of the state of light reflected by the interface which changes with generation of the evanescent waves. In one type, the attenuation angle θsp is measured, in another type, light beams of different wavelengths are caused to impinge upon the interface and the degree of attenuation in total internal reflection is detected by the wavelength, and in still another type, a main light beam is caused to impinge upon the interface and the light beam reflected by the interface is caused to interfere with a light beam split from the main light beam before it impinges upon the interface, thereby measuring the state of interference.

In order to perform measurement on a number of samples at high speed, and to increase efficiency of handling, there has been proposed such a measuring apparatus in which a sensor well unit comprising a dielectric block having a plurality of one-dimensionally or two-dimensionally arranged sample wells open in the upper surface thereof is used, and a plurality of light beams are caused to impinge upon the sample wells in parallel, thereby separately detecting the light beams reflected by the interfaces for the respective sample wells.

In the surface plasmon resonance sensor or the leaky mode sensor of the type described above, it is sometimes necessary to perform measurement a plurality of times on a sample at intervals and to detect the change of the state. In such a case, in order to perform such measurement on a plurality of samples at high efficiency, a sensor well unit is once demounted from the measuring apparatus after a first measurement on the sample placed in its sample well and then mounted again on the measuring apparatus after measurement on the samples placed in the sample wells of another one or more sensor well units. Conventionally, there has been a problem that the position of the base line (the interface) changes each time the same sensor well unit is mounted on the measuring apparatus, that is, the preceding base line is tilted to the next base line. When the tilt of the base line is in a longitudinal direction in which the angle of incidence of the light beam to impinge upon the base line is changed, the angle of reflection of the detecting light beam is also shifted, which deteriorates the accuracy of measurement.

Also tilt of the base line in the transverse direction intersecting the longitudinal direction can result in that the reflected light beam can travel in a direction in which it cannot be received by the photodetector. That is, tilt of the interface in both the longitudinal direction and the transverse direction can lead to deterioration of the accuracy of measurement.

SUMMARY OF THE INVENTION

In view of the foregoing observations and description, the primary object of the present invention is to provide a measuring apparatus using attenuation in total internal reflection in which tilt of the sensor well unit is prevented and the accuracy of measurement is high.

In accordance with the present invention, there is provided a first measuring apparatus utilizing the phenomenon of attenuation in total internal reflection comprising a sensor well unit having a plurality of one-dimensionally or two-dimensionally arranged sample wells, which are formed in a dielectric block to open in a flat upper surface of the dielectric block, and a thin film layer provided on the inner bottom surface of each sample well, a light beam projecting means which causes a plurality of light beams to enter the dielectric block in parallel to impinge upon the interfaces of the inner bottom surfaces of the one-dimensionally arranged sample wells out of the plurality of one-dimensionally or two-dimensionally arranged sample wells and the thin film layers thereon at various angles of incidence so that total internal reflection conditions are satisfied at each of the interfaces, and a photodetector means which is provided with a plurality of photodetector elements each positioned in correspondence to one of the interfaces to receive the light beam reflected at the interface, wherein the improvement comprises a longitudinal tilt measuring means which measures a longitudinal tilt of the interface from a predetermined reference position changing the angle of incidence of the light beam to the interface, and an operation means which obtains a corrected measured value corrected according to the longitudinal tilt measured by the longitudinal tilt measuring means.

In the first measuring apparatus, the thin film layer may be of metal film. In this case, the first measuring apparatus measures on the basis of the surface plasmon resonance.

In accordance with the present invention, there is provided a second measuring apparatus utilizing light reflected in total internal reflection comprising a sensor well unit having a plurality of one-dimensionally or two-dimensionally arranged sample wells, which are formed in a dielectric block to open in a flat upper surface of the dielectric block, and a thin film layer provided on the inner bottom surface of each sample well, a light beam projecting means which causes a plurality of light beams to enter the dielectric block in parallel to impinge upon the interfaces of the inner bottom surfaces of the one-dimensionally arranged sample wells out of the plurality of one-dimensionally or two-dimensionally arranged sample wells and the thin film layers thereon at an angle of incidence where total internal reflection conditions are satisfied at each of the interfaces, and a photodetector means which is provided with a plurality of photodetector elements each positioned in correspondence to one of the interfaces to receive the light beam reflected at the interface, wherein the improvement comprises a longitudinal tilt measuring means which measures a longitudinal tilt of the interface from a predetermined reference position changing the angle of incidence of the light beam to the interface, and a longitudinal direction adjustment means which adjusts the sensor well unit, the light beam projecting means and the photodetector means according to the longitudinal tilt measured by the longitudinal tilt measuring means to compensate for the longitudinal tilt.

In accordance with the present invention, there is provided a third measuring apparatus utilizing the phenomenon of attenuation in total internal reflection comprising a sensor well unit having a plurality of one-dimensionally or two-dimensionally arranged sample wells, which are formed in a dielectric block to open in a flat upper surface of the dielectric block, and a thin film layer provided on the inner bottom surface of each sample well, a light beam projecting means which causes a plurality of light beams to enter the dielectric block in parallel to impinge upon the interfaces of the inner bottom surfaces of the one-dimensionally arranged sample wells out of the plurality of one-dimensionally or two-dimensionally arranged sample wells and the thin film layers thereon at various angles of incidence so that total internal reflection conditions are satisfied at each of the interfaces, and a photodetector means which is provided with a plurality of photodetector elements each positioned in correspondence to one of the interfaces to receive the light beam reflected at the interface, wherein the improvement comprises a longitudinal/transverse tilt measuring means which measures a longitudinal tilt of the interface from a predetermined reference position changing the angle of incidence of the light beam to the interface and a transverse tilt of the interface from the predetermined reference position, a transverse direction adjustment means which adjusts the sensor well unit, the light beam projecting means and/or the photodetector means according to the transverse tilt measured by the longitudinal/transverse tilt measuring means to compensate for shift of the light receiving position of the photodetector means due to the transverse tilt, and an operation means which obtains a corrected measured value corrected according to the longitudinal tilt measured by the longitudinal/transverse tilt measuring means.

In accordance with the present invention, there is provided a fourth measuring apparatus utilizing light reflected in total internal reflection comprising a sensor well unit having a plurality of one-dimensionally or two-dimensionally arranged sample wells, which are formed in a dielectric block to open in a flat upper surface of the dielectric block, and a thin film layer provided on the inner bottom surface of each sample well, a light beam projecting means which causes a plurality of light beams to enter the dielectric block in parallel to impinge upon the interfaces of the inner bottom surfaces of the one-dimensionally arranged sample wells out of the plurality of one-dimensionally or two-dimensionally arranged sample wells and the thin film layers thereon at an angle of incidence where total internal reflection conditions are satisfied at each of the interfaces, and a photodetector means which is provided with a plurality of photodetector elements each positioned in correspondence to one of the interfaces to receive the light beam reflected at the interface, wherein the improvement comprises a longitudinal/transverse tilt measuring means which measures a longitudinal tilt of the interface from a predetermined reference position changing the angle of incidence of the light beam to the interface and a transverse tilt of the interface from the predetermined reference position; and a longitudinal/transverse direction adjustment means which adjusts the sensor well unit, the light beam projecting means and/or the photodetector means according to the longitudinal tilt and the transverse tilt measured by the longitudinal/transverse tilt measuring means to compensate for the longitudinal tilt and to compensate for shift of the light receiving position of the photodetector means due to the transverse tilt.

In the measuring apparatuses of the present invention, the thin film layer may be of metal film. In this case, the measuring apparatuses measure on the basis of the surface plasmon resonance.

In the measuring apparatuses of the present invention, the thin film layer may comprise a clad layer and an optical waveguide layer which is formed on the clad layer. In this case, the measuring apparatuses measure on the basis of the effect of excitation of waveguide mode in the waveguide layer.

In the second and fourth measuring apparatuses, the expression "utilizing light reflected in total internal reflection" is to be interpreted to include "to detect light beams reflected at the interface with a plurality of light beams caused to impinge upon the interface at various angles of incidence and to detect the change of the state of attenuation in total internal reflection" as in the first and third measuring apparatuses, and "causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal reflection by wavelengths as disclosed in "Porous Gold in Surface Plasmon Resonance Measurement" by D. V. Noort, K. Johansen, and C. F. Mandenius (EUROSENSORS X III, 1999, pp. 585–588) and "causing a light beam to impinge upon the interface so that total internal reflection conditions are satisfied at the interface, splitting a part of the light beam before impinging upon the interface, causing the part of the light beam to interfere with the light beam reflected in total internal reflection at the interface, and measuring the intensity of the light beam after the interference" as disclosed in "Surface Plasmon Resonance Interferometry for Micro-Array Biosensing" by P. I. Nikitin, A. N. Grigorenko, A. A. Beloglazov, M. V. Valeico, A. I. Savchuk, and O. A. Savchuk (EUROSENSORS X III, 1999, pp. 235–238).

The "predetermined reference position" is a reference position of the interface and may be either a position of the interface at a predetermined time measurement (e.g. the position of the interface at a first time measurement) or an average position of the interface in a plurality of times of measurement. Or it may be a position determined in advance by the measuring apparatus. Actually, all the places which are tilted with tilt of the interface, e.g., the bottom surface or the side surface of the sensor well unit, may be referred to.

The longitudinal tilt measured by the longitudinal tilt measuring means and the longitudinal and transverse tilts measured by the longitudinal/transverse tilt measuring means may be either a tilt itself or a value corresponding to the tilt.

"To adjust the sensor well unit, the light beam projecting means and/or the photodetector means" is to perform at least one of "to change the tilt of the sensor well unit", "to change the angle of incidence of the light beams by the light beam projecting means" and "to change the position of the photodetector means" and includes to perform any combination of two of them and to perform all of them.

In the case of the first and second measuring apparatuses, when the measuring apparatus is arranged to cause a light beam to enter the dielectric block at various angles of incidence so that total internal reflection conditions are satisfied at the interface and various angles of incidence of the light beam to the interface can be obtained, thereby measuring the state of attenuation in total reflection which occurs when the light beam impinges upon the interface at a predetermined angle of incidence, and the light beam comprises a single light beam which includes components impinging upon the interface at various angles and has a predetermined intensity distribution in a direction in which the angle of incidence to the interface changes, the longitudinal tilt measuring means may be a means for measuring the longitudinal tilt on the basis of reflection of the light beam at a part of the sensor well unit.

For example, the longitudinal tilt measuring means may measure the longitudinal tilt by the use of a component of the light beam outside the attenuation measuring range (the components of the light beam in which are used to measure the attenuation in total reflection). In this case, the longitudinal tilt measuring means may measure the longitudinal tilt on the basis of the relation between the intensity and the detecting position of a part of the components of the light beam detected by the photodetector means outside the attenuation measuring range, in which part the amount of light largely changes with change of the angle of incidence, or by causing a part of the components of the light beam outside the attenuation measuring range to impinge upon the interface as a dark line and detecting the position of the dark line included in the reflected components of the light beam by the photodetector means.

Further, the longitudinal tilt measuring means may comprise a converging lens which converges at least a part of the light beam reflected at a part of the sensor well unit, and a second photodetector means which receives the light beam converged by the converging lens and detects the position of the light beam. That is, the longitudinal tilt measuring means may detect the longitudinal tilt by way of change of the point on which the reflected light beam is converged by the converging lens.

When the converging lens is movable between a position on the optical path of the light beam and a position away from the optical path of the light beam, the photodetector means may double as the second photodetector means. In this case, the longitudinal tilt is measured with the converging lens positioned on the optical path of the light beam and the state of attenuation in total internal reflection is measured with the converging lens positioned away from the optical path of the light beam.

When the light beam contains differently polarized components, the second photodetector means may receive only the components other than a predetermined polarization component to detect the position of the light beam.

When the measuring apparatus is provided with a converging lens, the longitudinal tilt measuring means may further comprise a second lens which is disposed between the converging lens and the second photodetector means in a position where the relation between the shift of the total attenuation angle $A$ ($=L \tan \theta + x$) and the shift of the beam spot on the second photodetector means $B$ ($=\theta\{d1+d2-d1d2/f2-d0(d1/f1+d0/f1-d1d2/f1/f2-1+d2/f2)\}-x(d1/f1+d2/f1-d1d2/f1/f2-1+d2/f2)$) is $A=B$ or $A=-B$, wherein $f1$ and $f2$ represent the focal lengths of the converging lens and the second lens, $L$ represents the distance between the position at which the light beam is reflected and the photodetector means, $d0$ represents the distance between the position at which the light beam is reflected and the converging lens, $d1$ represents the distance between the converging lens and the second lens, $d2$ represents the distance between the second lens and the second photodetector means, $x$ represents the shift of the position at which the light beam is reflected based on the movement of the interface in the vertical direction, and $\theta$ represents the longitudinal tilt of the interface. When two lenses are disposed at a predetermined space on the optical path to the second photodetector means, the shift of the interface in the vertical direction can be detected as well as the vertical tilt of the interface.

For example, the converging lens, the second lens and the second photodetector means may be positioned so that $d1=f1$, $d2=f2$ and $d0=f1+L$.

In the first and second measuring apparatuses of the present invention, the longitudinal tilt measuring means may comprise a second light beam projecting means which causes a second light beam different from said light beam to impinge upon a part of the sensor well unit and a second photodetector means which receives the second light beam reflected at the part of the sensor well unit and detects the position of the second light beam.

In the third and fourth measuring apparatuses of the present invention, the longitudinal/transverse tilt measuring means may be either separately or integrally provided with means for measuring the longitudinal tilt and the transverse tilt. When the longitudinal/transverse tilt measuring means is separately provided with means for measuring the longitudinal tilt and the transverse tilt, the longitudinal tilt measuring means may the same as those described above in conjunction with the first and second measuring apparatuses.

In the case of the third and fourth measuring apparatuses, when the measuring apparatus is arranged to cause a light beam to enter the dielectric block at various angles of incidence so that total internal reflection conditions are satisfied at the interface and various angles of incidence of the light beam to the interface can be obtained, thereby measuring the state of attenuation in total reflection which occurs when the light beam impinges upon the interface at a predetermined angle of incidence, and the light beam comprises a single light beam which includes components impinging upon the interface at various angles and has a predetermined intensity distribution in a direction in which the angle of incidence to the interface changes, the longitudinal tilt measuring means may comprise a converging lens which converges at least a part of the light beam reflected at a part of the sensor well unit and a two-dimensional photodetector means which receives the light beams converged by the converging lens and detects the position of the light beam.

For example, the two-dimensional photodetector means may be a four-sectioned photodiode, a resistance type photodetector, or the like.

In the measuring apparatuses described above, when the longitudinal tilt measuring means or the longitudinal/transverse tilt measuring means is provided with a second light beam projecting means, the second light beam may be a light beam different in wavelength from said light beam, or, in the case where the light beam is of linearly polarized light of predetermined components, may be of linearly polarized light of components other than those of said light beam.

Said "a part of the sensor well unit" may be said interface or a part other than the interface. For example, it may be a predetermined surface of the sensor well unit, e.g., a side surface or a bottom surface of the dielectric block.

In each of the measuring apparatuses, the longitudinal tilt measuring means or the longitudinal/transverse measuring means may be provided one for each sensor well unit but may be provided one for each sample well.

Though measured value of the longitudinal tilt measuring means or the longitudinal/transverse tilt measuring means sometimes includes the up-and-down shift of the interface, a vertical position detecting means which detects up-and-down change of the position of the interface and a vertical position adjustment means which adjusts the up-and-down position of the interface may be further provided.

For example, the longitudinal/transverse direction adjustment means may be provided with a function of the vertical position adjustment means and the longitudinal/transverse direction adjustment means may comprise a movable stage which can incline a support table, supporting the sensor well unit, in the longitudinal direction ($\phi$) and the transverse direction ($\theta$) and can move the support table in the vertical direction, and a drive means which drives the support table.

In accordance with the first measuring apparatus of the present invention, by virtue of the operation means which obtains a corrected measured value corrected according to the longitudinal tilt measured by the longitudinal tilt measuring means which measures a longitudinal tilt of the interfaces from a predetermined reference position changing the angle of incidence, when, for instance, measurement is performed a plurality of times on a sample at intervals to detect the change of the state of attenuation in total reflection, the difference in measurement due to difference in the longitudinal tilt of the interface between times of measurement can be compensated for and measurement can be more accurately performed.

In accordance with the second measuring apparatus of the present invention, by virtue of the longitudinal direction adjustment means which adjusts the sensor well unit, the light beam projecting means and/or the photodetector means according to the longitudinal tilt measured by the longitudinal tilt measuring means which measures a longitudinal tilt of the interfaces from a predetermined reference position changing the angle of incidence, to compensate for the longitudinal tilt, when, for instance, measurement is performed a plurality of times on a sample at intervals to detect the change of the state of attenuation in total reflection, the difference in measurement due to difference in the longitudinal tilt of the interface between times of measurement can be compensated for and measurement can be more accurately performed.

In accordance with the third measuring apparatus of the present invention, by virtue of the a transverse direction adjustment means which adjusts the sensor well unit, the light beam projecting means and/or the photodetector means according to the transverse tilt measured by the longitudinal/transverse tilt measuring means which measures a longitudinal tilt of the interface from a predetermined reference position changing the angle of incidence of the light beam to the interface and a transverse tilt from a predetermined reference position, to compensate for shift of the light receiving position of the photodetector means due to the transverse tilt and the operation means which obtains a corrected measured value corrected according to the longitudinal tilt measured by the longitudinal/transverse tilt measuring means, when, for instance, measurement is performed a plurality of times on a sample at intervals to detect the change of the state of attenuation in total reflection, shift of the light receiving position of the photodetector means due to the transverse tilt due to difference in the transverse tilt of the interface between times of measurement can be compensated for and trouble that the measuring light beam cannot be received is prevented and at the same time, the difference in measurement due to difference in the longitudinal tilt of the interface between times of measurement can be compensated for and measurement can be more accurately performed.

In accordance with the fourth measuring apparatus of the present invention, by virtue of the longitudinal/transverse direction adjustment means which adjusts the sensor well unit, the light beam projecting means and/or the photodetector means according to the transverse and longitudinal tilts measured by the longitudinal/transverse tilt measuring means which measures a longitudinal tilt of the interface from a predetermined reference position changing the angle of incidence of the light beam to the interface and a transverse tilt from the predetermined reference position, to compensate for the longitudinal tilt and to compensate for shift of the light receiving position of the photodetector means due to the transverse tilt, when, for instance, measurement is performed a plurality of times on a sample at intervals to detect the change of the state of attenuation in total reflection, shift of the light receiving position of the photodetector means due to the transverse tilt due to difference in the transverse tilt of the interface between times of measurement can be compensated for and trouble that the measuring light beam cannot be received is prevented and at the same time, the difference in measurement due to difference in the longitudinal tilt of the interface between times of measurement can be compensated for and measurement can be more accurately performed.

BRIEF DESCRIPTION OF THE DRAWINGS

FIG. 1 is a plan view of a surface plasmon resonance sensor in accordance with a first embodiment of the present invention, FIG. 2 is a side view of the surface plasmon resonance sensor in accordance with the first embodiment of the present invention, FIG. 3 is a block diagram showing the electrical arrangement of the surface plasmon resonance sensor of the first embodiment.

DESCRIPTION OF THE PREFERRED EMBODIMENTS

Figure 4A:
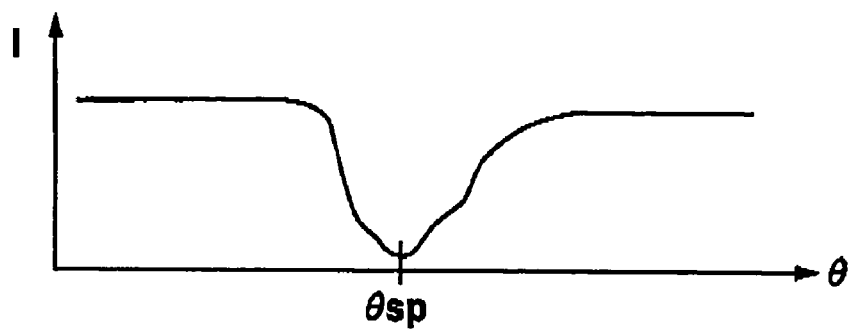
FIG. 4A is a view showing the relation between the intensity I of the light beam reflected in total internal reflection at the interface and the angle of incidence $\theta$ of the light beam.

In FIGS. 1 and 2, a measuring apparatus (a surface plasmon resonance sensor) in accordance with a first embodiment of the present invention is provided with a sensor well unit in the form of a measuring plate 200 comprising a plurality of two-dimensionally arranged sample wells (liquid wells) 201 formed in a dielectric block to open in the upper surface of the dielectric block which is flat. A metal film 12 is formed on the inner bottom surface of each sample well 201 as a thin film layer. The measuring plate 200 is formed, for instance, of transparent synthetic resin. In this particular embodiment, a sensing medium 14, which is to be combined with a particular material, is fixed on the metal film 12. Further, the measuring plate 200 is provided with a plurality of light inlet/outlet portions 202 each projecting downward from the bottom of each sample well 201. A measuring light beam L1 is caused to impinge upon the interface 202a of the light inlet/outlet portion 202 corresponding to each sample well 201 and the metal film 12 on the inner bottom face of the sample well 201. As clearly shown in FIG. 1, a plurality of the sample wells 201 are arranged in both the transverse direction (the direction of arrow P) and the longitudinal direction (the direction of arrow Q).

The surface plasmon resonance sensor of this embodiment further comprises a laser 2 emitting a laser beam L1, a light beam projecting means 1 which causes the laser beam L1 to impinge upon the bottom of the sample wells (5 in this particular embodiment) 201 of the measuring plate 200 arranged in the direction of arrow P in parallel, five (the same as the number of the sample wells 201 arranged in the direction of arrow P) photodetector means 17A to 17E each receiving the reflected light beam L1 from the interface 202a of the corresponding sample well 201, and a measuring unit feed means which feeds the measuring plate 200.

The measuring unit feed means comprises a measuring unit feed table 210, a pair of rails 211 and a drive means 212. The measuring plate 200 is set in a predetermined position on the measuring unit feed table 210. The measuring unit feed table 210 is supported on the rails 211 spaced in the direction of arrow P to extend in the direction of arrow Q and is moved along the rails 211 by the drive means 212.

The light beam projecting means 1 comprises a collimator lens 3 which converts the light beam L1, emitted from the laser 2 as a divergent light beam, into a parallel light, half-silvered mirrors 4a to 4d and a mirror 4e which branch the light beam L1, cylindrical beam expanders 5a to 5e which enlarge the diameter of the branched light beams L1 only in a plane shown in FIG. 2, mirrors 6a to 6e which reflect the enlarged light beams L1, and cylindrical lenses 7a to 7e which condense the reflected light beams L1 only in a plane shown in FIG. 2.

Each of the photodetector means 17A to 17E comprises a photodiode array formed of a number of light receiving elements arranged in a row extending in the direction of arrow X in FIG. 2.

The light beam L1 emitted from the laser 2 as a divergent light beam is collimated into a parallel light by the collimator lens 3 and branched into five beams by the half-silvered mirrors 4a to 4d and the mirror 4e. Then the five light beams L1 impinge upon the bottom surface of the corresponding sample well 201 or the interface 202a of the light inlet/outlet portion 202 corresponding to the sample well 201 and the metal film 12 on the inner bottom face of the sample well 201.

The diameter of the branched light beams L1 are enlarged by the cylindrical beam expanders 5a to 5e only in a plane shown in FIG. 2, and then the branched light beams L1 are reflected by the mirrors 6a to 6e and condensed by the cylindrical lenses 7a to 7e only in a plane shown in FIG. 2. Accordingly each light beam L1 impinges upon the interface 202a of the light inlet/outlet portion 202 and the metal film 12 with components having various angles of incidence. The laser 2 is positioned so that the light beam L1 impinges upon the interface 202a in a p-polarized state. Otherwise, the direction of polarization of the light beam L1 may be controlled by a wavelength plate.

Since converged as described above, the light beam L1 includes components impinging upon the interface 202a at various angles of incidence θ. The angles of incidence θ are all not smaller than the angle of total internal reflection. Accordingly, the laser beam L1 is reflected in total internal reflection at the interface 202a and the reflected laser beam L1 includes components reflected at the interface 202a at various angles of reflection. The light beam projecting means 1 may be arranged to cause the laser beam L1 to impinge upon the interface 202a not in a spot but in a defocused state. This arrangement widens the area on the interface 202a at which the light beam L1 is reflected in total internal reflection and averages errors in detecting states of surface plasmon resonance, whereby measuring accuracy is improved.

The light beams L1 reflected in total internal reflection at the interface 202a are detected by the photodetector means 17A to 17E. In this particular embodiment, each of the photodetector means 17A to 17E are a photodiode array in which a plurality of photodiodes 17a, 17b, 17c . . . are arranged in a row in a direction substantially normal to the direction of travel of the collimated light beam L1 in a plane of FIG. 1. That is, the components of the reflected laser beam L1 impinge upon different photodiodes 17a, 17b, 17c . . . .

In this embodiment, measurements on the samples 15 stored in five sample wells 201 arranged in a row can be performed in parallel. When measurements on the samples 15 stored in five sample wells 201 arranged in a row are finished, the laser 2 is once stopped, and the drive means 212 drives the measuring unit feed table 210, that is, the measuring plate 200, in the direction of arrow Q in FIGS. 1 and 2 by a pitch of the sample wells 201 to bring five sample wells 201 in another row to the measuring position. Then the laser 2 is operated again and measurements on new samples 15 are performed. In this embodiment, measurements on lots of samples can be performed very efficiently in a short time in this way.

Though, a single laser 2 is employed in this embodiment, for instance, a pair of light sources may be employed to obtain five light beams in total by branching a light beam from one of the light sources into two light beams and branching a light beam from the other light source into three light beams.

Each of the photodetector means 17A to 17E is further provided with a differential amplifier array and a driver and the measuring apparatus of this embodiment is further provided with a signal processing section 20 such as of a computer system and a display system 21.

FIG. 3 is a block diagram showing the electrical arrangement of the surface plasmon resonance sensor of this embodiment. Though processing of a signal from one of the photodetector means will be described here by way of example, signals from other photodetector means are processed in a similar manner. In the following description, one of the photodetector means will be referred to as "the photodetector means 17" unless it is necessary to discriminate a particular one from the others, As shown in FIG. 3, a differential amplifier array 18 is connected to the photodetector means 17 and a driver 19 comprises sample hold circuits 22a, 22b, 22c which sample-hold the outputs of the respective differential amplifiers 18a, 18b, 18c . . . of the differential amplifier array 18, a multiplexer 23 into which the outputs of the sample hold circuits 22a, 22b, 22c . . . are input, an A/D converter 24 which digitizes the outputs of the multiplexer 23 and inputs them into the signal processing section 20, a drive circuit 25 which drives the multiplexer 23 and the sample hold circuits 22a, 22b, 22c . . . , and a controller 26 which controls the drive circuit 25 under the control of the signal processing section 20.

The outputs of adjacent pairs of the photodiodes 17a, 17b, 17c . . . are respectively input into the differential amplifiers 18a, 1b, 18c . . . of the differential amplifier array 18. Accordingly, the outputs of the differential amplifiers 18a, 18b, 18c . . . of the differential amplifier array 18 represents differentials of the outputs of the photodiodes 17a, 17b, 17c . . . (representing the intensities of light which they detect) in the direction in which the photodiodes 17a, 11b, 17c . . . are arranged.

The outputs of the differential amplifiers 18a, 18b, 18c . . . are sample-held at predetermined timings by the respective sample hold circuits 22a, 22b, 22c . . . and input into the multiplexer 23. The multiplexer 23 inputs the outputs of the respective sample hold circuits 22a, 22b, 22c . . . into the A/D converter 24 in a predetermined order. The A/D converter 24 digitizes the outputs of the respective sample hold circuits 22a, 22b, 22c . . . and inputs them into the signal processing section 20, FIGS. 4A and 4B are views for illustrating the relation between the intensity I of the light beam L1 reflected in total internal reflection at the interface 202a and the outputs of the differential amplifiers 18a, 18b, 18c . . . by the angle of incidence θ of the light beam L1 and FIG. 4A is a view showing the relation between the angle of incidence θ of the light beam L1 to the interface 202a and the intensity I of the light beam L1 reflected in total internal reflection at the interface 202a.

A component of the light beam L1 impinging upon the interface 202a at a particular angle of incidence θsp excites surface plasmon in the interface 202a between the metal film 12 and the sample liquid 15 and the intensity I of the component reflected in total internal reflection at the interface 202a sharply drops. That is, the particular angle of incidence is the attenuation angle θsp and the intensity I of the reflected light beam L1 is minimized at the attenuation angle θsp. The sharp drop of the reflected light beam L1 is observed as a dark line as indicated at D in FIG. 2.

Figure 4B:
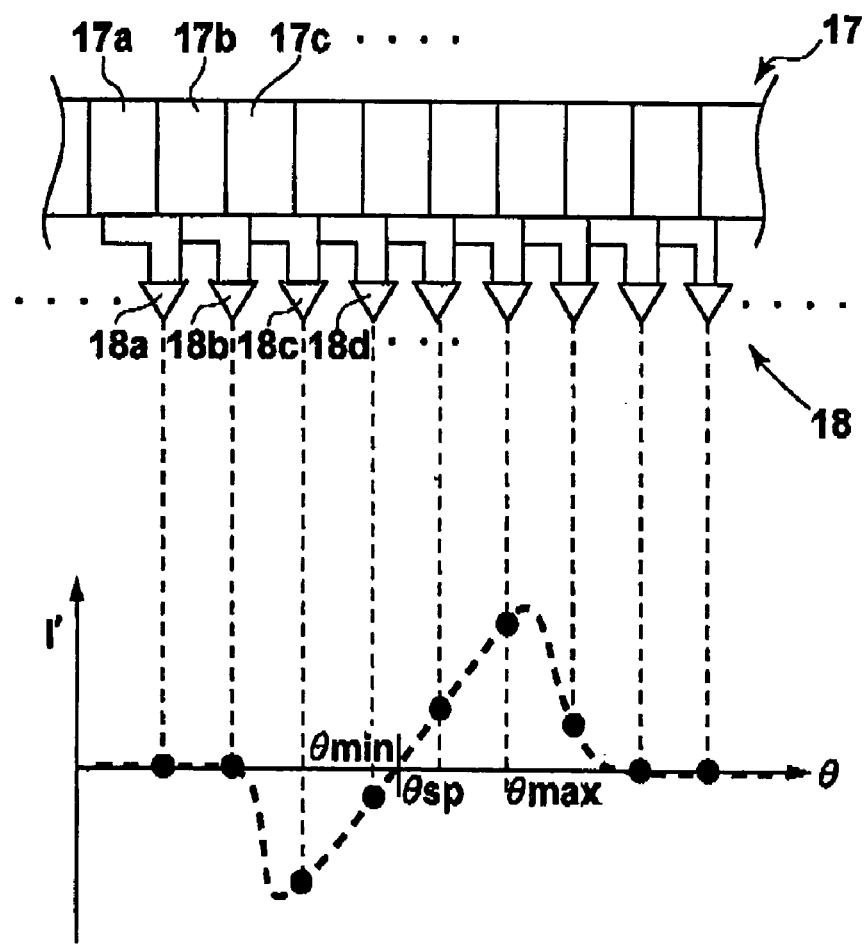
FIG. 4B is a view showing the relation between the output I' of the differential amplifier and the angle of incidence $\theta$.

FIG. 4B is a view showing the relation between the output I' of the differential amplifier and the angle of incidence θ.

As shown in FIG. 4B, the positions of the photodiodes 17a, 17b, 17c . . . in the direction in which they are arranged are one-to-one correspondence with the angle of incidence θ.

FIG. 4B also shows the relation between the output I' of the differential amplifier (the differential of the intensities I of the reflected light beam L1) and the position of the photodiode 17a, 17b, 17c . . . in the direction in which the photodiodes are arranged.

The signal processing section 20 selects one of the differential amplifiers 18a, 18b, 18c . . . whose output I' is the closest to 0 corresponding to the attenuation angle θsp on the basis of the differentials I' input into the A/D converter 24 (the differential amplifier 18d in the particular example shown in FIG. 4B) and causes the display system 21 to display the output I' of the selected differential amplifier. Sometimes there is a differential amplifier whose output I' is just 0. Naturally, the differential amplifier is selected in this case.

Thereafter, each time a predetermined time lapses, the value of the output I' of the selected differential amplifier (18d) is displayed. The output I' increases and decreases with left and right movement of the curve shown in FIG. 4A which takes place with change of the dielectric constant or the refractive index of the material in contact with the metal film 12 of the measuring chip. Accordingly, when the output I' is kept measured, change with time of the properties (refractive index) of the material in contact with the metal film 12 can be detected.

In this particular embodiment, since a sensing medium 14 which combines with a particular material in the sample liquid 15 is fixed on the metal film 12 and the refractive index of the sensing medium 14 changes depending on the state of combination of the sensing medium 14 and the particular material, change of the state of combination of the sensing medium 14 and the particular material can be detected by keeping measuring the differential value I'. In this case, both the sample liquid 15 and the sensing medium 14 are the object of analysis. As combinations of such a specific material and a sensing medium, for instance, combinations of an antigen and an antibody have been known.

In order to display change with time of the state of combination of the particular material in the sample liquid 15 and the sensing medium 14, the difference ΔI' between the initial differential value I' (0) and the differential value I' (t) at that time may be displayed instead of displaying the differential value I' at that time.

When measuring the change with time of the differential value (I'), it is necessary to perform measurement on a sample (or a sample well) a plurality of times at predetermined intervals. In order to perform measurement on a plurality of samples (sample wells) at high efficiency, the measuring plate 200 is fed by a pitch of the sample wells 201 by the measuring unit feed means to bring five sample wells 201 in another row to the measuring position so that the relevant row of the sample wells is brought to the measuring position after lapse of a predetermined time. For the same purpose, a measuring plate is sometimes once demounted to perform measurement on a second measuring plate and mounted again after measurement on the second measuring plate.

When a measuring plate is fed or mounted again, the measuring plate can be positioned in a position deviated from the position in which the preceding measurement was performed on the sample wells (or samples) thereon. In this deviation, the longitudinal tilt of the interface 202a which changes angle of incidence of the light beam L1 to the interface 202a especially largely affects the measured value.

In order to overcome this problem, the surface plasmon resonance sensor of this embodiment is provided with a longitudinal tilt measuring means which measures a longitudinal tilt of the interface from a predetermined reference position changing the angle of incidence of the light beam to the interface, and an operation means which obtains a corrected measured value corrected according to the longitudinal tilt measured by the longitudinal tilt measuring means.

That is, as shown in FIG. 2, the longitudinal tilt measuring means comprises a second light beam projecting means 32 which causes a second light beam L2 to impinge upon an outer bottom surface 202b of the measuring plate 200 to be reflected in total internal reflection, and a second photodetector means 37 which detects the second light beam L2 reflected at the outer bottom surface 202b of the light inlet/outlet portion 202 of the measuring plate 200. Though, in this embodiment, reflected at the outer bottom surface 202b of a light inlet/outlet portion 202 of the measuring plate 200, the second light beam L2 may be reflected at any surface so long as it is tilted with tilt of the interface 202a. For example, the second light beam L2 may be caused to impinge upon even the interface 202a. The second photodetector means 37 may comprise, for instance, a line photodetector such as a photodiode array as employed in the photodetector means 17. That is, the second photodetector means 37 comprises a plurality of photodiodes arranged in a direction in which the direction of travel of the reflected second light beam changes (the direction of arrow K in FIG. 2) due to change of the angle of incidence of the second light beam L2 to the outer bottom surface 202b (i.e., the angle of reflection) caused in response to longitudinal tilt of the interface 202a, and detects the shift of the second light beam receiving position (the position in which the second light beam L2 is received) in the direction of arrow K. The output SR of the second photodetector means 37 is sent to the signal processing section 20 and a corrected measured value corrected according to the longitudinal tilt of the interface 202a is obtained in the signal processing section 20 by adding a correction signal to a signal from the photodetector means 17 which detects a plasmon resonance signal. That is, the corrected measured value is obtained by adding or subtracting the difference in the angle of interface (tilt) obtained by the signal from the second photodetector means 37 to or from the angle obtained from the plasmon resonance signal. In this particular embodiment, the signal processing section 20 forms the operation means. The second light beam L2 impinges upon the outer bottom surface 202b of a light inlet/outlet portion 202 of the measuring plate 200 in a s-polarized state unlike the light beam L1. In this particular embodiment, a longitudinal tilt measuring means is provided one for one measuring plate 200, i.e., for a plurality of sample wells 201.

When measurement on one sample 15 is performed first time, the second light beam projecting means 32 causes the second light beam L2 to impinge upon the outer bottom surface 202b of the light inlet/outlet portion 202 of the measuring plate 200 and the second photodetector means 37 detects the reflected second light beam L2. Upon the second time measurement, the reflected second light beam L2 is detected in the same manner and the shift of the second light beam receiving position in the direction of arrow K representing the longitudinal tilt of the interface 202a is obtained.

The longitudinal tilt of the interface 202a is thus detected by detecting the position of the reflected second light beam L2 and the signal processing section 20 corrects the measured value on the basis of the longitudinal tilt of the interface 202a. Upon the third time measurement and the following time measurements, corrected measured values corrected on the basis of the longitudinal tilt of the interface 202a from the position of the interface 202a upon the first time measurement are obtained, whereby a measured value in which the longitudinal tilt of the interface 202a is compensated for can be obtained and more accurate measurement can be performed.

When the state of attenuation in total reflection of a sample well 201 is measured before a sample 15 is dispensed to the sample well 201 and the bulk effect is subtracted from the measured value after the sample 15 is dispensed to the sample well 201 in order to measure the state of attenuation in total reflection of the sample 15, the reliability of the measured value deteriorates when the interface 202a is tilted before dispensation of the sample to the sample well 201. Also in this case, the measured value after dispensation of the sample to the sample well 201 may be corrected on the basis of the longitudinal tilt of the interface to increase the reliability of measurement.

Figure 5:
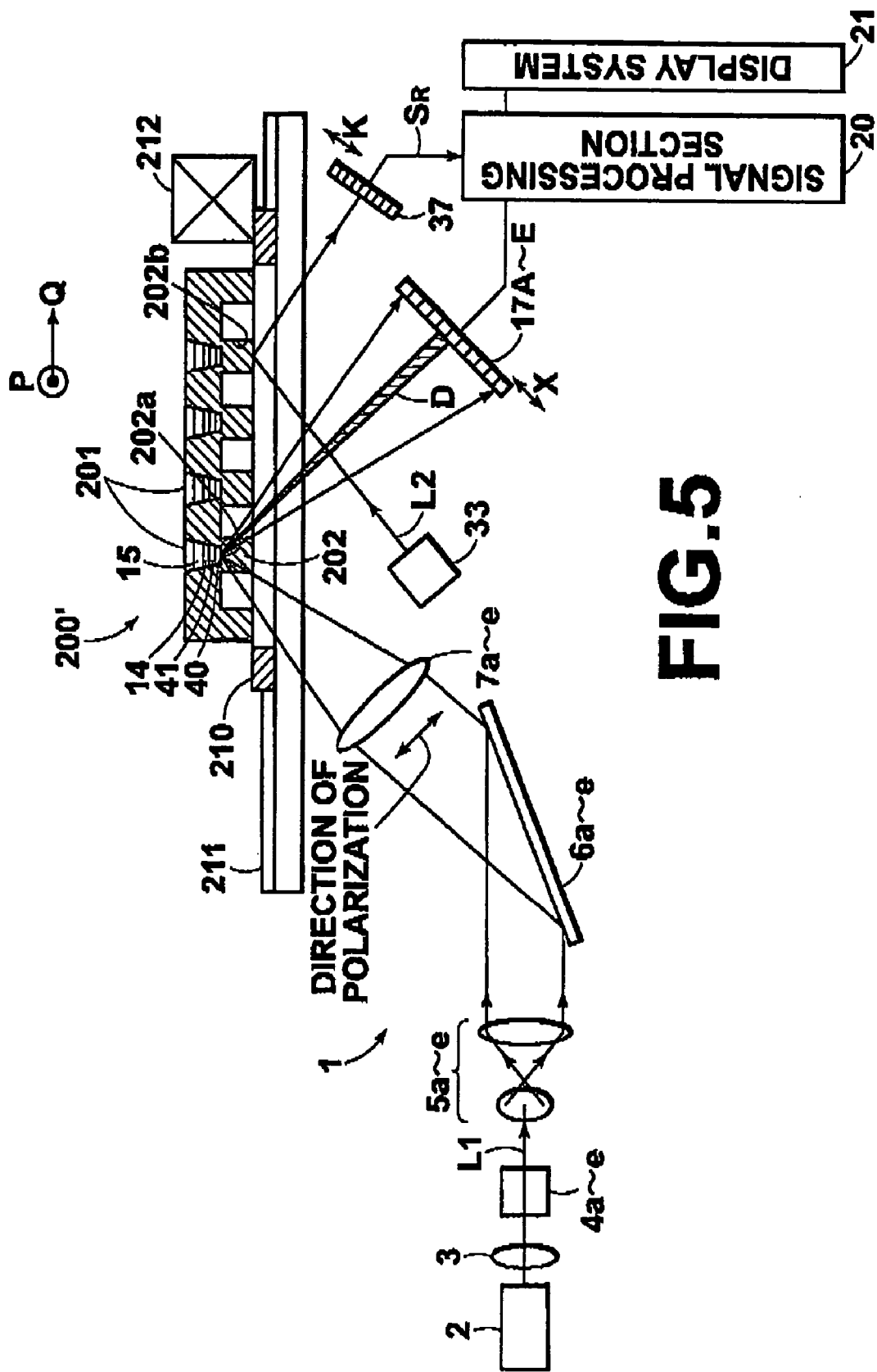
FIG. 5 is a side view of a leaky mode sensor in accordance with a second embodiment of the present invention.

A second embodiment of the present invention will be described with reference to FIG. 5, hereinbelow. In FIG. 5, the elements analogous to those shown in FIG. 1 are given the same reference numerals and will not be described here.

The measuring apparatus of the second embodiment is a leaky mode sensor described above, and is provided with a measuring plate 200' having a plurality of sample wells 201 similarly to the measuring plate 200 described above. The measuring apparatus of this embodiment is the same as the surface plasmon resonance sensor of the first embodiment except that a clad layer 40 is formed on the inner bottom surface of each sample well 201 in place of the metal film and an optical waveguide layer 41 is formed on the clad layer 40.

In the leaky mode sensor of the second embodiment, the measuring plate 200' is formed of synthetic resin or optical glass (e.g., BK7), and the clad layer 40 is in the form of film of dielectric material or metal (e.g., gold) which is lower in refractive index than the measuring plate 200'. The optical waveguide layer 41 is in the form of film of dielectric material which is higher in refractive index than the clad layer 40 (e.g., PMMA). For example, the clad layer 40 is 36.5 nm in thickness when it is in the form of a metal film and the optical waveguide layer 41 is 700 nm in thickness when it is formed of PMMA.

In the leaky mode sensor with this arrangement, when the light beam L1 emitted from the laser 2 is caused to impinge upon the clad layer 40 through the light inlet/outlet portion 202 at an angle not smaller than an angle of total internal reflection, the light beam L1 reflected in total reflection at the interface 202a of the light inlet/outlet portion 202 and the clad layer 40 and only light having a particular wave number and impinging upon the optical waveguide layer 41 at a particular angle of incidence comes to propagate through the optical waveguide layer 41 in a waveguide mode after passing through the clad layer 40. When the waveguide mode is thus excited, almost all the incident light is taken in the optical waveguide layer 41 and accordingly, the intensity of light reflected in total internal reflection at the interface 202a sharply drops. That is, attenuation in total internal reflection occurs.

Since the wave number of light to be propagated through the optical waveguide layer 41 in a waveguide mode depends upon the refractive index of the sample 15 on the optical waveguide layer 41, the refractive index and/or the properties of the sample 15 related to the refractive index can be detected on the basis of the angle of incidence at which the attenuation in total internal reflection occurs. Further, the properties of the sample 15 can be analyzed on the basis of the intensity I of the reflected light beam impinging upon the interface 202a at an angle of incidence close to the particular angle of incidence or the differential value I' output by each of the differential amplifiers of the differential amplifier array 18.

Further the leaky mode sensor of this embodiment further comprises a second light beam projecting means 33 which causes a second light beam L2 to impinge upon an outer bottom surface 202b of the light inlet/outlet portion 202 of the measuring plate 200 to be reflected in total internal reflection, and a second photodetector means 37 which detects the second light beam L2 reflected at the outer bottom surface 202b of the light inlet/outlet portion 202 of the measuring plate 200. The output SR of the second photodetector means 37 is sent to the signal processing section 20 and a corrected measured value corrected according to the longitudinal tilt of the interface 202a is obtained in the signal processing section 20 by adding a correction signal to a signal from the photodetector means 17 which detects a plasmon resonance signal. In this particular embodiment, the signal processing section 20 forms the operation means. The second light beam L2 for measuring the tilt of the interface 202a is of a wavelength different from that of the light beam L1 for measuring attenuation in total reflection.

When measurement on one sample 15 is performed first time, the second light beam projecting means 33 causes the second light beam L2 to impinge upon the outer bottom surface 202b of the light inlet/outlet portion 202 of the measuring plate 200 and the second photodetector means 37 detects the reflected second light beam L2. Upon the second time measurement, the reflected second light beam L2 is detected in the same manner and the shift of the second light beam receiving position in the direction of arrow K representing the longitudinal tilt of the interface 202a is obtained.

The longitudinal tilt of the interface 202a is thus detected by detecting the position of the reflected second light beam L2 and the signal processing section 20 corrects the measured value on the basis of the longitudinal tilt of the interface 202a, whereby a measured value in which the longitudinal tilt of the interface 202a is compensated for can be obtained and more accurate measurement can be performed.

A surface plasmon resonance sensor in accordance with a third embodiment of the present invention will be described with reference to FIGS. 6 and 7, hereinbelow.

The surface plasmon resonance sensor of this embodiment differs from that of the first embodiment in the structure of the light beam projecting means and the photodetector means and the method of correcting the longitudinal tilt.

Figure 6:
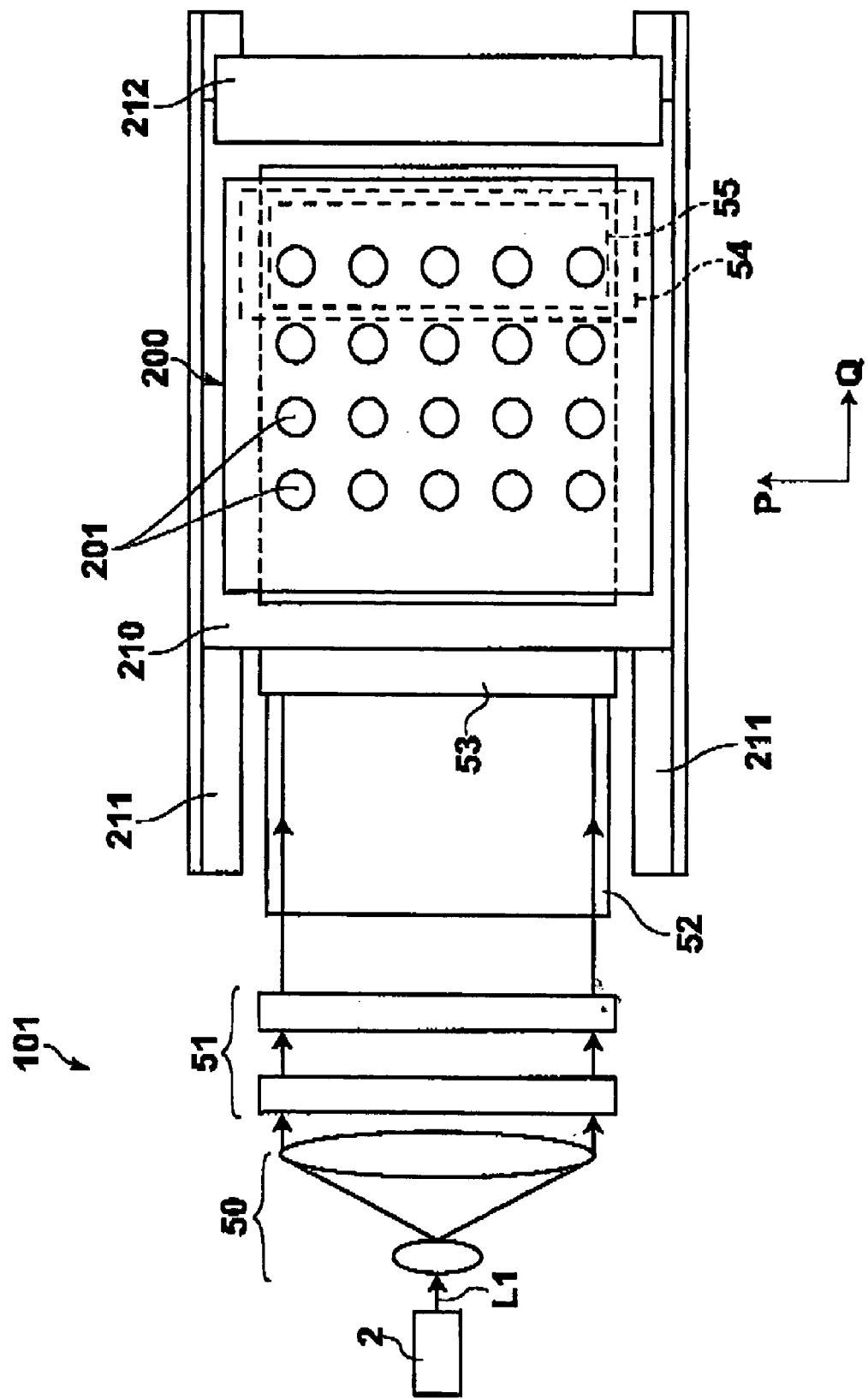
FIG. 6 is a plan view of a surface plasmon resonance sensor in accordance with a third embodiment of the present invention.
Figure 7:
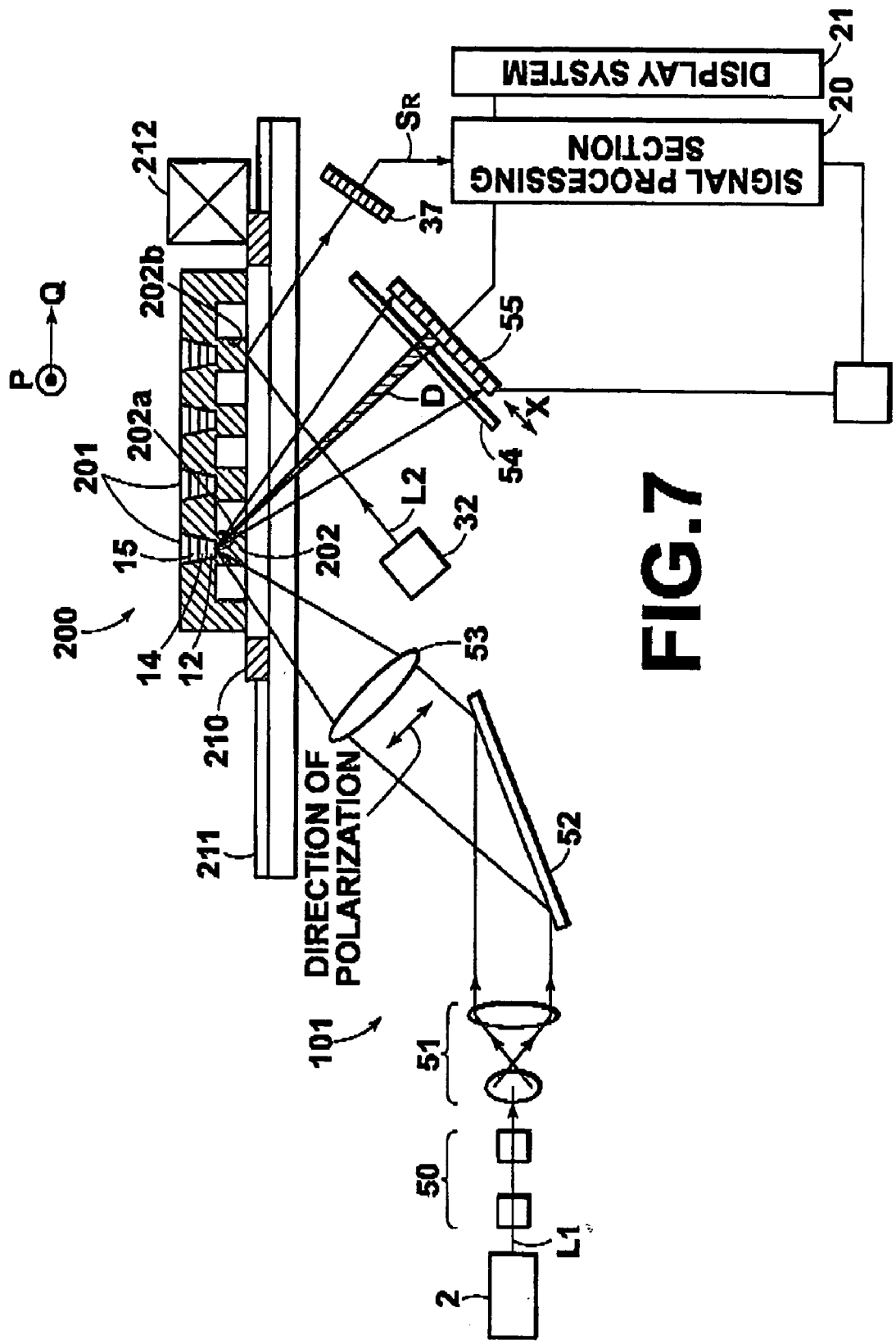
FIG. 7 is a side view of the surface plasmon resonance sensor in accordance with the third embodiment of the present invention.

The light beam projecting means 101 comprises a cylindrical beam expander 50 which enlarges the diameter of the light beam L1 emitted from the laser 2 as a divergent light beam only in a plane shown in FIG. 6, and flattens the light beam L1, a cylindrical beam expander 51 which enlarges the diameter of the flattened light beam L1 only in a plane shown in FIG. 7, a mirror 52 which reflects the light beam L1, and a cylindrical lens 53 which condense the reflected light beam L1 only in a plane shown in FIG. 7.

Figure 8:
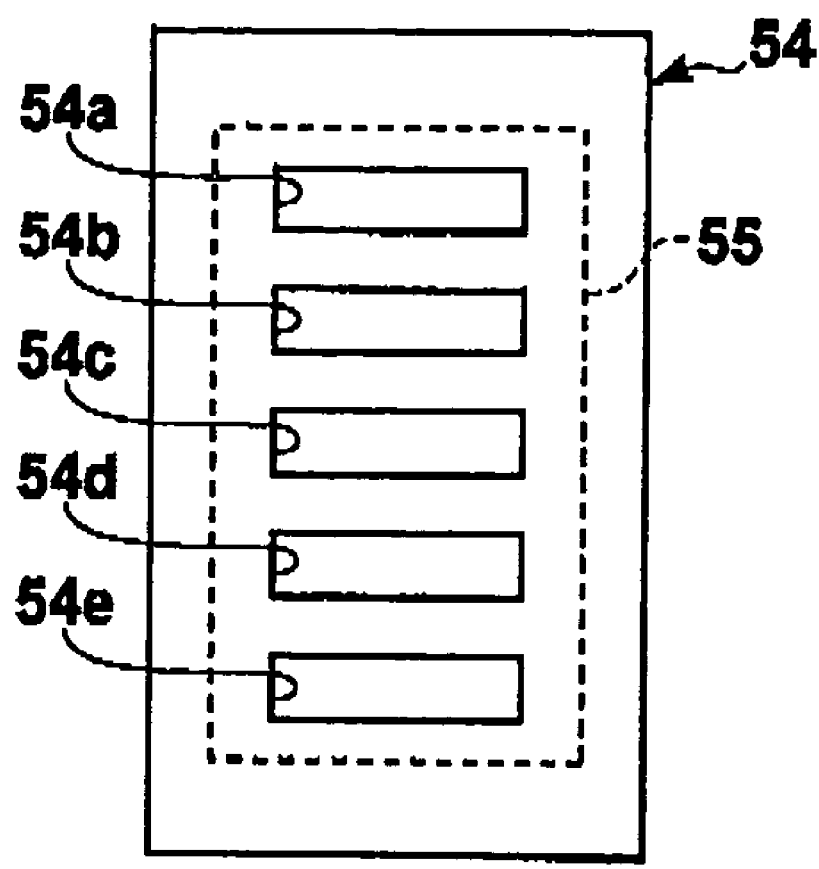
FIG. 8 is an enlarged plan view for illustrating a part of the surface plasmon resonance sensor shown in FIG. 7.

The photodetector means comprises a photodetector 55 which is, for instance, a CCD element having a two-dimensional photo-detecting face and the front face of the photodetector 55 is covered with a mask 54 having five light transmitting openings 54a to 54e as clearly shown in FIG. 8.

A flattened single light beam L1 simultaneously impinges upon the bottom surfaces of a plurality of (five in this embodiment) sample wells 201 arranged in the direction of arrow P. That is, the diameter of the light beam L1 emitted from a single laser 2 as a divergent light is enlarged by the cylindrical beam expander 50 only in a plane shown in FIG. 6, and the light beam L1 is flattened to such a size that permits the light beam L1 to simultaneously impinge upon the bottom surfaces of the five sample wells 201.

Then the flattened light beam L1 is enlarged in its diameter by the cylindrical beam expander 51 only in a plane shown in FIG. 7, reflected by the mirror 52, and condensed by the cylindrical lens 53 only in a plane shown in FIG. 7. Thus the light beam L1 impinges upon the interface 202a of the metal film 12 and the light inlet/outlet portion 202 of each sample well 201 holding components impinging upon the interface 202a at various angles. The laser 2 is positioned so that the light beam L1 (linearly polarized light) impinges upon the interface 202a in a p-polarized state.

The components of the light beam L1 reflected by the interfaces 202a corresponding to the five sample wells 201 passes through the respective light transmitting openings 54a to 54e of the mask 54 and detected by the different areas on the photodetector 55. The outputs of the five different areas on the photodetector 55 are processed independently from each other in the same manner as in the first embodiment and the particular materials in the samples 15 are quantitatively analyzed.

Also in this embodiment, measurements on the samples 15 stored in five sample wells 201 arranged in a row can be performed in parallel. When measurements on the samples 15 stored in five sample wells 201 arranged in a row are finished, the measuring plate 200 is fed by a pitch of the sample wells 201 to bring five sample wells 201 in another row to the measuring position in the same manner as in the first embodiment and measurements on new samples 15 are performed. Thus also in this embodiment, measurements on lots of samples can be performed very efficiently in a short time.

Though, a single laser 2 is employed in this embodiment, for instance, a pair of light sources may be employed by flattening a light beam from one of the light sources to such a size that permits the light beam L1 to simultaneously impinge upon the bottom surfaces of the two sample wells 201 and flattening a light beam from the other light source to such a size that permits the light beam L1 to simultaneously impinge upon the bottom surfaces of the three sample wells 201.

The measuring apparatus of this embodiment is provided with a longitudinal tilt measuring means which is the same as that of the first embodiment. That is, the longitudinal tilt measuring means comprises a second light beam projecting means 32 which causes a second light beam L2 to impinge upon an outer bottom surface 202b of the measuring plate 200 to be reflected in total internal reflection, and a second photodetector means 37 which detects the second light beam b2 reflected at the outer bottom surface 202b of the light inlet/outlet portion 202 of the measuring plate 200. The surface plasmon resonance sensor of this embodiment differs from that of the first embodiment in the means for compensating for the measured longitudinal tilt of the interface 202a.

That is, the surface plasmon resonance sensor of this embodiment is further provided with a position adjustment means (a longitudinal direction adjustment means) which moves the photodetector 55 for detecting the attenuation angle and in the direction of arrow x in FIG. 7 to compensate for the longitudinal tilt of the interface 202a measured by the second photodetector means 37. The position adjustment means comprises the photodetector 55 and the mask 54 which are movable back and forth in the direction of arrow x and drive means 35 which moves the photodetector 55 and the mask 54 under the instruction of the signal processing section 20. That is, in this embodiment, the longitudinal tilt of the interface 202a is compensated for not by correcting the measured value but by moving the photodetector means.

As can be understood from the description above, in the surface plasmon resonance sensor of this embodiment, a measured value corrected according to the longitudinal tilt detected by the longitudinal tilt measuring means is obtained by physically adjusting the position of the photodetector means.

Figure 9:
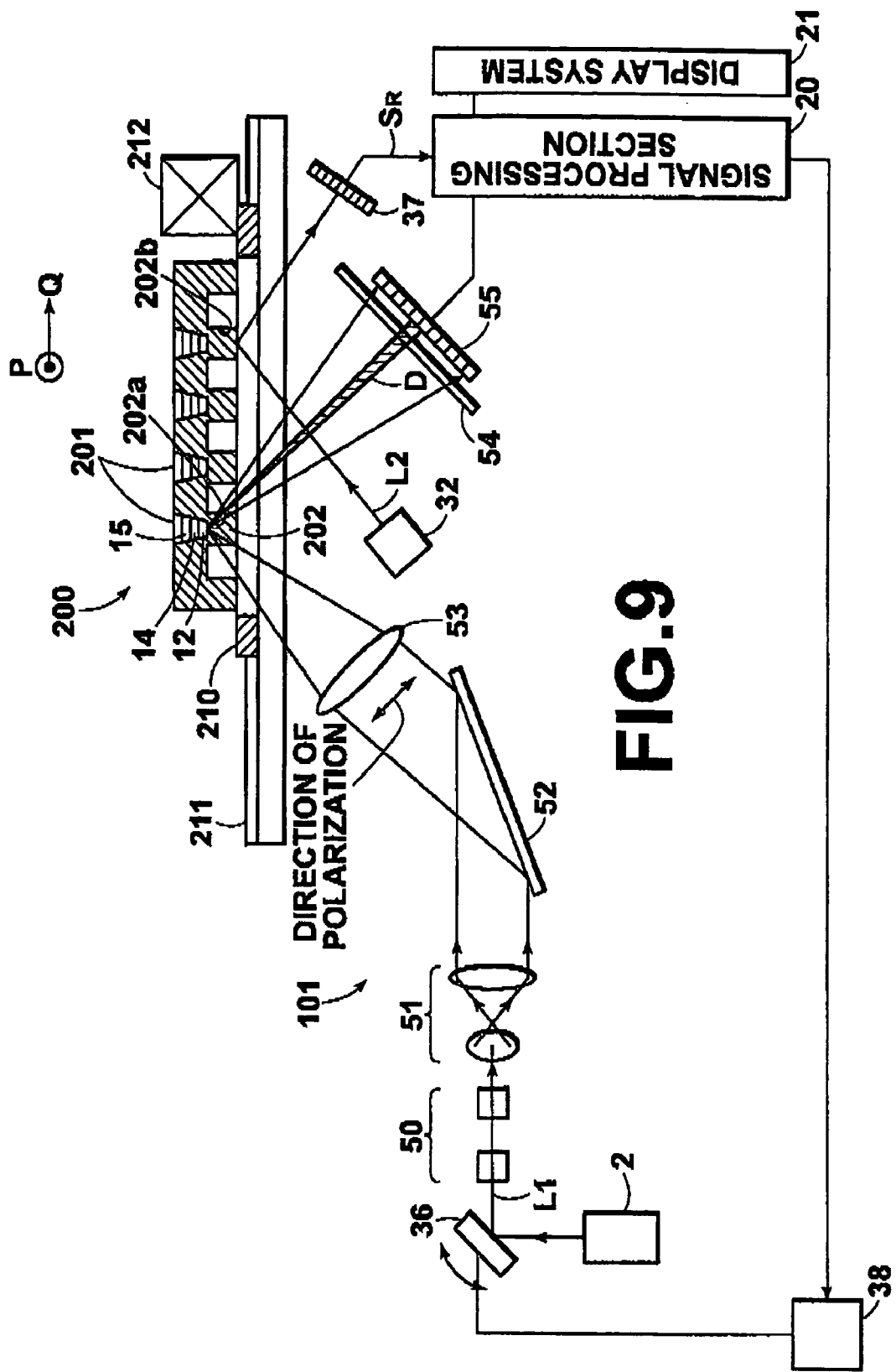
FIG. 9 is a side view of a surface plasmon resonance sensor in accordance with a fourth embodiment of the present invention.

In the surface plasmon resonance sensor in accordance with a fourth embodiment of the present invention shown in FIG. 9, the longitudinal tilt of the interface measured by the longitudinal tilt measuring means is compensated for by adjusting the angle of incidence of the light beam L1 by an incident angle adjustment means. The incident angle adjustment means comprises a mirror 36 having a reflecting surface which reflects the light beam L1 from the laser 2 toward the cylindrical beam expander 50 and is rotatable to change the angle of incidence of the light beam L1 and a mirror drive means 38 which rotates the reflecting surface of the mirror 36. The mirror drive means 38 rotates the reflecting surface of the mirror 36 under the instruction of the signal processing section 20 so that the light beam L1 is reflected in substantially the same direction irrespective of the longitudinal tilt of the interface 202a.

By tilting the light beam according to the longitudinal tilt of the interface 202a measured by the longitudinal tilt measuring means, the angle of incidence of the light beam L1 to the interface 202a can be held constant, whereby result of measurement in which the longitudinal tilt of the interface 202a is compensated for can be obtained.

In place of adjusting the position of the photodetector means or the angle of incidence of the light beam to the interface, the longitudinal tilt of the interface may be compensated for by changing the inclination of the measuring plate 200 itself. Further, the longitudinal tilt of the interface may be compensated for by adjusting, for instance, the positions of all of the photodetector means, the light beam projecting means and the measuring plate 200 or any two of them.

Figure 10:
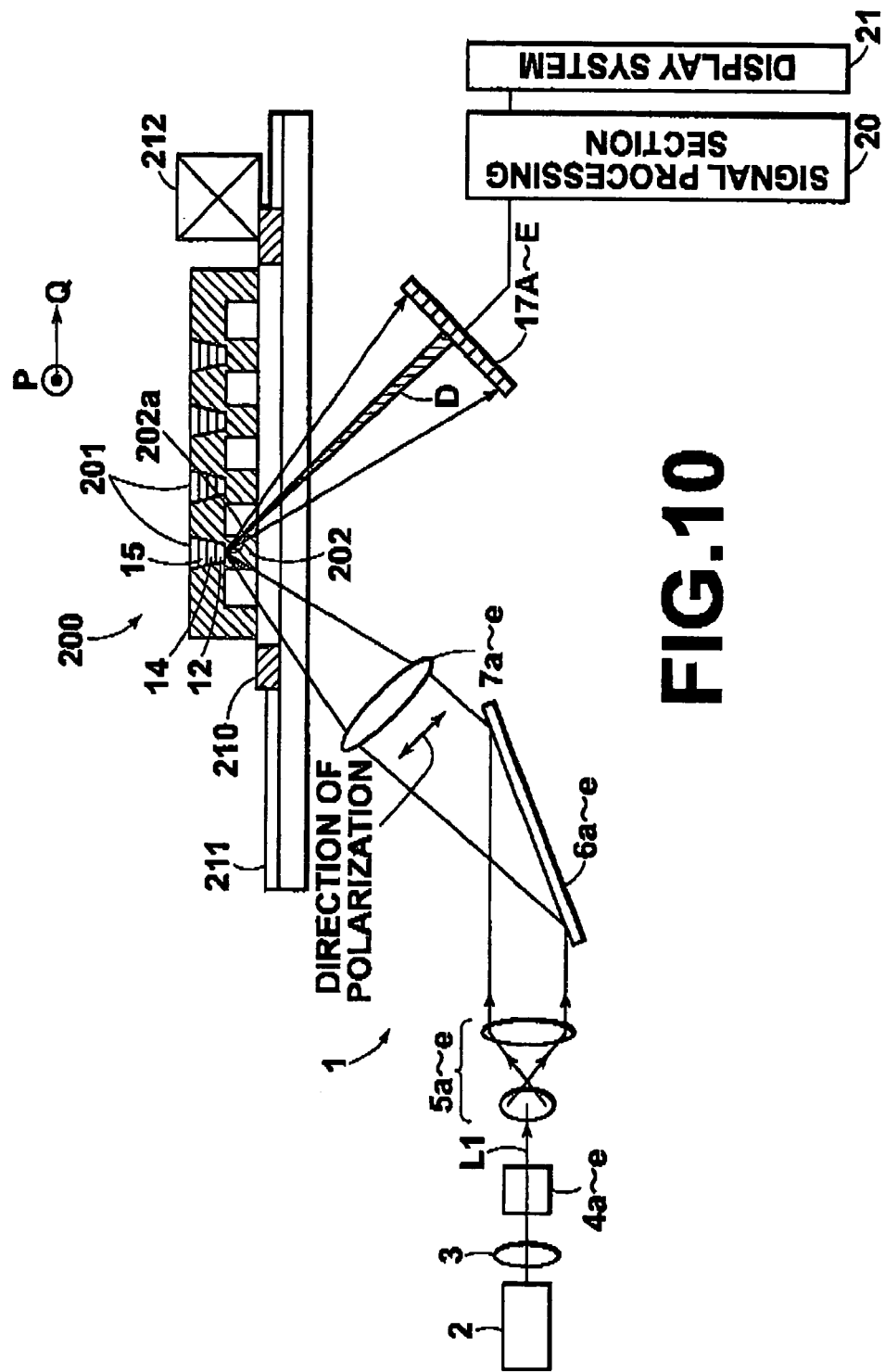
FIG. 10 is a side view of a surface plasmon resonance sensor in accordance with a fifth embodiment of the present invention.

A measuring apparatus (a surface plasmon resonance sensor) in accordance with a fifth embodiment of the present invention will be described with reference to FIGS. 10 and 11, hereinbelow. The surface plasmon resonance sensor of this embodiment is the same as the surface plasmon resonance sensor of the first embodiment in the structure of the system for measuring the surface plasmon resonance but differs from the first embodiment in the structure of the longitudinal tilt measuring means.

Figure 11:
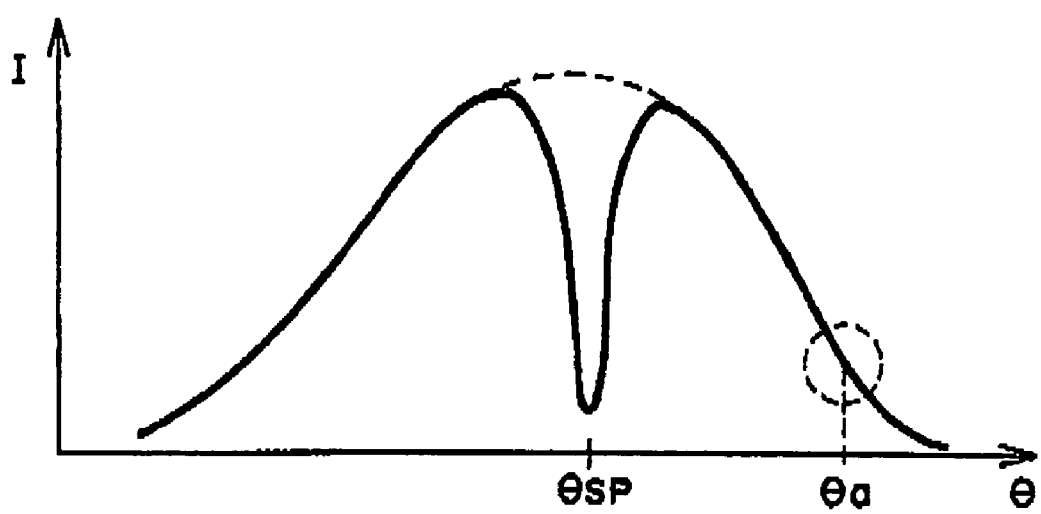
FIG. 11 is a view showing an intensity distribution of the reflected light in the surface plasmon resonance sensor in accordance with the fifth embodiment.

A light beam whose intensity distribution is a Gaussian distribution as partly shown by the broken line in FIG. 11 is generally employed in a surface plasmon resonance sensor.

Generally, the attenuation angle $\theta sp$ falls on the vicinity of the peak intensity, and change with time of the attenuation angle $\theta sp$ is observed. Accordingly, opposite end portions of the Gaussian distribution hardly contribute to measurement.

In this particular embodiment, the longitudinal tilt of the interface 202a is detected by the use of a component of the light beam which is not used for measurement. The part of the light beam outside the measuring range of the Gaussian distribution is a range where the relation between the intensity and the angle of incidence (the angle of reflection) does not change unless there exists a difference in the angle (tilt) of the interface. In this embodiment, the amount of light of a part where the change in the amount of light is sharp as surrounded by a broken line circle in FIG. 11 is detected and the longitudinal tilt of the interface 202a is detected on the basis of the change of the amount of light of the part. For example, the amount of light corresponding to a part where the angle of incidence of the light beam L1 to the interface 202a is θa is detected by the photodetector means 17 (17A to 17E), and the longitudinal tilt of the interface 202a is obtained on the basis of the change of the output of a predetermined photodiode of the photodetector means 17. On the basis of the longitudinal tilt of the interface 202a thus obtained; a measured value corrected according to the longitudinal tilt of the interface 202a is obtained in the signal processing section 20. The longitudinal tilt may be detected by each of the photodetector means 17A to 17E and the measured value for each of the sample wells 201 may be corrected on the basis of the longitudinal tilt of the interface 202a detected by the corresponding photodetector means 17A to 17E otherwise the longitudinal tilt may be detected by one of the photodetector means 17A to 17E, and the measured value for each of the sample wells 201 may be corrected on the basis of the longitudinal tilt of the interface 202a detected by the photodetector means as a representative longitudinal tilt.

Figure 12:
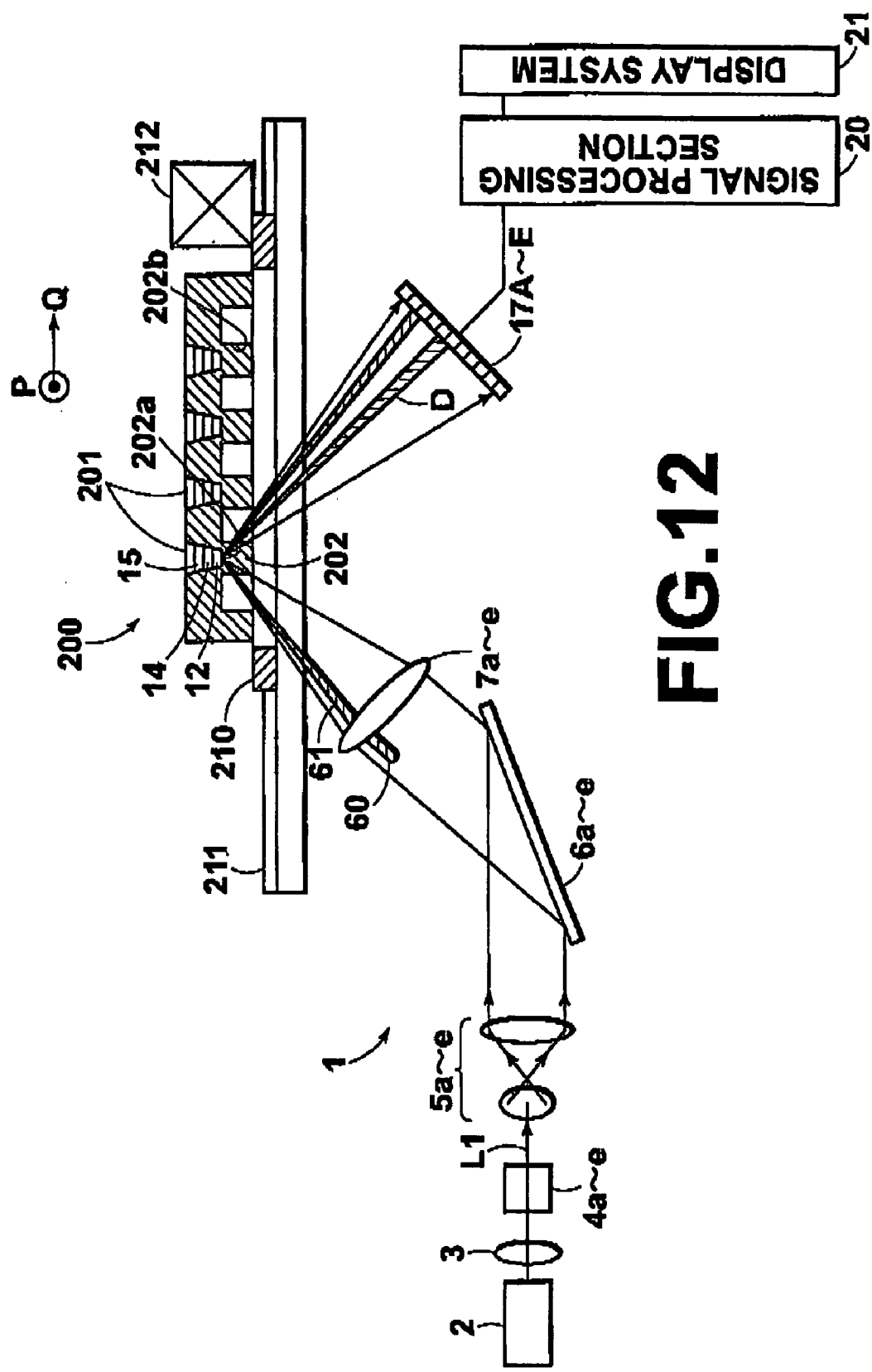
FIG. 12 is a side view of a surface plasmon resonance sensor in accordance with a sixth embodiment of the present invention.

A measuring apparatus (a surface plasmon resonance sensor) in accordance with a sixth embodiment of the present invention will be described with reference to FIGS. 12 and 13, hereinbelow.

The surface plasmon resonance sensor of this embodiment is substantially the same as the surface plasmon resonance sensor of the fifth embodiment except that a shield 60 is disposed on the incident side of the optical path of the light beam L1 so that a part of the light beam L1 impinging upon the interface 202a is a dark line 61 and the longitudinal tilt of the interface 202a is detected by detecting the dark line 61 in the reflected light beam L1.

Figure 13:
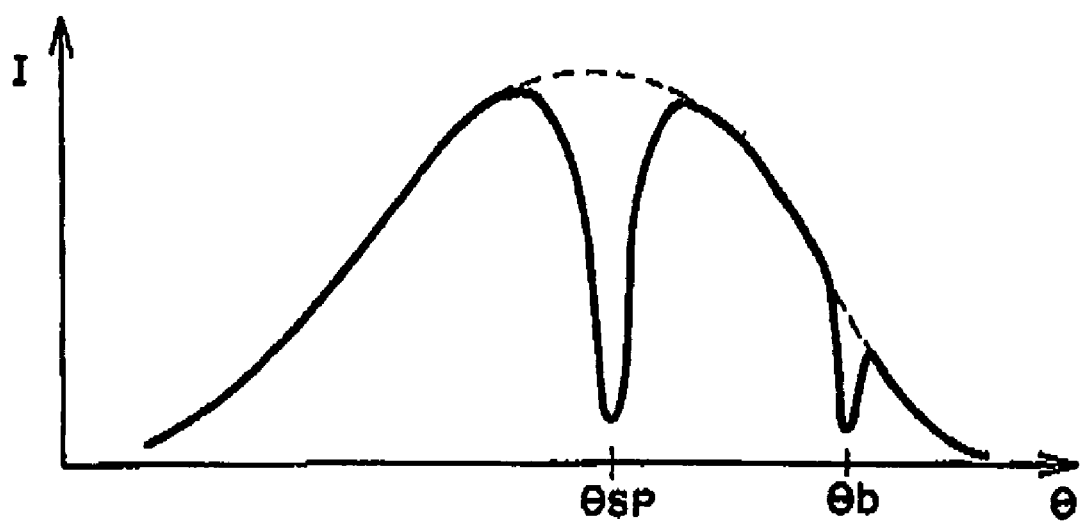
FIG. 13 is a view showing an intensity distribution of the reflected light in the surface plasmon resonance sensor in accordance with the sixth embodiment, is a plan view showing the optical system of the surface plasmon resonance sensor of the fifth embodiment.

A light beam whose intensity distribution is a Gaussian distribution as partly shown by the broken line in FIG. 13 is employed in the surface plasmon resonance sensor of this embodiment as in the surface plasmon resonance sensor of the fifth embodiment. In this particular embodiment, the longitudinal tilt of the interface 202a is detected by the use of a portion of the Gaussian distribution which hardly contributes to measurement. A part of the light beam L1 impinging upon the interface 202a is made a dark line 61 and the dark line 61 is detected by the photodetector means 17. The position on the photodetector means 17 in which the dark line 61 is detected does not change unless the longitudinal inclination of the interface 202a changes. Accordingly, the shift of the position of the dark line 61 corresponds to the longitudinal tilt of the interface 202a. For example, when the longitudinal inclination of the interface 202a changes after first time measurement, the dark line 61 detected by a photodiode corresponding to an angle θb upon the first time measurement comes to be detected by another photodiode upon second time measurement. Accordingly, which photodiode detects the dark line 61 upon the second time measurement represents the longitudinal tilt from the inclination of the interface upon the first time measurement.

On the basis of the longitudinal tilt of the interface 202a thus obtained, a measured value corrected according to the longitudinal tilt of the interface 202a is obtained in the signal processing section 20.

Figure 14:
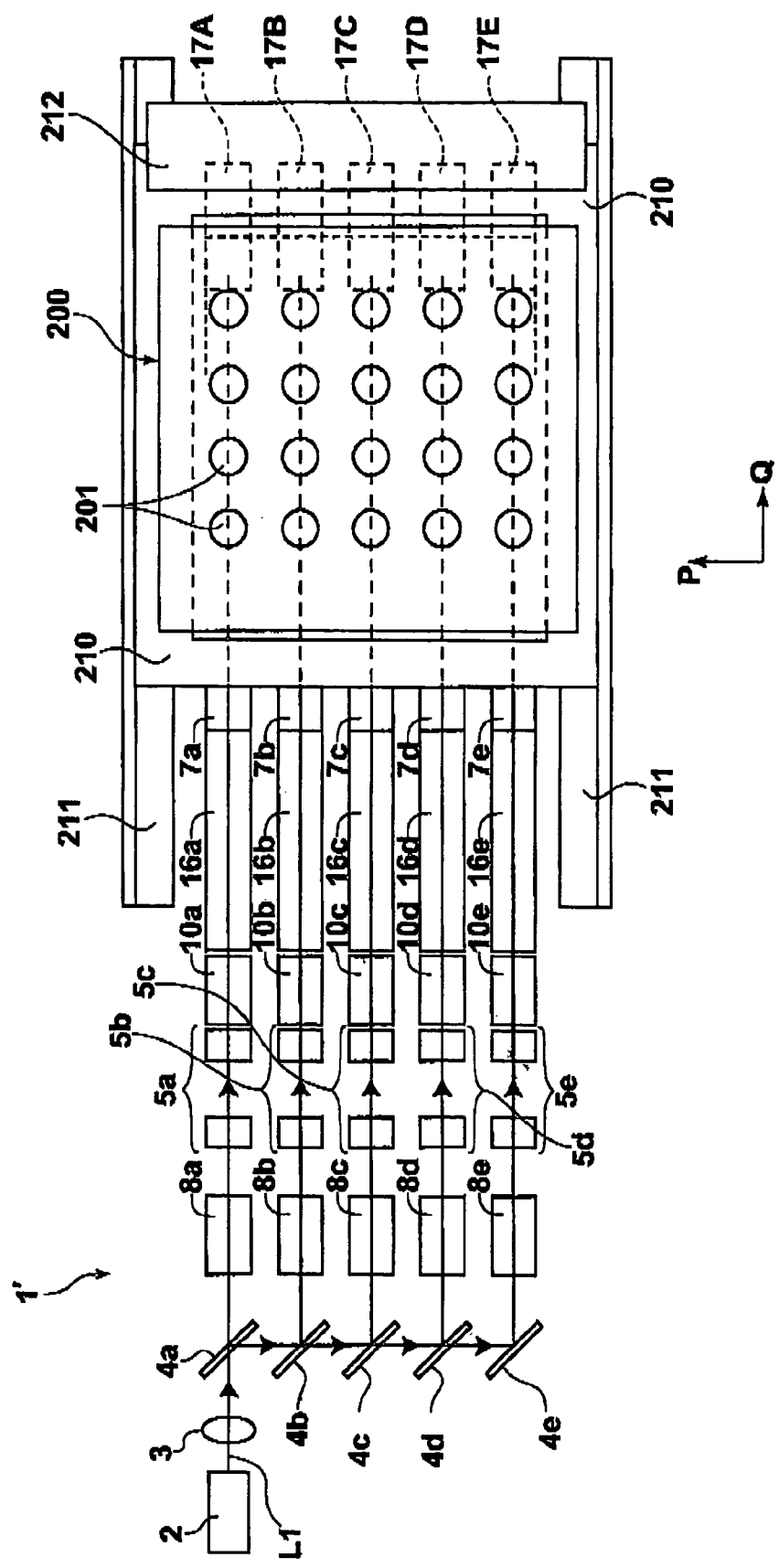
FIG. 14 is a plan view of a surface plasmon resonance sensor in accordance with a seventh embodiment of the present invention.
Figure 15:
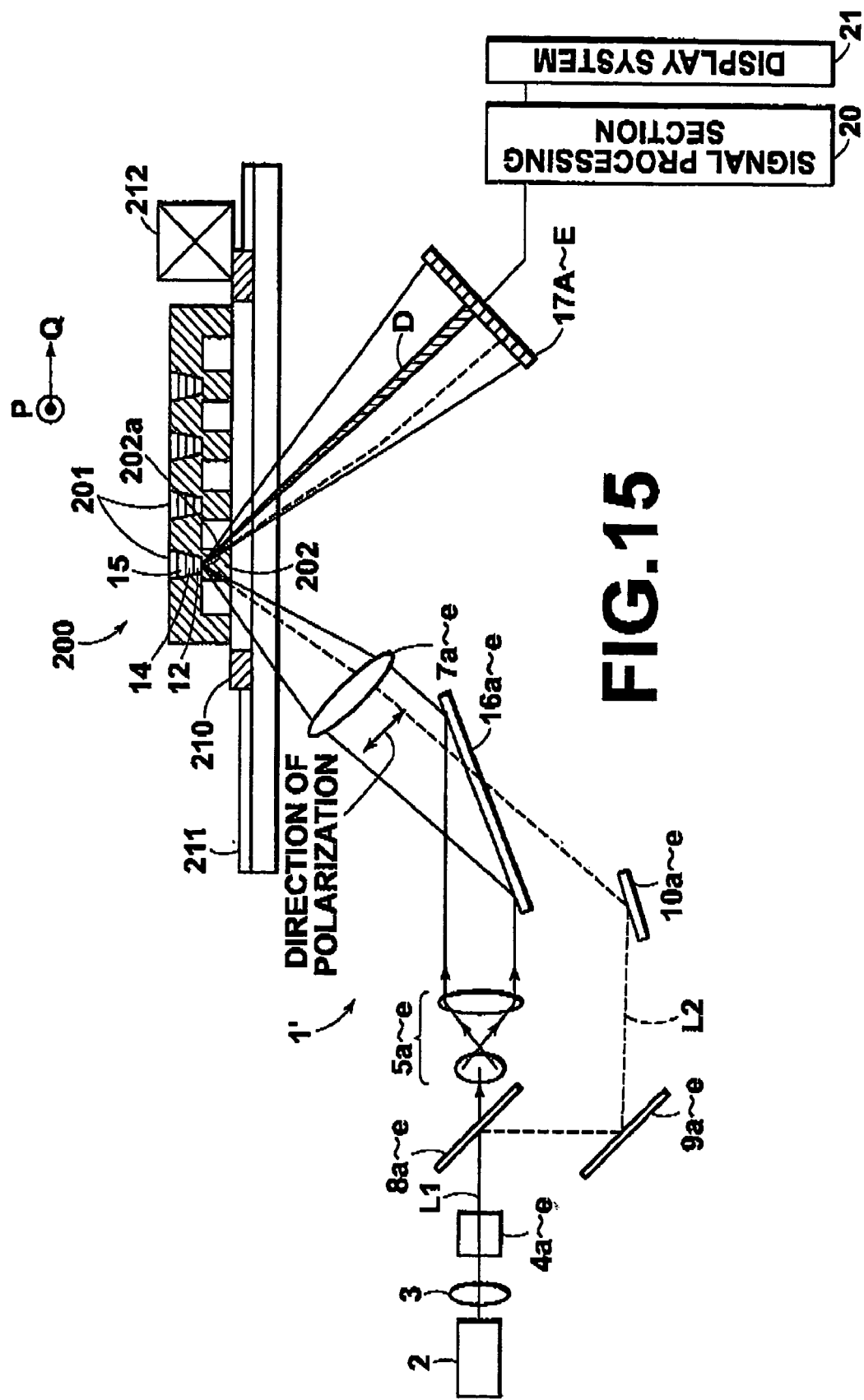
FIG. 15 is a side view of a surface plasmon resonance sensor in accordance with the seventh embodiment of the present invention.

A measuring apparatus (a surface plasmon resonance sensor) in accordance with a seventh embodiment of the present invention will be described with reference to FIGS. 14 to 16, hereinbelow.

The surface plasmon resonance sensor of this embodiment is substantially the same as the surface plasmon resonance sensor of the fifth embodiment except that half-silvered mirrors 8a to Be and mirrors 9a to 9e and 10a to 10e are disposed on the optical paths of the branched light beams L1 and PBSs 16a to 16e are provided in place of the mirrors 6a to 6e to branch a light beam from the respective branched light beams L1 and to cause the light beam branched from the respective branched light beams L1 to impinge upon the interface 202a as the second light beam L2. By virtue of the light beam projecting means 1', each of the branched light beams L1 includes components impinging upon the interface 202a at various angles and each of the second light beams L2 impinges upon the interface 202a at a predetermined angle of incidence. BY detecting an intensity projecting portion where the amount of light is prominently large due to overlap of the reflected light beam L1 and the reflected second light beam L2, the longitudinal tilt of the interface 202a can be detected.

Figure 16:
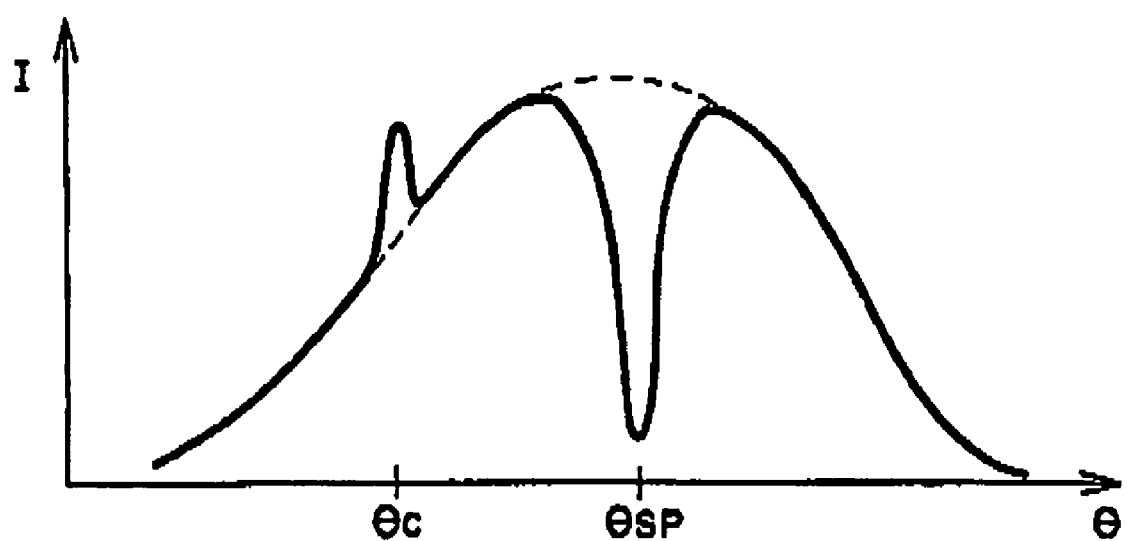
FIG. 16 is a view showing an intensity distribution of the reflected light in the surface plasmon resonance sensor in accordance with the seventh embodiment.

A light beam whose intensity distribution is a Gaussian distribution as partly shown by the broken line in FIG. 16 is employed as the light beam L1 in the surface plasmon resonance sensor of this embodiment as in the surface plasmon resonance sensor of the fifth embodiment. The second light beam L2 is caused to impinge upon the interface 202a to overlap the opposite end portions of the Gaussian distribution which hardly contribute to measurement and an intensity projecting portion where the amount of light is prominently large due to overlap of the reflected light beam L1 and the reflected second light beam L21 is detected by the photodetector means 17. The position on the photodetector means 17 in which the intensity projecting portion is detected does not change unless the longitudinal inclination of the interface 202a changes. Accordingly, the shift of the position of the intensity projecting portion corresponds to the longitudinal tilt of the interface 202a. For example, when the longitudinal inclination of the interface 202a changes after first time measurement, the intensity projecting portion detected by a photodiode corresponding to an angle θc upon the first time measurement comes to be detected by another photodiode upon second time measurement. Accordingly, which photodiode detects the intensity projecting portion upon the second time measurement represents the longitudinal tilt from the inclination of the interface upon the first time measurement. On the basis of the longitudinal tilt of the interface 202a thus obtained, a measured value corrected according to the longitudinal tilt of the interface 202a is obtained in the signal processing section 20.

Figure 17:
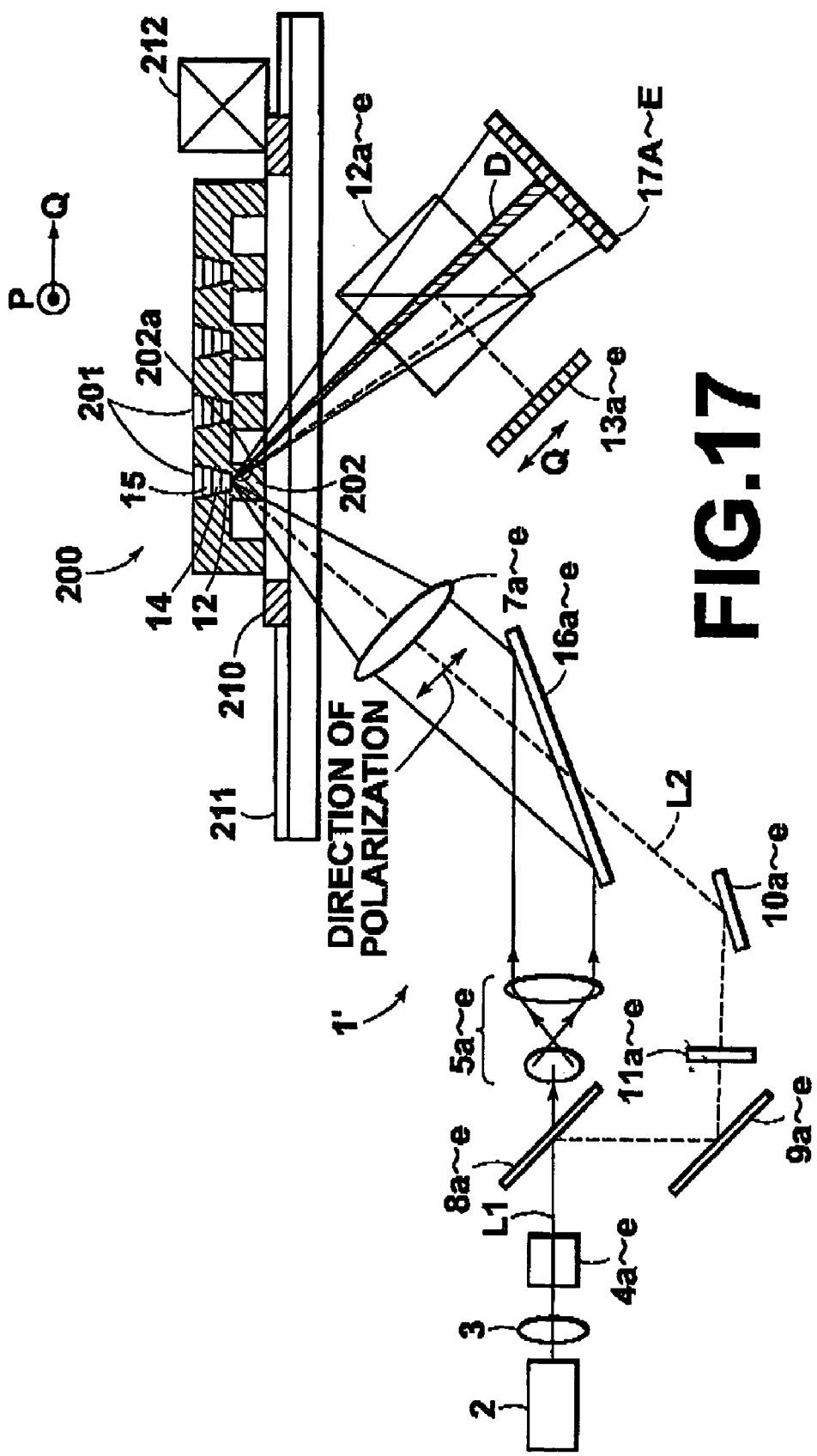
FIG. 17 is a side view of a surface plasmon resonance sensor in accordance with an eighth embodiment of the present invention.

A measuring apparatus (a surface plasmon resonance sensor) in accordance with an eighth embodiment of the present invention will be described with reference to FIG. 17, hereinbelow.

The surface plasmon resonance sensor of this embodiment is substantially the same as the surface plasmon resonance sensor of the seventh embodiment except that λ/2 plates 11a to 11e are inserted into the optical paths of the second light beams L2 and PBSs 12a to 12e are provided on the optical paths of the reflected second light beams L2 to reflect the second light beams L2 toward second photodetector means 13a to 13e which are added.

The λ/2 plates 11a to 11e convert the second light beams L2 which are small in diameter to light beams which impinge upon the interface 202a in an s-polarized state. The s-polarized second light beams L2 are caused to impinge upon the second photodetector means 13a to 13e by the PBSs 12a to 12e. Each of the second photodetector means 13a to 13e is a line sensor and the second light beam receiving position on the line sensor in the direction of arrow Q changes with change of the longitudinal tilt of the interface 202a. Accordingly, by detecting which elements receives the second light beam L2, the longitudinal tilt of the interface 202a can be detected. On the basis of the longitudinal tilt of the interface 202a thus obtained, a measured value corrected according to the longitudinal tilt of the interface 202a is obtained in the signal processing section 20.

Figure 18:
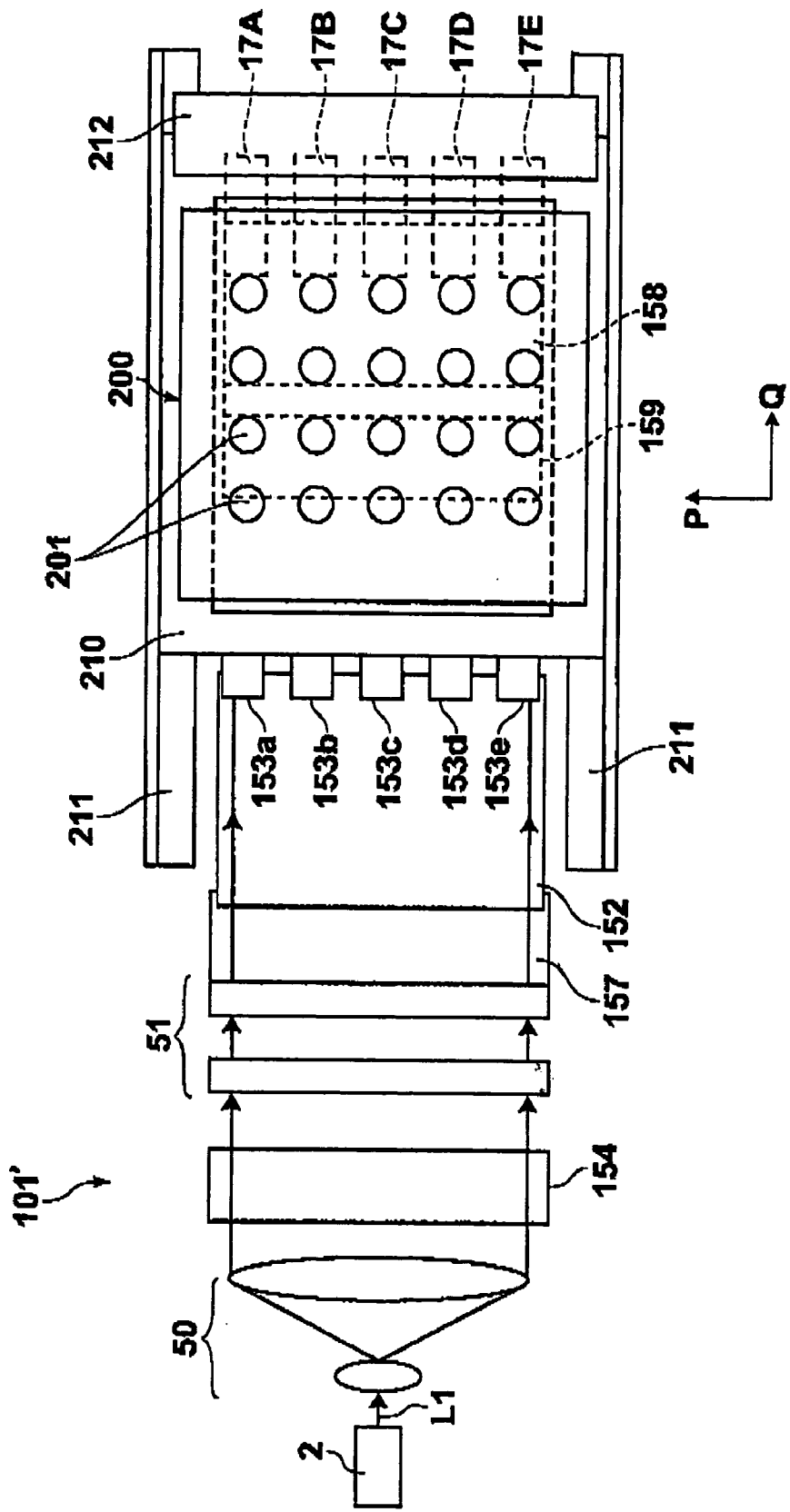
FIG. 18 is a plan view of a surface plasmon resonance sensor in accordance with a ninth embodiment of the present invention.
Figure 19:
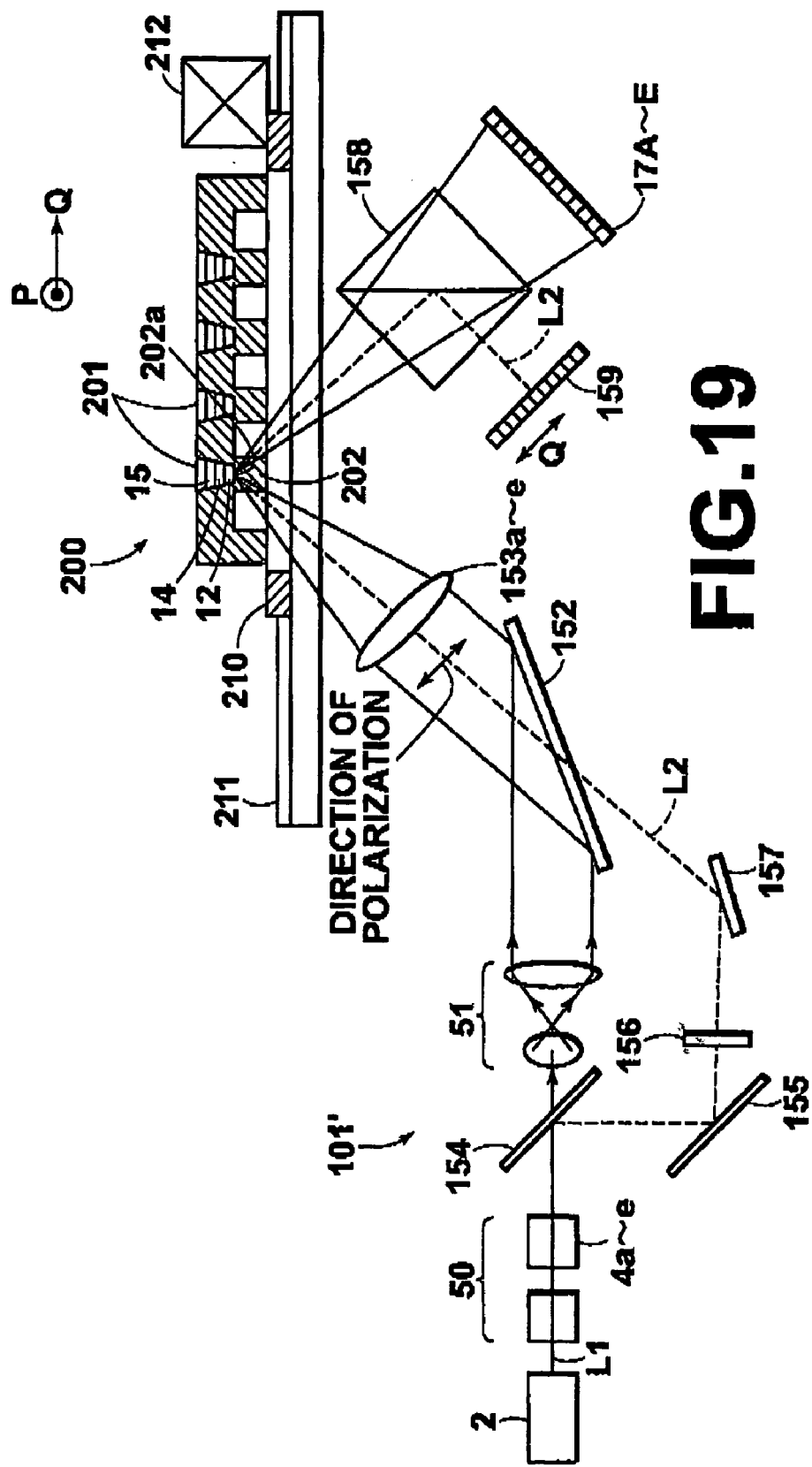
FIG. 19 is a side view of the surface plasmon resonance sensor in accordance with the ninth embodiment of the present invention.

A measuring apparatus (a surface plasmon resonance sensor) in accordance with a ninth embodiment of the present invention will be described with reference to FIGS. 18 and 19, hereinbelow.

The beam projecting means 101' of the surface plasmon resonance sensor of this embodiment is substantially the same as the beam projecting means 101 of the surface plasmon resonance sensor of the third embodiment except that a half-silvered mirror 154, a mirror 155, a λ/2 plate 156 and a mirror 157 are disposed on the optical path of the light beam L1 and a PBS 152 and cylindrical lenses 153a to 153e are provided in place of the mirror 52 and the cylindrical lens 53 to branch a light beam from the light beam L1 and to cause the light beam branched from the light beam L1 to impinge upon the interface 202a in an s-polarized state as the second light beam L2. Further, a PBS 158 is provided on the optical path of the reflected second light beam L2 to reflect the second light beam L2 toward a second photodetector means 159 which are added. By virtue of the light beam projecting means 101', the light beam L1 includes components impinging upon the interface 202a at various angles and the second light beam L2 impinges upon the interface 202a at a predetermined angle of incidence in an s-polarized state. The second light beam L2 reflected at the interface 202a is further reflected toward the second photodetector means 159 by the PBS 158 and detected by the second photodetector means 159.

The second photodetector means 159 is, for instance, a CCD sensor and the second light beam receiving position on the CCD sensor in the direction of arrow Q changes with change of the longitudinal tilt of the interface 202a. Accordingly, by detecting where the second light beam L2 is received, the longitudinal tilt of the interface 202a can be detected. On the basis of the longitudinal tilt of the interface 202a thus obtained, a measured value corrected according to the longitudinal tilt of the interface 202a is obtained in the signal processing section 20.

Measuring apparatuses in accordance with other embodiments of the present invention will be described with references to FIGS. 20 to 25, hereinbelow. Each of the following measuring apparatuses is substantially the same as those described above in the structure for measuring the attenuation in total internal reflection but is different from those described above in the structure for measuring the longitudinal tilt of the interface. Accordingly, the latter will be mainly described and the former will be described only on the changed portion.

Figure 20:
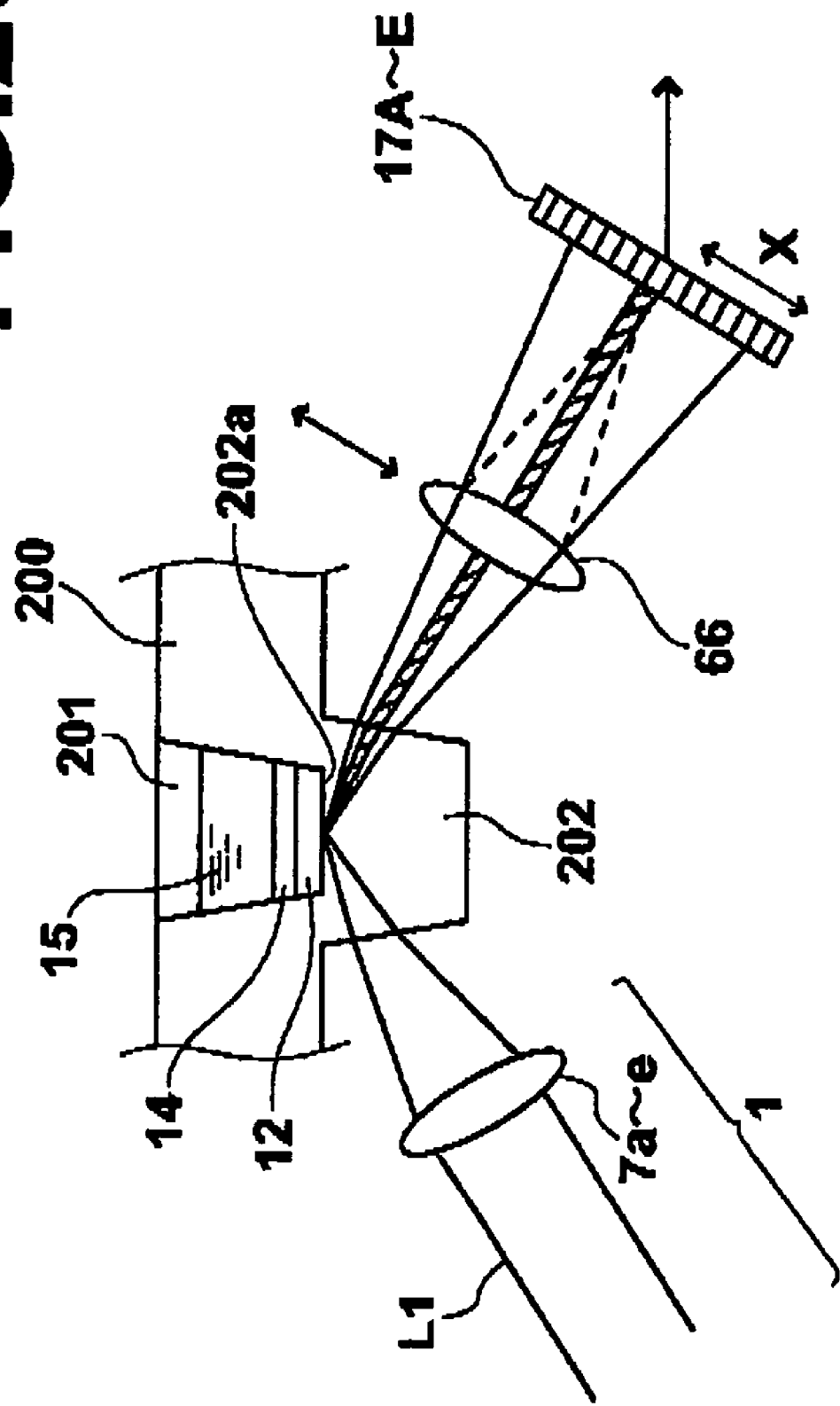
FIG. 20 is a fragmentary side view of a surface plasmon resonance sensor in accordance with a tenth embodiment of the present invention.

A measuring apparatus (a surface plasmon resonance sensor) in accordance with a tenth embodiment of the present invention will be described with reference to FIG. 20, hereinbelow.

The longitudinal tilt measuring means of the surface plasmon resonance sensor of this embodiment comprises photodetector means 17 (a plurality of photodetector means 17A to 17E) and a converging lens 66 movable between a position on the optical path of the reflected light beam L1 to the photodetector means 17 and a position outside the optical path of the reflected light beam L1. In this embodiment, the longitudinal tilt is measured with the converging lens 66 held in the position on the optical path of the reflected light beam L1, and the state of the attenuation in total internal reflection is measured with the converging lens 66 held in the position outside the optical path of the reflected light beam L1. That is, in this embodiment, the reflected light beam L1 is converged on the surface of the photodetector means 17 by the converging lens 66 and the longitudinal tilt of the interface 202a is detected by measuring the position of the converged light beam L1 on the photodetector means 17 in the direction of arrow X.

Figure 21:
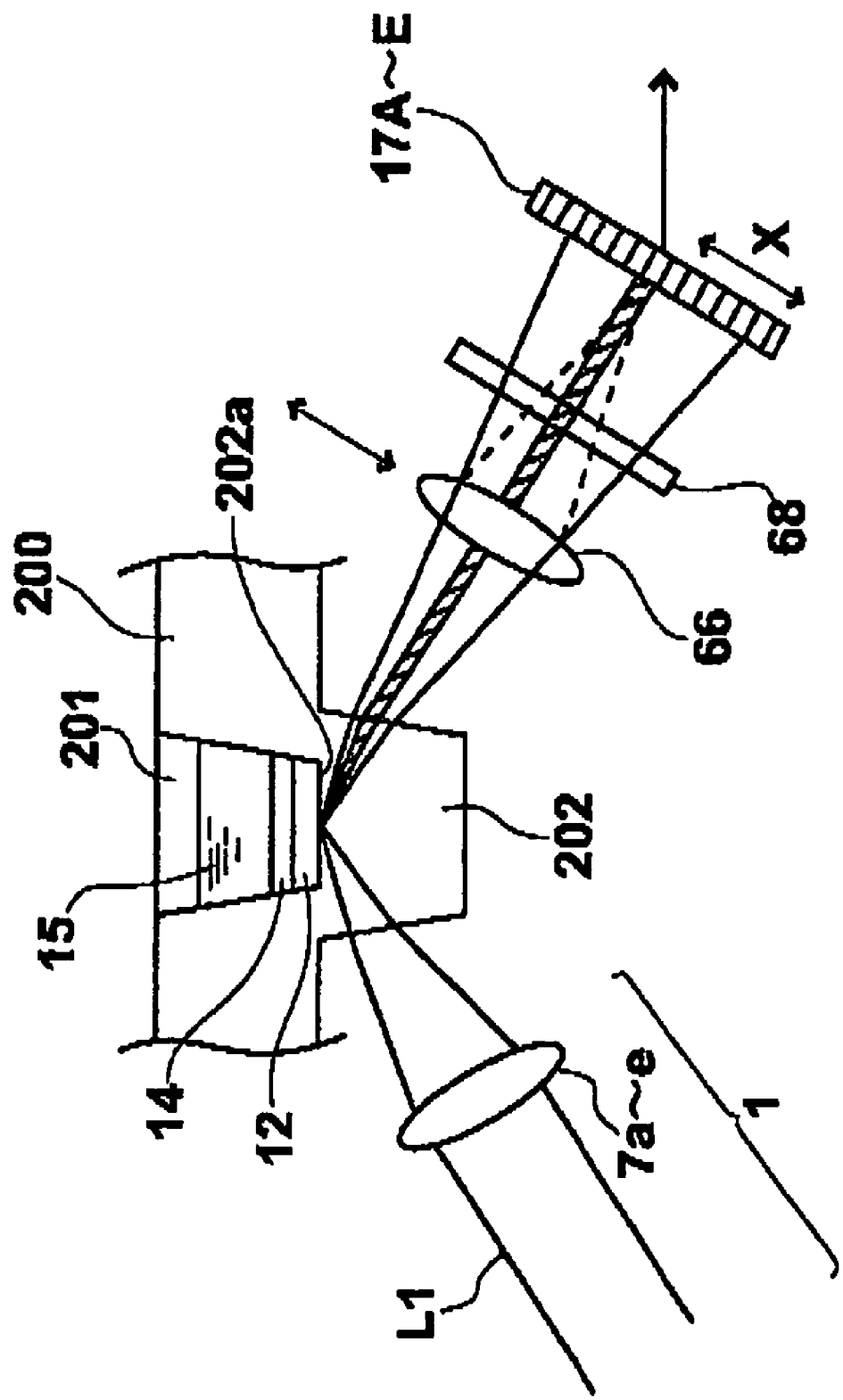
FIG. 21 is a fragmentary side view of a surface plasmon resonance sensor in accordance with a eleventh embodiment of the present invention.

In this embodiment, the light beam L1 is caused to impinge upon the interface 202a in a p-polarized state and the state of a generated dark line is measured. In the case where the light beam L1 includes a plurality of polarization components, it is necessary for the photodetector means 17 to detect only a p-polarization component in order to detect the state of the attenuation in total internal reflection. Accordingly, when the light beam L1 includes a polarization component other than a p-polarization component, an analyzer 68 is disposed upstream of the photodetector means 17 as shown in FIG. 21, which is a side view showing an eleventh embodiment of the present invention, so that only a p-polarization component can impinge the photodetector means 17. When the longitudinal tilt is to be measured, for instance, the analyzer 68 is rotated so that only an s-polarization component normal to the p-polarization component can impinge upon the photodetector means 17.

A measuring apparatus (a surface plasmon resonance sensor) in accordance with a twelfth embodiment of the present invention will be described with reference to FIG. 22, hereinbelow.

The longitudinal tilt measuring means of the surface plasmon resonance sensor of this embodiment comprises a second photodetector means 72, a half-silvered mirror 70 disposed in a position on the optical path of the reflected light beam L1 to the photodetector means 17 (a plurality of photodetector means 17A to 17E), and a converging lens 71 which converges on the surface of the second photodetector means 72 a part of the reflected light beam L1 separated by the half-silvered mirror 70. That is, the reflected light beam L1 is split into two parts by the half-silvered mirror 70 and one of the parts is used for measuring the attenuation in total internal reflection with the other of the parts used for measuring the longitudinal tilt of the interface 202a. Apart of the light beam L1 reflected by the half-silvered mirror 70 is converged on the surface of the second photodetector means 72 by the converging lens 71 and the longitudinal tilt of the interface 202a is detected by measuring the position of the converged light beam on the second photodetector means 72 in the direction of arrow Q.

A mirror may be provided in place of the half-silvered mirror 70 to be movable between a position on the optical path of the reflected light beam L1 to the photodetector means 17 and a position outside the optical path of the reflected light beam L1. In this case, the longitudinal tilt is measured with the mirror held in the position on the optical path of the reflected light beam L1, and the state of the attenuation in total internal reflection is measured with the mirror held in the position outside the optical path of the reflected light beam L1.

Figure 23:
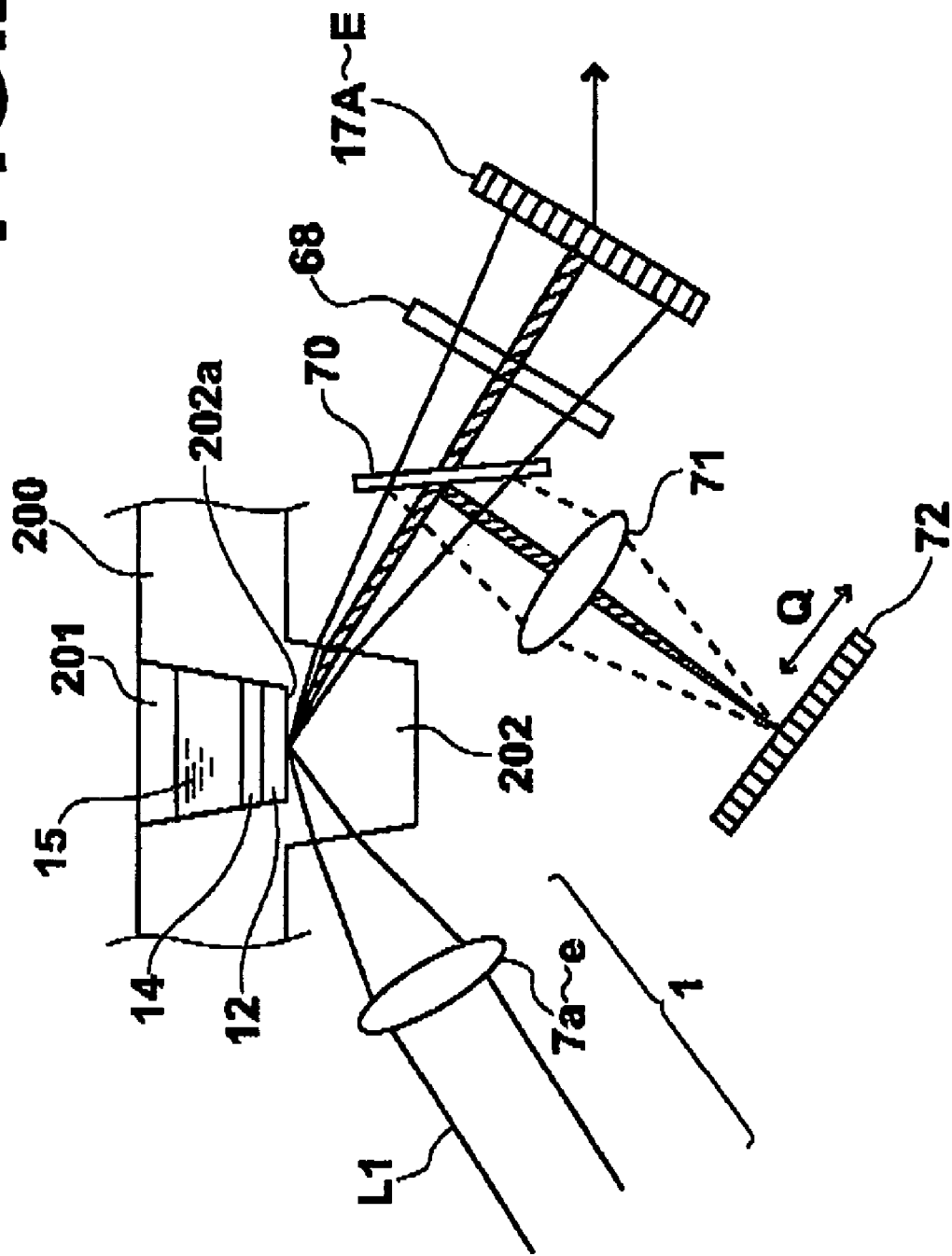
FIG. 23 is a fragmentary side view of a surface plasmon resonance sensor in accordance with a thirteenth embodiment of the present invention.

In this embodiment, the light beam L1 is caused to impinge upon the interface 202a in a p-polarized state and the state of a generated dark line is measured. In the case where the light beam L1 includes a plurality of polarization components, an analyzer 68 is disposed upstream of the photodetector means 17 as shown in FIG. 23, which is a side view showing a thirteenth embodiment of the present invention, so that only a p-polarization component can impinge the photodetector means 17.

Figure 24:
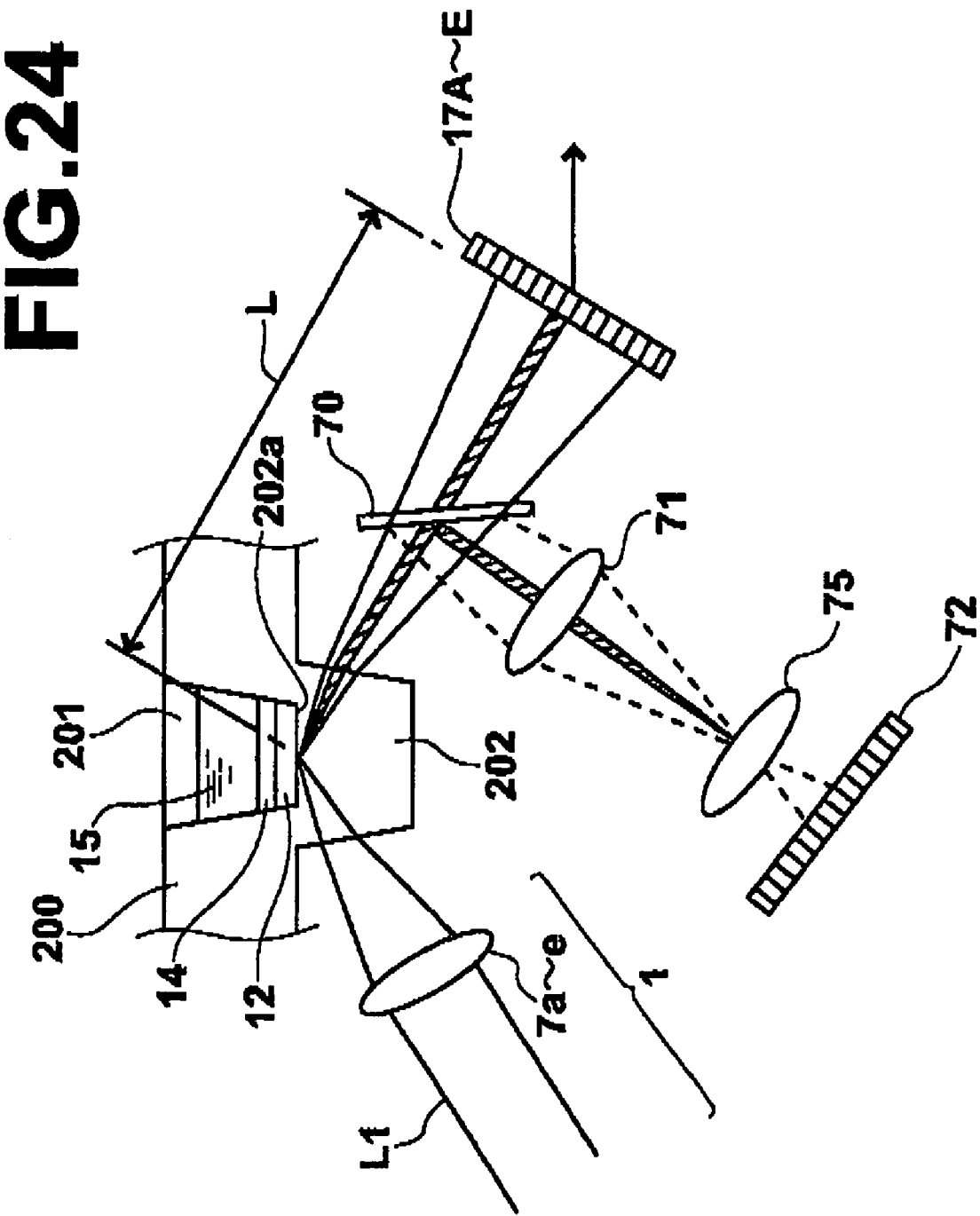
FIG. 24 is a fragmentary side view of a surface plasmon resonance sensor in accordance with a fourteenth embodiment of the present invention.

A measuring apparatus (a surface plasmon resonance sensor) in accordance with a fourteenth embodiment of the present invention will be described with reference to FIGS. 24 and 25, hereinbelow.

Figure 22:
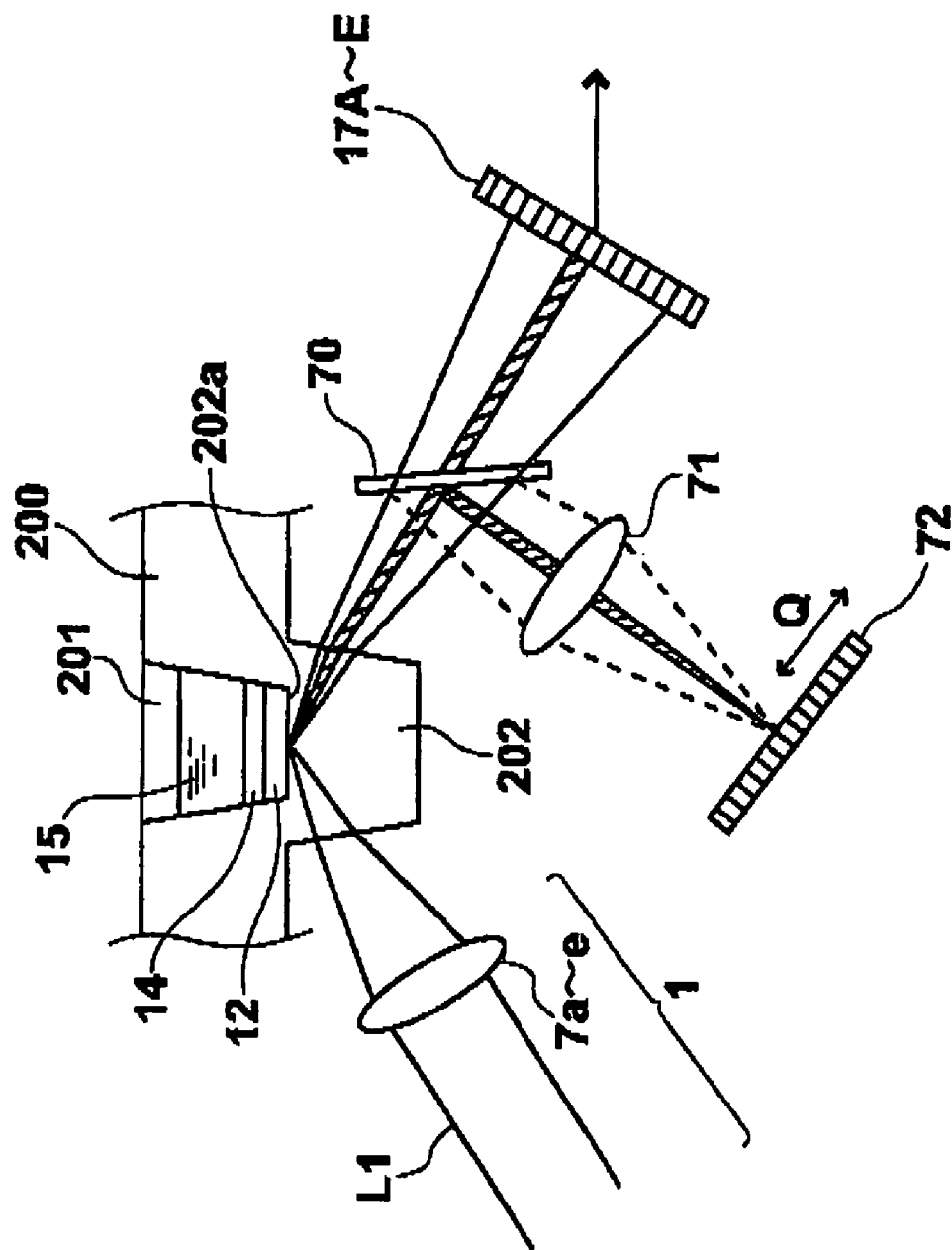
FIG. 22 is a fragmentary side view of a surface plasmon resonance sensor in accordance with a twelfth embodiment of the present invention.

The longitudinal tilt measuring means of the surface plasmon resonance sensor of this embodiment comprises a second lens 75 in addition to the longitudinal tilt measuring means of the measuring apparatus of the twelfth embodiment shown in FIG. 22. The second lens 75 is disposed on the optical path to the second photodetector means 72. In this measuring apparatus, by combining a pair of lenses, not only the longitudinal tilt of the interface 202a but also vertical shift of the interface 202a can be detected, whereby the state of attenuation in total internal reflection can be measured more accurately.

Figure 25A:
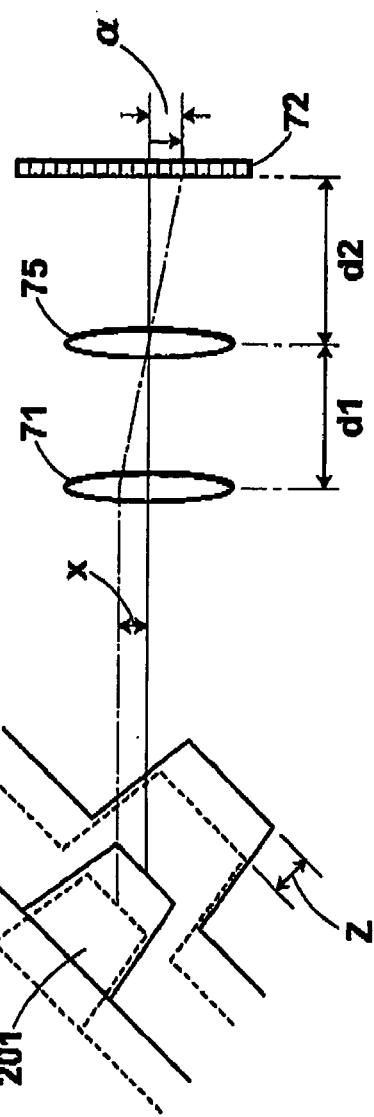
FIGS. 25A and 25B are views for illustrating a tilt measuring means employed in the surface plasmon resonance sensor in accordance with the fourteenth embodiment.
Figure 25B:
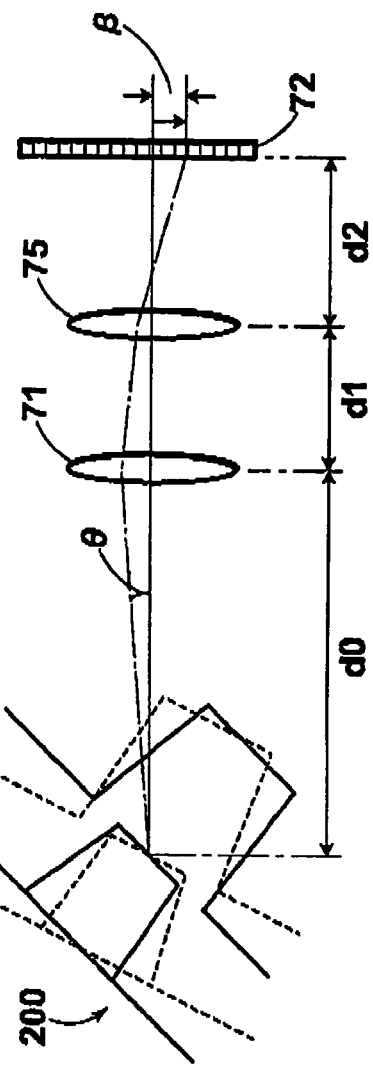

Detection of the longitudinal tilt and the vertical shift of the interface 202a will be described in brief with reference to FIGS. 25A and 25B, hereinbelow. FIG. 25A schematically shows the principle of detecting the shift of the interface 202a and FIG. 25B schematically shows the principle of detecting the longitudinal tilt of the interface 202a. It is assumed that f1 and f2 represent the focal lengths of the converging lens 71 and the second lens 75, L represents the distance between the position at which the light beam is reflected and the photodetector means 17 (FIG. 24), d0 represents the distance between the position at which the light beam is reflected and the converging lens 71, d1 represents the distance between the converging lens 71 and the second lens 75, d2 represents the distance between the second lens 75 and the second photodetector means 72, x represents the shift of the position at which the light beam is reflected based on the movement of the interface in the vertical direction, and θ represents the longitudinal tilt of the interface. Though the optical path is changed by the half-silvered mirror 70 in FIG. 24, the optical path is set to be straight in FIGS. 25A and 25B for the purpose of easiness of understanding.

Assuming that the longitudinal tilt of the interface 202a is θ, and the shift of the position at which the light beam is reflected is x, the shift A of the total attenuation angle is represented by L tan θ+x.

When the measuring plate 200 is shifted by a distance z from the position shown by the solid line to the position shown by the broken line as shown in FIG. 25A, the shift x of the position at which the light beam is reflected appears as a shift a of the light beam receiving position on the second photodetector means 72 by the effect of the lenses 71 and 75. Further, when the measuring plate 200 is inclined by an angle θ from the position shown by the solid line to the position shown by the broken line as shown in FIG. 25B, the light beam receiving position on the second photodetector means 72 shifts by an amount β.

The shift B of the beam spot on the second photodetector means 72 due to the tilt and the vertical shift of the interface 202a is represented by the following formula.

$$\theta\{d1+d2-d1d2/f2-d0(d1/f1+d0/f1-d1d2/f1/f2-1+d2/f2)\}-x(d1/f1+d2/f1-d1d2/f1/f2-1+d2/f2)$$

Accordingly, when L, d0, d1, d2, f1 and f2 are selected and the converging lens 71, the second lens 75, and the second photodetector means 72 are positioned so that A=B or A=−B, the distance by which the total attenuation angle θ is shifted appears as the shift of spot on the second photodetector means 75. For example, when the converging lens 71, the second lens 75 and the second photodetector means 72 are selected and positioned so that d1=f1, d2=f2 and d0=f1+L, A=B or A=−B.

When the longitudinal tilt and the vertical shift of the interfaces 202a are both obtained by the use of a pair of lenses as in this embodiment, a measured value corrected according to the movement of the interface 202a can be obtained, and accordingly, measurement of the state of the attenuation in total internal reflection can be more accurately performed.

Though, in the fifth to fourteenth embodiments, the second light beam projecting means uses a part of a light beam L1 emitted from the laser 2, a light source for the second light beam L2 may be separately provided.

Further, though, in the fifth to fourteenth embodiments, the longitudinal tilt of the interface is compensated for by correcting the measured value according to the measured longitudinal tilt of the interface, the longitudinal tilt of the interface may be compensated for by adjusting the position of the light beam projecting means, the photodetector means, and/or the sensor well unit.

Further, though, in each of the embodiments provided with an operation means for obtaining a measured value corrected according to the tilt of the interface, the position of the interface at the first time measurement is taken as the reference position and the tilt of the interface from the reference position is obtained at the following measurements, the position of the interface at a measurement other than the first time measurement may be taken as the reference position or an average position of the interface in a plurality of times of measurement may be taken as the reference position.

Further, by storing the detecting error peculiar to the measuring apparatus for each measuring apparatus and using data on the detecting error peculiar to the measuring apparatus when measuring the tilt, the measuring accuracy can be further improved.

Further, in each of the embodiments provided with an operation means for obtaining a measured value corrected according to the tilt of the interface, an alarm is may be made when the tilt of the interface exceeds a predetermined threshold value and the position of the light beam projecting means, the photodetector means, and/or the sensor well unit may be adjusted in this case.

Though, in the measuring apparatuses in accordance with the first to fourteenth embodiments, only a tilt of the interface 202a in the longitudinal direction is detected and the measuring error generated due to the longitudinal tilt of the interface 202a is cancelled, there exists a tilt of the interface 202a in the transverse direction which changes the impinging position of the light beam (the position in which the light beam impinges upon the interface 202a) in a direction normal to the longitudinal direction. The transverse tilt of the interface 202a leads to the shift of the light beam L1, reflected in total direction at the interface 202a, in a direction perpendicular to the direction in which the photodiodes are arranged. When the transverse tilt of the interface 202a exceeds a predetermined value, the reflected light beam L1 cannot be received by the photodetector means. In the following embodiments, a longitudinal/transverse tilt measuring means which measures a longitudinal tilt and a transverse tilt of the interface 202a and a longitudinal/transverse direction correction means which corrects the measuring error due to the longitudinal tilt and the transverse tilt of the interface 202a detected by the longitudinal/transverse tilt measuring means.

Figure 26:
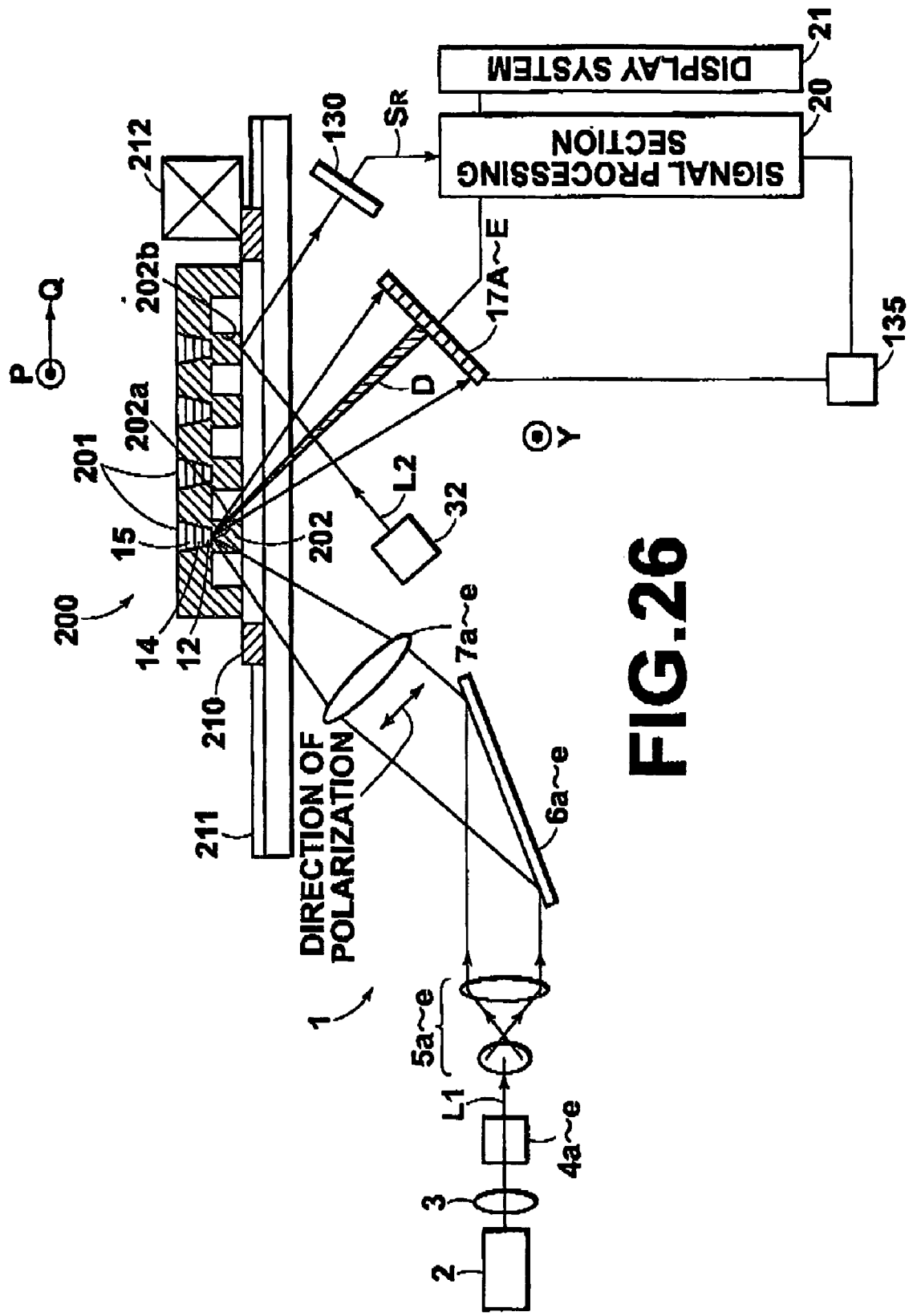
FIG. 26 is a side view of a surface plasmon resonance sensor in accordance with a fifteenth embodiment of the present invention.

A fifteenth embodiment of the present invention will be described with reference to FIG. 26, hereinbelow.

The surface plasmon resonance sensor of this embodiment is substantially the same as the surface plasmon resonance sensor of the first embodiment except that a longitudinal/transverse tilt measuring means and a longitudinal/transverse direction correction means which corrects the measuring error (including a defective measurement) due to the longitudinal tilt and the transverse tilt of the interface 202a detected by the longitudinal/transverse tilt measuring means are provided. The longitudinal/transverse tilt measuring means comprises a second light beam projecting means 32 which causes a second light beam L2 to impinge upon the bottom surface 202b of the light inlet/outlet portion 202 to be reflected in total internal reflection and a second photodetector means 130 which detects the second light beam L2 reflected by the bottom surface 202b of the light inlet/outlet portion 202.

Figure 27:
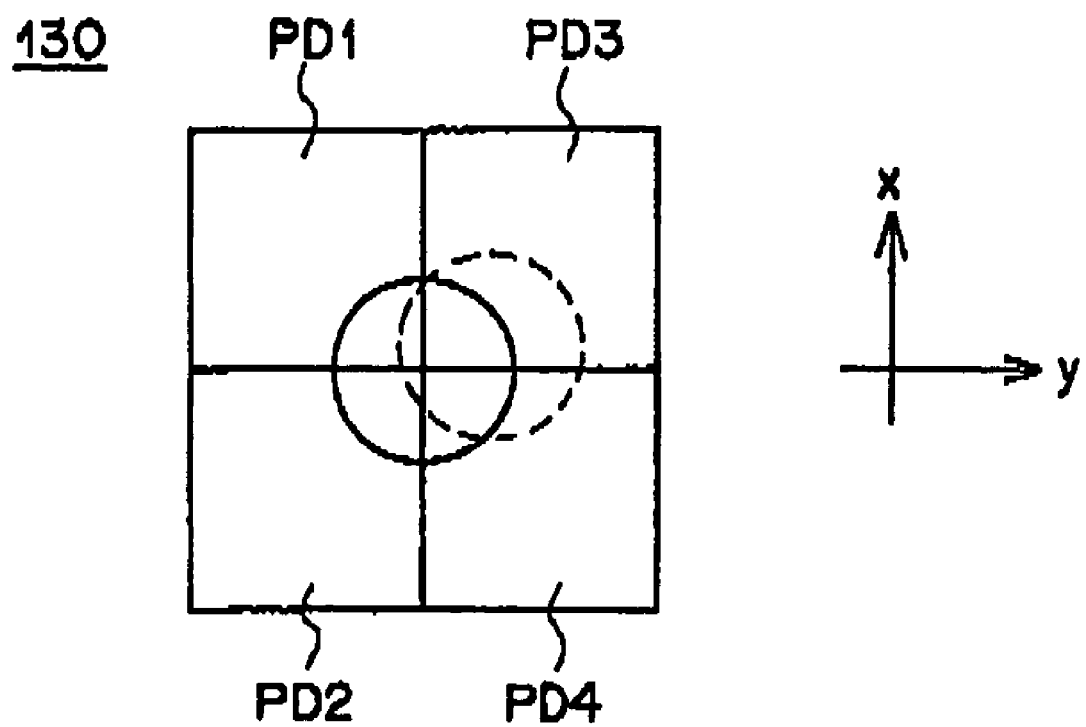
FIG. 27 is a view showing a light receiving face of the second photodetector.

The second photodetector means 130 may be, for instance, a position sensor comprising a four-sectioned photodiode and two-dimensional position fluctuation of the second light beam L2 impinging upon its light receiving surface. FIG. 27 schematically shows the light receiving surface of the second photodetector means 130. As shown in FIG. 27, the second photodetector means 130 comprises four photodiodes PD1, PD2, PD3 and PD4 and the position of spot of the second light beam L2 on the second photodetector means 130 on the basis of the amounts of light the photodiodes receives. For example, shift of the spot of the second light beam L2 in the direction of x due to the longitudinal tilt of the interface 202a can be detected on the basis of the difference between the sum of the signals output from the photodiodes PD1 and PD3 and the sum of the signals output from the photodiodes PD2 and PD4, and shift of the spot of the second light beam L2 in the direction of y due to the transverse tilt of the interface 202a can be detected on the basis of the difference between the sum of the signals output from the photodiodes PD1 and PD2 and the sum of the signals output from the photodiodes PD3 and PD4.

The second light beam L2 used here to measure tilt of the interface impinges upon the interface as s-polarization polarized in a different direction from the first light beam L1.

The longitudinal/transverse direction correction means comprises a position adjustment means (a transverse direction adjustment means) which moves the photodetector means 17 in the transverse direction to compensate for shift of the first light beam receiving position of the photodetector means 17 in the direction of arrow y due to the transverse tilt of the interface 202a, and an operation means which obtains a corrected measured value corrected according to the longitudinal tilt of the interface 202a.

That is, the position adjustment means comprises the photodetector means 17 which is movable in the direction of y and a drive means 135 which moves the photodetector means 17. The drive means 135 adjusts the position in the direction of y of the photodetector means 17 to compensate for shift of the first light beam receiving position of the photodetector means 17 under the control of the signal processing section 20 which receives a signal from the second photodetector means 130 and detects shift of the second light beam L2 in the direction of y. Further, the operation means is formed by the signal processing section 20 and as in the first embodiment, the signal processing section 20 receives a signal from the second photodetector means 130 and obtains shift of the second light L2 in the direction of x. The signal processing section 20 obtains a corrected measured value corrected according to the tilt of the interface 20a by adding a correction signal for compensating for the longitudinal tilt of the interface 202a to a signal from the photodetector means 17. The specific operation is the same as described above in conjunction with the first embodiment, and accordingly will not be described, here.

Measurement of the tilt and adjustment of the position of the photodetector means 17 are carried out as follows. When measurement on one sample 15 is performed first time, the apparatus is set so that the second light beam L2 reflected at the outer bottom surface 202b of the light inlet/outlet portion 202 of the measuring plate 200 is received at the center of the second photodetector means 130 as shown by the solid line in FIG. 27. Upon the second time measurement, the reflected second light beam L2 is detected in the same manner and the shift of the second light beam receiving position in the direction of y representing the transverse tilt of the interface 202a is obtained. Then the photodetector means 17 is moved in the transverse direction to compensate for shift of the first light beam receiving position of the photodetector means 17 in the direction of arrow y. At this time, only the photodetector means 17 may be adjusted in its position but the second photodetector means 130 may be interlocked with the photodetector means 17 to move together therewith so that when the photodetector means 17 has been adjusted in its position, the second photodetector means 130 receives the second light beam L2 at the center of the light receiving face in the direction of y. Then shift of the second light beam L2 in the direction of x due to longitudinal tilt of the interface is detected and the signal processing section 20 corrects the measured value on the basis of the longitudinal tilt of the interface 202a.

Upon the third time measurement and the following time measurements, the state of total internal reflection is measured after the photodetector means 17 is adjusted in its position in the transverse direction according to the position of the second light beam L2 received by the second photodetector means 130 and then a measured value corrected on the basis of the longitudinal tilt of the interface 202a from the position of the interface 202a upon the first time measurement are obtained, whereby a measured value in which the longitudinal and transverse tilts of the interface 202a are compensated for can be obtained and more accurate measurement can be performed.

Figure 28:
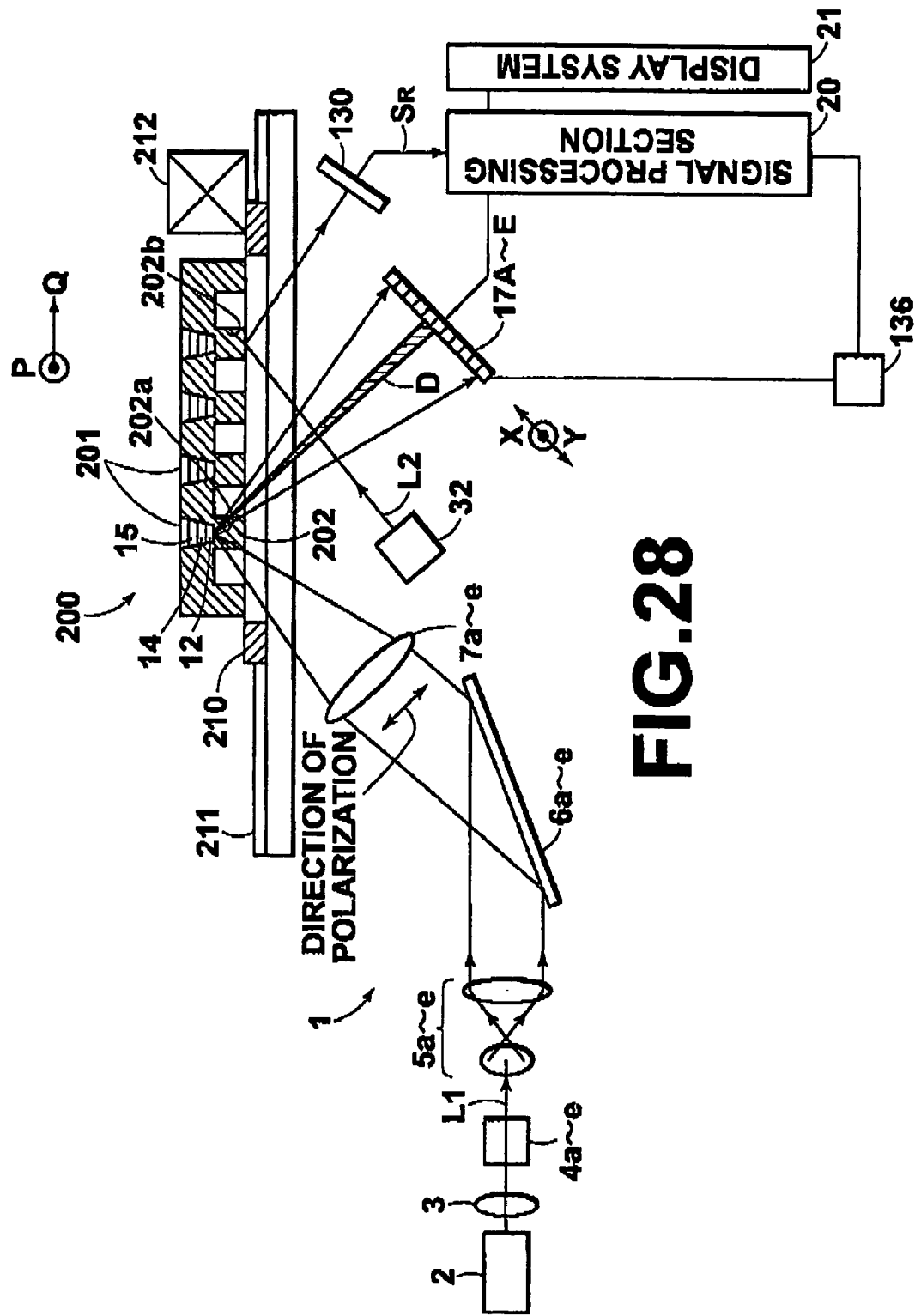
FIG. 28 is a side view of a surface plasmon resonance sensor in accordance with a sixteenth embodiment of the present invention.

A sixteenth embodiment of the present invention will be described with reference to FIG. 28, hereinbelow.

The surface plasmon resonance sensor of this embodiment is substantially the same as the surface plasmon resonance sensor of the fifteenth embodiment except the structure of the longitudinal/transverse direction correction means which corrects the error due to the longitudinal tilt and the transverse tilt of the interface 202a. The longitudinal/transverse direction correction means in this embodiment is for simultaneously compensating for the longitudinal and transverse tilts of the interface 202a and as the longitudinal/transverse direction correction means which corrects the measuring error (including a defective measurement) due to the longitudinal tilt and the transverse tilt of the interface 202a, there is provided a position adjustment means which two-dimensionally moves the photodetector means 17 in the direction of arrow X and the direction of y perpendicular to the plane of the paper. That is, the position adjustment means comprises the photodetector means 17 which is movable in the direction of xy and a drive means 136 which moves the photodetector means 17. The drive means 136 adjusts the position of the photodetector means 17 under the control of the signal processing section 20 which receives a signal from the second photodetector means 130 and detects shift of the second light beam L2.

Measurement of the longitudinal and transverse tilts and adjustment of the position of the photodetector means 17 are carried out as follows. When measurement on one sample 15 is performed first time, the apparatus is set so that the second light beam L2 reflected at the outer bottom surface 202b of the light inlet/outlet portion 202 of the measuring plate 200 is received at the center of the second photodetector means 130 as shown by the solid line in FIG. 27. Upon the second time measurement, the reflected second light beam L2 is detected in the same manner and the shift of the second light beam receiving position from the position of the first detection is obtained. Then the photodetector means 17 is moved in xy direction to compensate for shift of the first light beam receiving position of the photodetector means 17. At this time, only the photodetector means 17 may be adjusted in its position but the second photodetector means 130 may be interlocked with the photodetector means 17 to move together therewith so that when the photodetector means 17 has been adjusted in its position, the second photodetector means 130 receives the second light beam L2 at the center of the light receiving face in the direction of y.

Upon the third time measurement and the following time measurements, the state of total internal reflection is measured after the photodetector means 17 is adjusted in its position according to the position of the second light beam L2 received by the second photodetector means 130, whereby a measured value in which the longitudinal and transverse tilts of the interface 202a are compensated for can be obtained and more accurate measurement can be performed.

Figure 29:
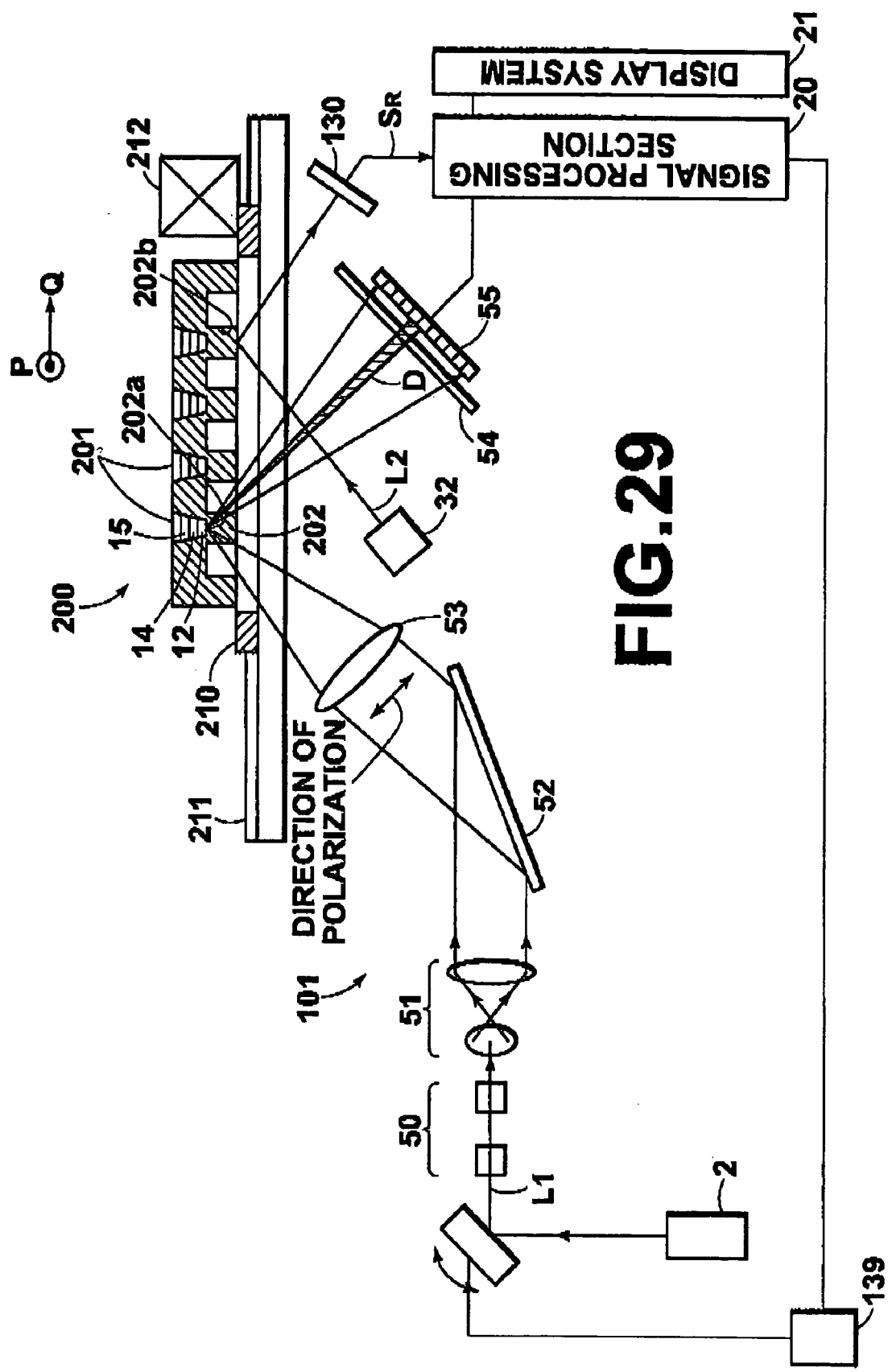
FIG. 29 is a side view of a surface plasmon resonance sensor in accordance with a seventeenth embodiment of the present invention.

A seventeenth embodiment of the present invention will be described with reference to FIG. 29, hereinbelow.

The surface plasmon resonance sensor of this embodiment is provided, as the longitudinal/transverse direction correction means which corrects the measuring error due to the longitudinal tilt and the transverse tilt of the interface 202a, with a light beam adjustment means which adjusts the angle of incidence and the position of incidence of the light beam L1 by the light beam projecting means 101 in place of the position adjustment means which adjusts the position of the photodetector means 17. The light beam adjustment means comprises a tilt mirror 138 having a reflecting surface which reflects the light beam L1 from the laser 2 and is rotatable in both the longitudinal and transverse directions and a mirror drive means 139 which rotates the reflecting surface of the tilt mirror 138. The mirror drive means 139 rotates the reflecting surface of the tilt mirror 138 under the instruction of the signal processing section 20 to adjust the angle of incidence and the position of incidence of the light beam L1.

By adjusting the angle of incidence and the position of incidence of the light beam L1 according to the longitudinal and transverse tilts of the interface 202a measured by the longitudinal/transverse tilt measuring means, result of measurement in which the longitudinal and transverse tilts of the interface 202a is compensated for can be obtained.

In place of adjusting the photodetector means or the light beam projecting means as in the sixteenth and seventeenth embodiments, the longitudinal and transverse tilts of the interface may be compensated for by changing the inclination of the measuring plate 200 itself. Further, the longitudinal and transverse tilts of the interface may be compensated for by adjusting, for instance, the positions of all of the photodetector means, the light beam projecting means and the measuring plate 200 or any two of them.

Figure 30:
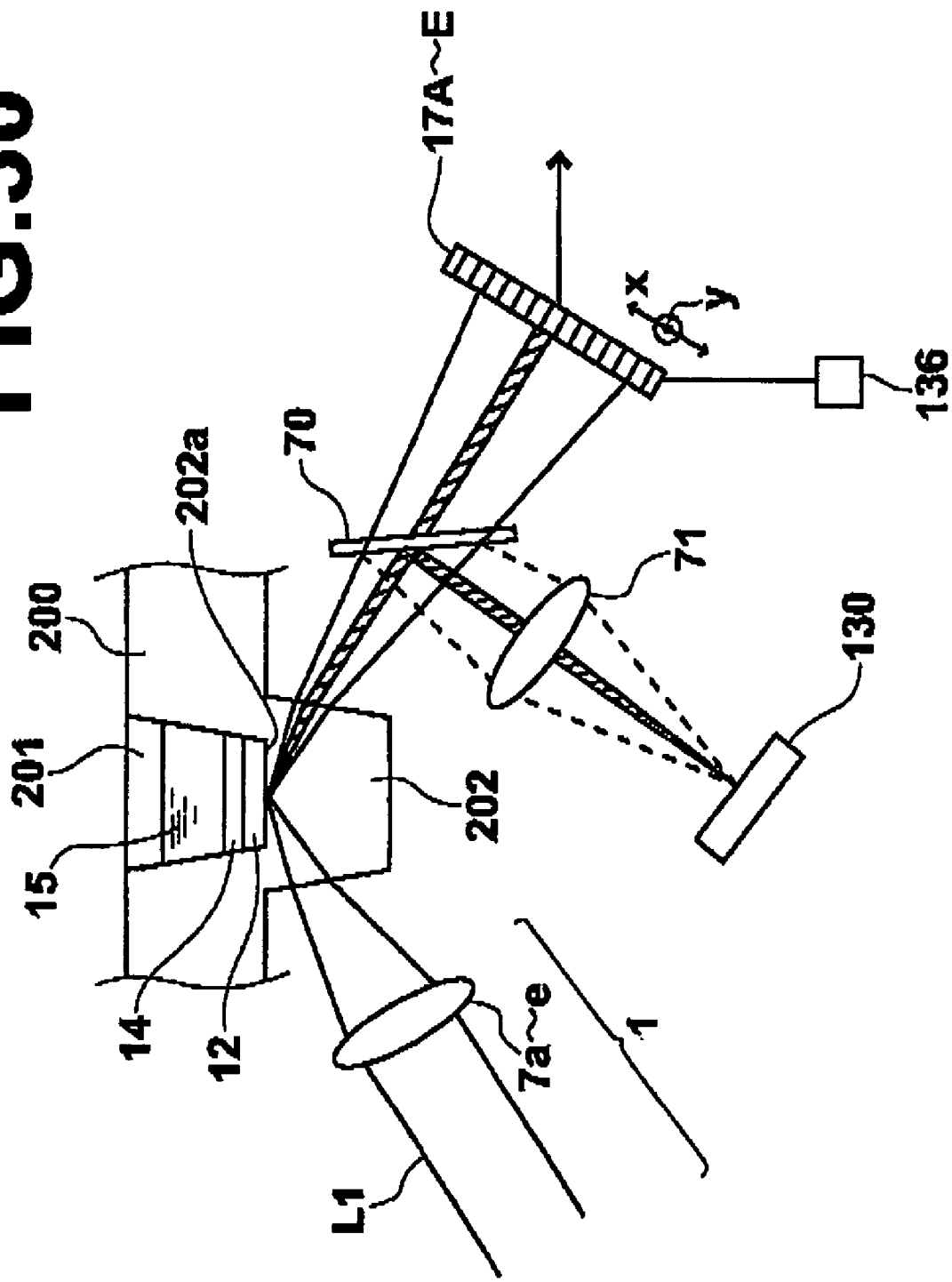
FIG. 30 is a fragmentary side view of a surface plasmon resonance sensor in accordance with an eighteenth embodiment of the present invention.

As shown in the surface plasmon resonance sensor in accordance with an eighteenth embodiment of the present invention shown in FIG. 30, when a two-dimensional sensor 130 such as of a four-sectioned photodiode, a resistance type photodetector, or the like is used in place of the one-dimensional photodiode array of the second photodetector means 72 in the twelfth embodiment (FIG. 22), the photodetector means 17 is movable in xy direction, and a drive means 136 which drives the photodetector means 17 to adjust the position thereof is provided, not only the longitudinal tilt of the interface 202a but also the transverse tilt of the interface 202a can be detected and an accurate measured value, which is corrected according to the longitudinal and transverse tilts of the interface 202a, can be obtained.

A nineteenth embodiment of the present invention will be described with reference to FIGS. 31 to 33, hereinbelow.

Figure 31:
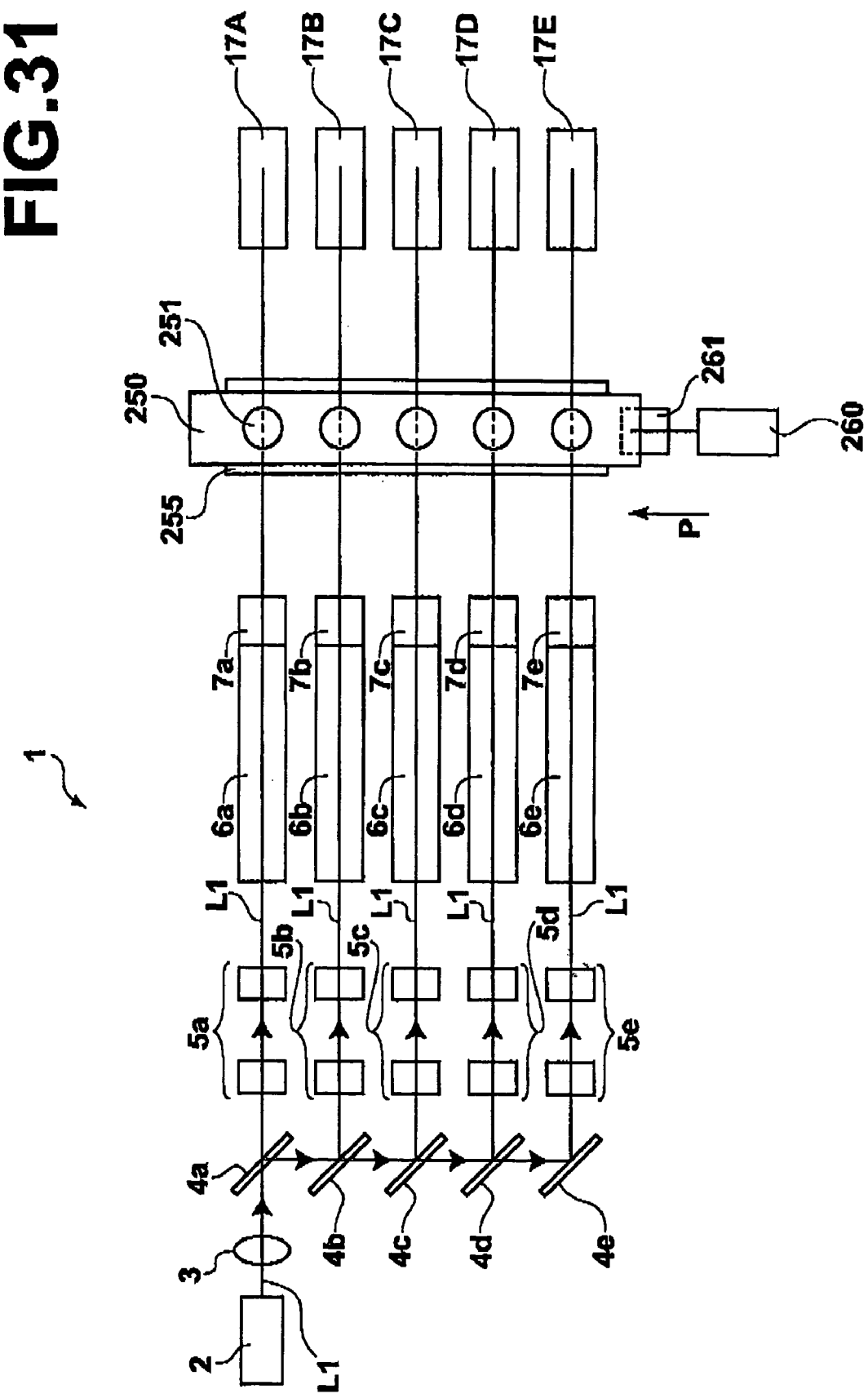
FIG. 31 is a plan view of a surface plasmon resonance sensor in accordance with a nineteenth embodiment of the present invention.
Figure 32:
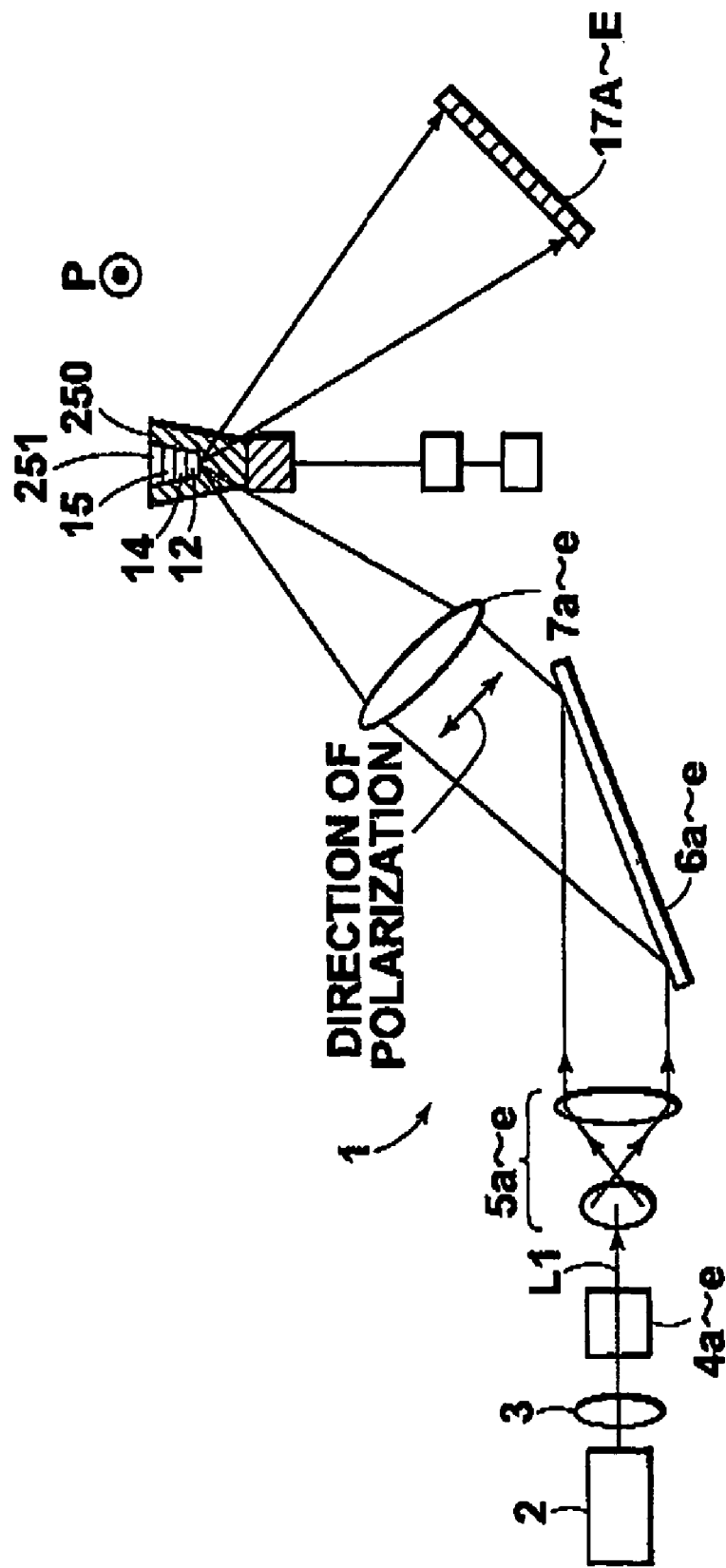
FIG. 32 is a side view of the surface plasmon resonance sensor in accordance with the nineteenth embodiment of the present invention.
Figure 33:
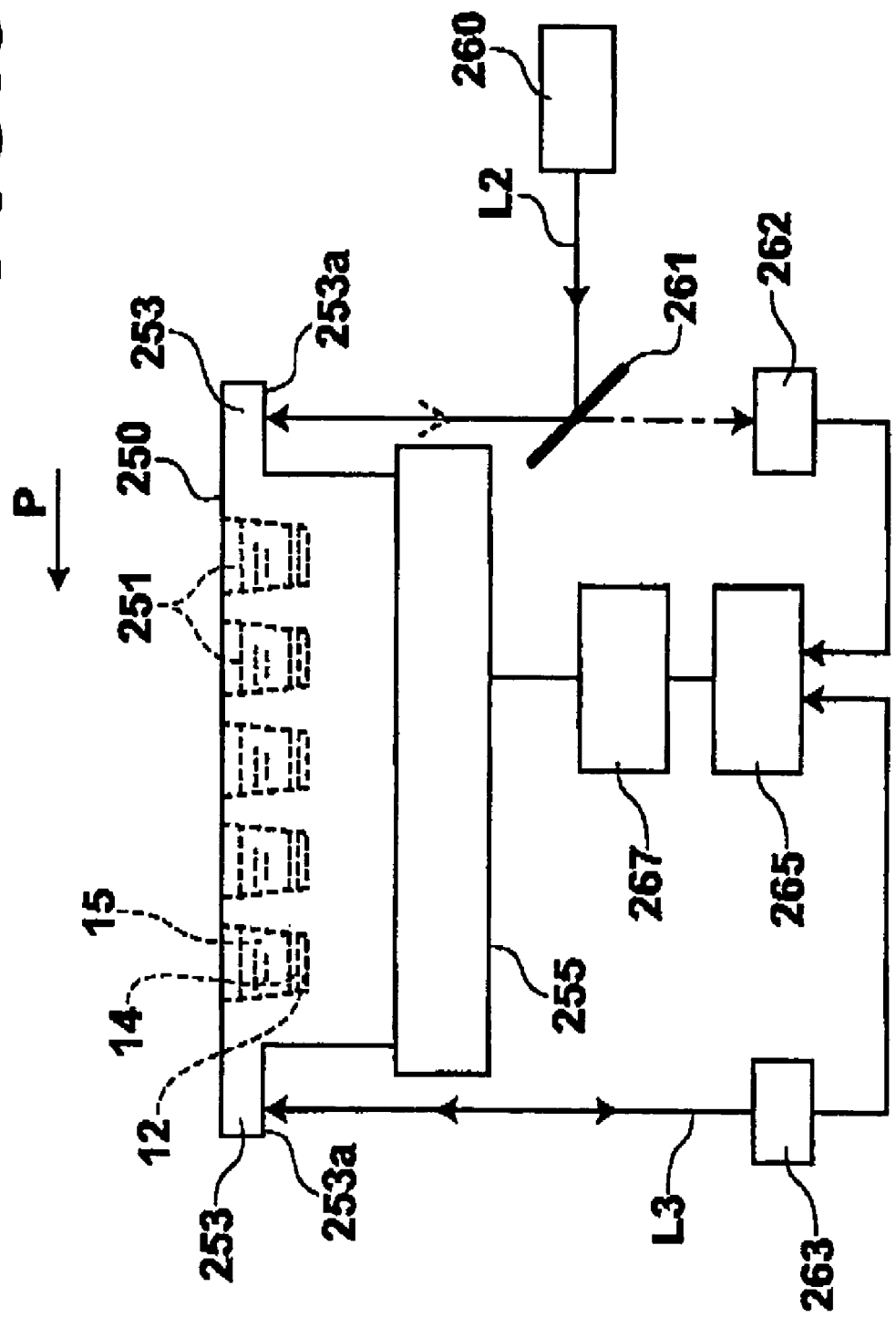
FIG. 33 is another side view of the surface plasmon resonance sensor in accordance with the nineteenth embodiment of the present invention.

FIG. 31 is a plan view of a measuring apparatus in accordance with a nineteenth embodiment of the present invention, and FIGS. 32 and 33 are side views of the same.

The measuring apparatus of this embodiment is provided with a measuring bar 250, having a plurality of one-dimensionally arranged sample wells, in place of aforesaid measuring plate. The measuring plate 250 is placed on a support table 255 upon measurement. The beam projecting means 1 and the photodetector means 17 are of the same structure as those in the first embodiment.

As shown in FIG. 33, the measuring bar 250 is provided with a plurality of (five in this embodiment) one-dimensionally arranged sample wells 251 and is provided with a collar 253 on each end thereof. On the inner bottom surface of each sample well 251, is formed a metal layer 12 and a sensing medium layer 14 is formed on the metal layer 12. The lower surface 253a of each collar 253 is a light reflecting surface.

The shift of the interface of the measuring plate or the measuring bar includes a vertical shift of the position of the same as well as the longitudinal and transverse tilts of the same. This particular embodiment is provided with a vertical position sensor which measures the vertical shift of the interface in addition to the longitudinal/transverse tilt measuring means and is provided with a position adjustment means which adjusts the vertical position of the interface in addition to the longitudinal and transverse tilts of the interface.

The longitudinal/transverse tilt measuring means comprises, as shown in FIG. 33, a second light source 260 which emits a second light beam L2, a half-silvered mirror 261 which reflects the light beam from the second light source 260 toward the lower surface 253a of the collar 253 of the measuring bar 250 and permits the light reflected at the lower surface 253a to pass therethrough, and a second photodetector means in the form of a four-sectioned photodiode 262 which detects the light passing through the half-silvered mirror 261.

The vertical position sensor may be, for instance, an optical distance sensor 263 which emits a third light beam L3 and receives the third light beam L3 reflected at the lower surface 253a of the collar 253, thereby detecting the vertical position of the lower surface 253a of the collar 253.

The position adjustment means which adjusts the vertical position of the interface in addition to the longitudinal and transverse tilts of the interface comprises the support table 255 in the form a motor-drive stage which can incline in the longitudinal direction (φ) and the transverse direction (θ) and can move in the vertical direction, a driver 267 which drives the support table 255, and a servo means 265 which receives signals from the four-sectioned photodiode 262 and the optical distance sensor 263 and outputs a support signal to the driver 267 so that the difference of the signals from the four-sectioned photodiode 262 and the optical distance sensor 263 from reference values becomes not larger than a predetermined value. The "reference values" as used here may be either values when the measuring bar 250 is correctly mounted on the support table 255 or values upon the first time measurement in a plurality of times measurements.

By adjusting the longitudinal and transverse tilts of the lower surface 253a of the collar 253, which is the reference surface, and the vertical shift of the same by the position adjustment means before measurement of the state of attenuation in total internal reflection on each of the sample wells 251 (samples), more accurate measurement can be performed.

Figure 34:
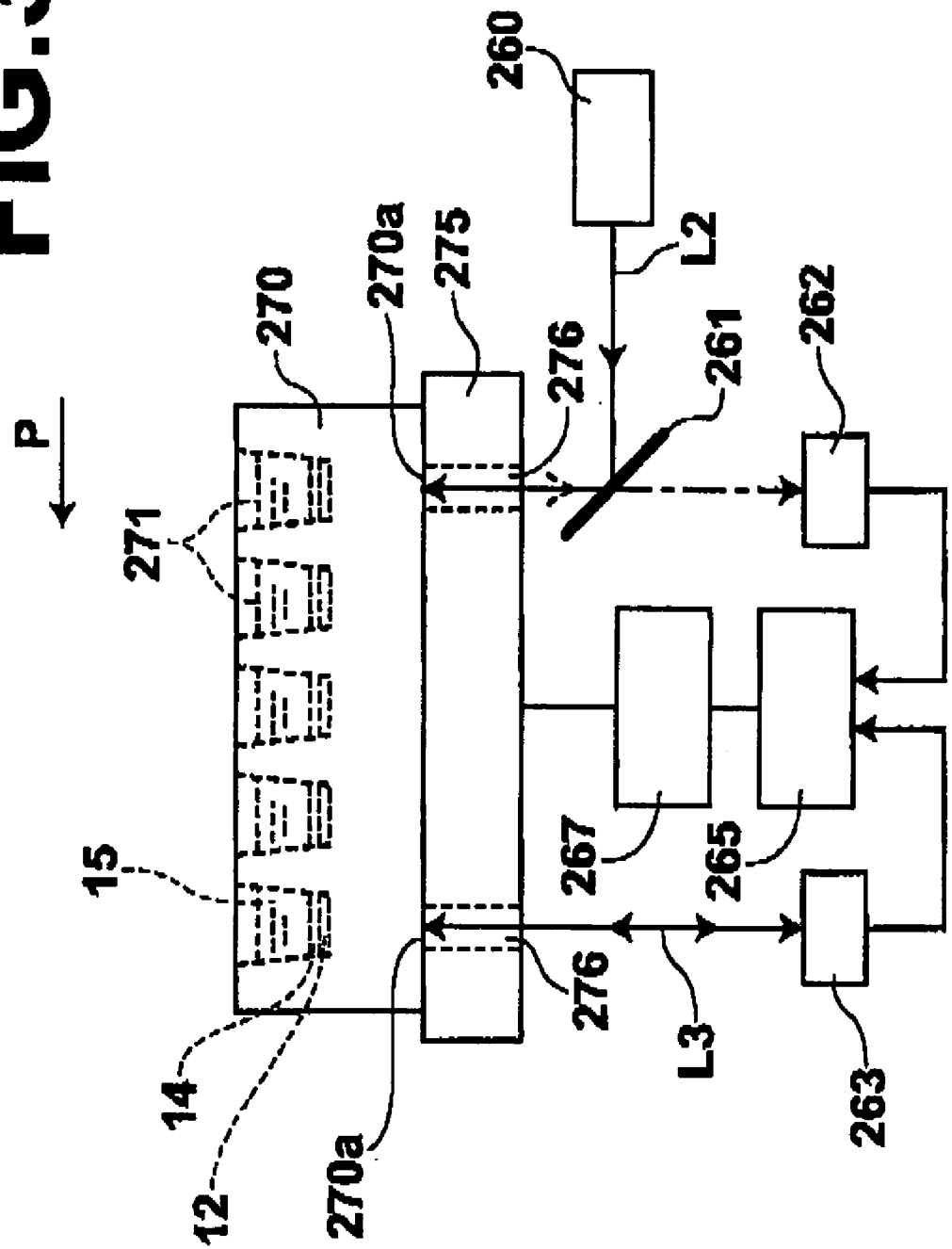
FIG. 34 is a side view of a surface plasmon resonance sensor in accordance with a twentieth embodiment of the present invention.
Figure 35:
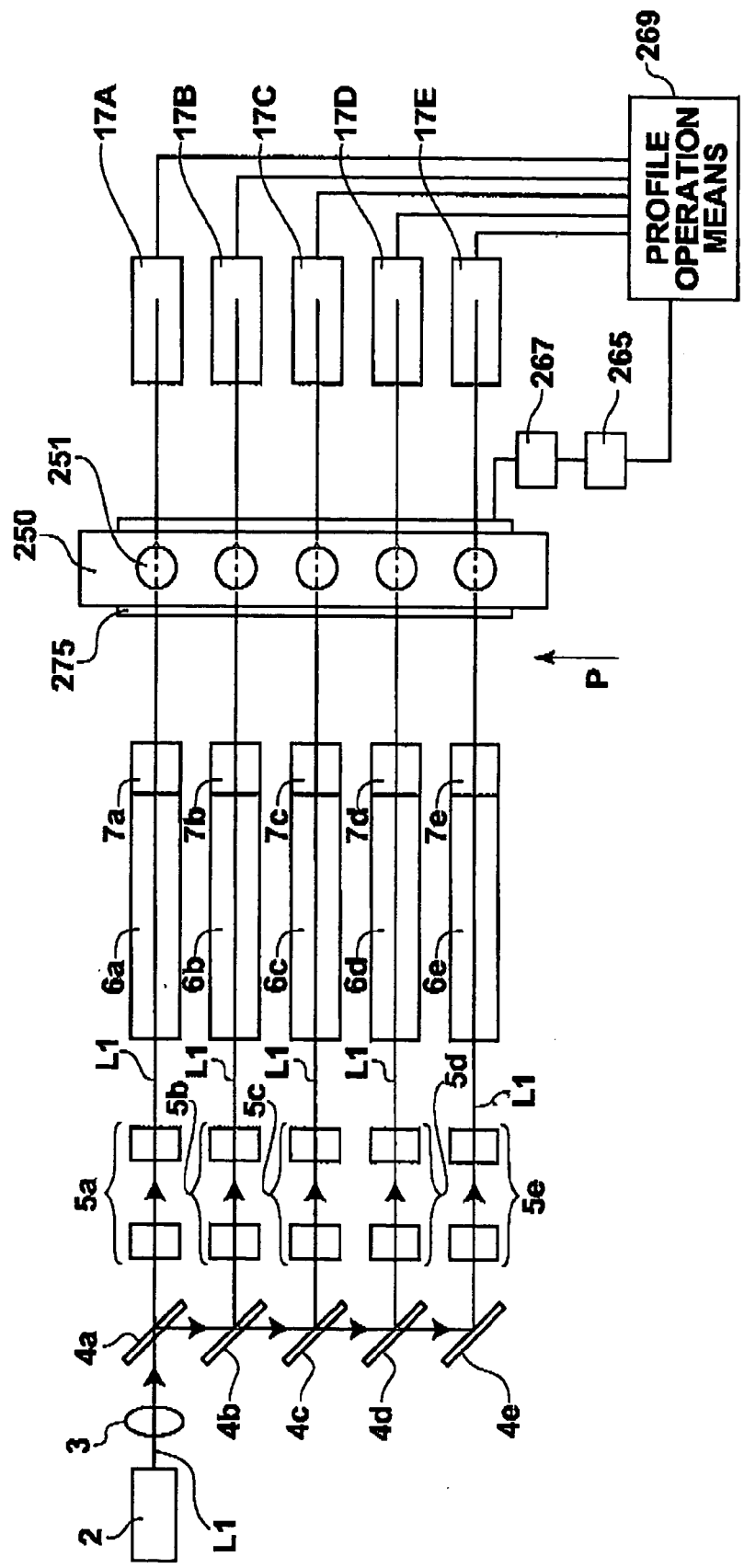
FIG. 35 is a plan view of a surface plasmon resonance sensor in accordance with a twenty-first embodiment of the present invention.

A twentieth embodiment of the present invention will be described with reference to FIG. 34, hereinbelow.

The surface plasmon resonance sensor of this embodiment is substantially the same as the surface plasmon resonance sensor of the nineteenth embodiment except the shapes of the measuring bar and the support table for supporting the measuring bar. That is, the measuring bar 270 in the measuring apparatus of this embodiment is provided with no collar, and the lower surface of the measuring bar is used as the reference surface for measuring the longitudinal and transverse tilts and the vertical position of the measuring bar 270. The second light beam L2 for measuring the tilts and the third light beam L3 for measuring the vertical position are caused to impinge upon the respective reflecting surfaces 270a provided on a part of the lower surface of the measuring bar 270 through openings 276 formed in the support table 275.

A twenty-first embodiment of the present invention will be described with reference to FIG. 34, hereinbelow.

The surface plasmon resonance sensor of this embodiment is substantially the same as the surface plasmon resonance sensor of the nineteenth embodiment except the longitudinal/transverse tilt measuring means. The surface plasmon resonance sensor of this embodiment is provided with a profile operation means 269 which obtains the shift of the interface of the measuring bar on the basis of the profile of the reflected light beam detected by each of the photodetector means 17A to 17E.

The reflected light beam profile for each sample well 251 when the measuring bar 250 is correctly mounted on the support table 275 has been stored in the profile operation means 269 as a reference profile and the profile operation means 269 measures the reflected light beam profile for each sample well 251 when the measuring bar 250 is mounted on the support table 275 and calculates the difference between the measured profile and the reference profile. Then the servo means 265 adjusts the position of the support table 275 so that the difference becomes not larger than a predetermined value. When such a profile operation means 269 is provided, shift and tilts of the interface can be cancelled without providing an additional optical system for detecting tilts and shift of the interface and accurate measurement can be performed.

Though the measuring apparatus in accordance with each of the embodiments is that in which the state of bonding of the sample with the sensing medium is detected on the basis of the state of attenuation in total internal reflection as measured by the angle of incidence at which the light beam impinging upon the interface 202a makes a dark line when the light beam is caused to impinge upon the interface 202a at various angles of incidence, the state of bonding of the sample with the sensing medium may be detected on the basis of the state of attenuation in total internal reflection by the wavelengths by causing light beams of various wavelengths to impinge upon the interface at a predetermined angle of incidence which satisfies the total internal reflection conditions.

A surface plasmon resonance sensor in accordance with a twenty-second embodiment of the present invention where a different reflected light beam is employed will be described, hereinbelow.

Figure 36:
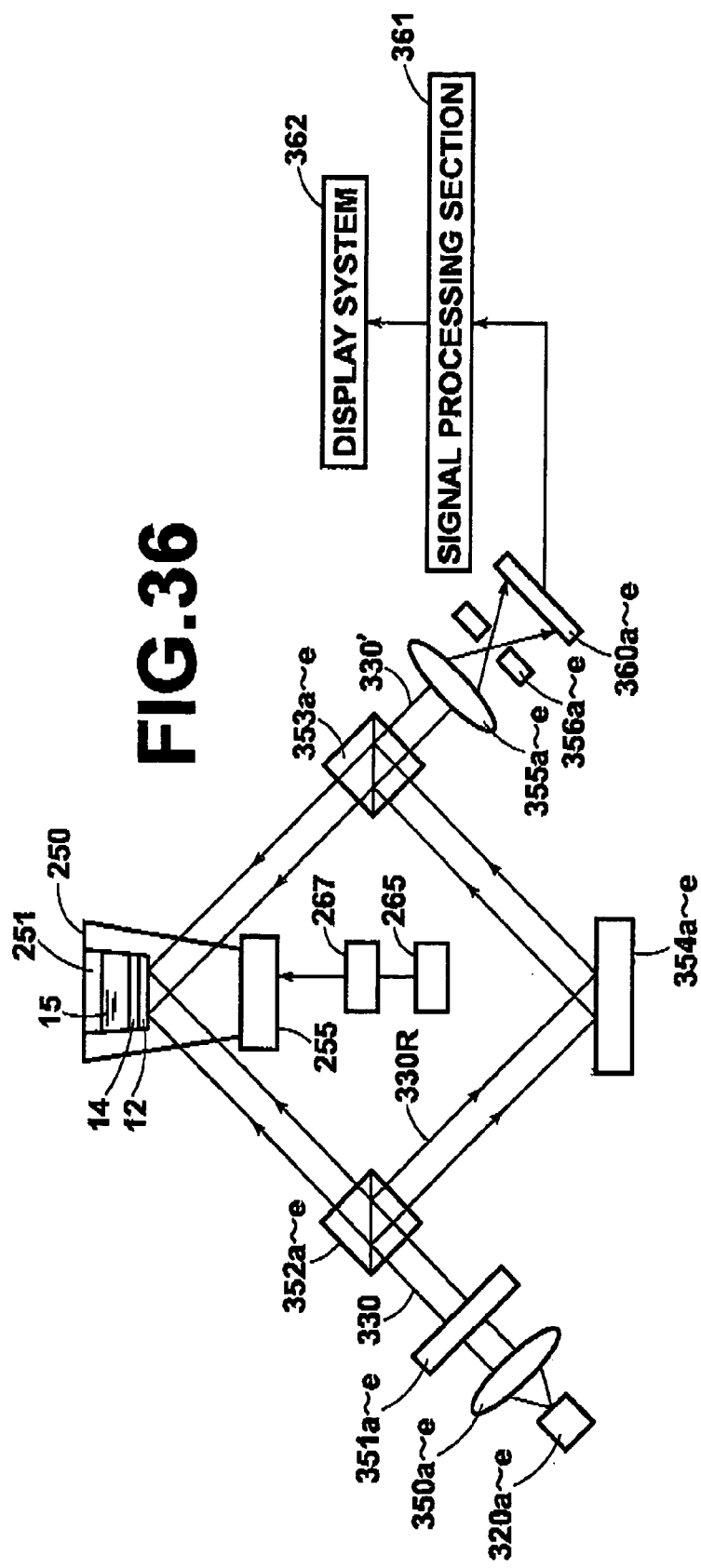
FIG. 36 is a side view of a surface plasmon resonance sensor in accordance with a twenty-second embodiment of the present invention.

As shown in FIG. 36, the surface plasmon resonance sensor of this embodiment has a measuring bar 250, a support table 255, a longitudinal/transverse tilt measuring means, a vertical position measuring means and a position adjustment means which are similar to those in the nineteenth embodiment of the present invention. However, the surface plasmon resonance sensor of this embodiment differs from the surface plasmon resonance sensors of the respective embodiments described above in the method of measuring the state of bonding of the sample with the sensing medium.

Light sources 320a to 320e, and CCDs 360a to 360e are disposed on opposite sides of the measuring bar 250. Collimator lenses 350a to 350e, interference optical systems, condenser lenses 355a to 355e, and apertures 356a to 356e are disposed between the light sources 320a to 320e, and the CCDs 360a to 360e.

The interference optical systems are formed by polarization filters 351a to 351e, half-silvered mirrors 353a to 353e and mirrors 354a to 354e.

The CCDs 360a to 360e are connected to a signal processing section 361 and the signal processing section 361 is connected to a display system 362.

Measurement on samples by the surface plasmon resonance senor of this embodiment will be described, hereinbelow.

The light sources 320a to 320e are operated and light beams 330 (330a to 330e) are emitted therefrom as divergent light beams. The light beams 330a to 330e are collimated respectively by the collimator lenses 350a to 350e and impinge upon the polarization filters 351a to 351e. The light beams 330a to 330e polarized by the polarization filters 351a to 351e to impinge upon the interfaces 202a in a p-polarized state are split into two light beams each by the half-silvered mirrors 352a to 352e. One of the two light beams is reflected by the corresponding one of the half-silvered mirrors 352a to 352e and forms a reference light beam 330R, whereas the other light beam 330S passes through the corresponding one of the half-silvered mirrors 352a to 352e and impinges upon corresponding one of the interfaces 202a. Each of the light beams 330S reflected in total internal reflection at the interface 202a and each of the reference light beams 330R reflected at mirrors 354a to 354e impinge upon corresponding one of the half-silvered mirrors 354a to 354e and synthesized into a light beam 330'. The synthesized light beam 330' is condensed by corresponding one of the condenser lenses 355a to 355e, and impinges the corresponding one of the CCDs 360a to 360e through the corresponding one of the apertures 356a to 356e. The light beam 330' detected by the corresponding one of the CCDs 360a to 360e generates interference fringes according to the state of interference of the light beam 330S and the reference light beam 330R.

By continuously measuring a plurality of times after the sample 15 is dispensed to detect the change of the interference fringes, bonding of the particular material with the sensing medium 14 can be detected. That is, since the refractive index of the sensing medium 14 changes with the state of bonding of the particular material with the sensing medium 14 and the state of the interference fringes generated by interference of the light beam 330S reflected in total internal reflection at the interface 202a and the reference light beam 330R synthesized by corresponding one of the half-silvered mirrors 353a to 353e changes with the refractive index of the sensing medium 14, bonding of the particular material with the sensing medium 14 can be detected by detecting the change of the interference fringes.

The signal processing section 361 detects bonding of the particular material with the sensing medium 14 on the basis of the above principle, and the display system 362 displays the result of the detection.

What is claimed is:

1. A measuring apparatus utilizing the phenomenon of attenuation in total internal reflection comprising
   a sensor well unit having a plurality of one-dimensionally or two-dimensionally arranged sample wells, which are formed in a dielectric block to open in a flat upper surface of the dielectric block, and a thin film layer provided on the inner bottom surface of each sample well,
   a light beam projecting means which causes a plurality of light beams to enter the dielectric block in parallel to impinge upon the interfaces of the inner bottom surfaces of the one-dimensionally arranged sample wells out of the plurality of one-dimensionally or two-dimensionally arranged sample wells and the thin film layers thereon at various angles of incidence so that total internal reflection conditions are satisfied at each of the interfaces, and
   a photodetector means which is provided with a plurality of photodetector elements each positioned in correspondence to one of the interfaces to receive the light beam reflected at the interface, wherein the improvement comprises
   a longitudinal tilt measuring means which measures a longitudinal tilt of the interface from a predetermined reference position changing the angle of incidence of the light beam to the interface, and
   an operation means which obtains a corrected measured value corrected according to the longitudinal tilt measured by the longitudinal tilt measuring means.

2. A measuring apparatus as defined in claim 1 in which the thin film layer is of metal film.

3. A measuring apparatus as defined in claim 1 in which the thin film layer comprises a clad layer and an optical waveguide layer which is formed on the clad layer.

4. A measuring apparatus as defined in claim 1 in which the light beam comprises a single light beam which includes components impinging upon the interface at various angles and has a predetermined intensity distribution in a direction in which the angle of incidence to the interface changes, and the longitudinal tilt measuring means is a means for measuring the longitudinal tilt on the basis of reflection of the light beam at a part of the sensor well unit.

5. A measuring apparatus as defined in claim 4 in which the longitudinal tilt measuring means measures the longitudinal tilt by the use of a component of the light beam outside the attenuation measuring range.

6. A measuring apparatus as defined in claim 5 in which the longitudinal tilt measuring means measures the longitudinal tilt on the basis of the relation between the intensity and the detecting position of a part of the components of the light beam detected by the photodetector means outside the attenuation measuring range, in which part the amount of light largely changes with change of the angle of incidence.

7. A measuring apparatus as defined in claim 5 in which a part of the components of the light beam outside the attenuation measuring range is cause to impinge upon the interface as a dark line and the position of the dark line included in the reflected components of the light beam is detected by the photodetector means.

8. A measuring apparatus as defined in claim 5 in which the longitudinal tilt measuring means comprises a converging lens which converges at least a part of the light beam reflected at a part of the sensor well unit, and a second photodetector means which receives the light beam converged by the converging lens and detects the position of the light beam.

9. A measuring apparatus as defined in claim 8 in which the converging lens is movable between a position on the optical path of the light beam and a position away from the optical path of the light beam, and the photodetector means doubles as the second photodetector means.

10. A measuring apparatus as defined in claim 8 in which the light beam contains differently polarized components, and the second photodetector means receives only the components other than a predetermined polarization component to detect the position of the light beam.

11. A measuring apparatus as defined in claim 8 in which the longitudinal tilt measuring means further comprises a second lens which is disposed between the converging lens and the second photodetector means in a position where the relation between the shift of the total attenuation angle A ($=L \tan \theta + x$) and the shift of the beam spot on the second photodetector means B ($=\theta\{d1+d2-d1d2/f2-d0(d1/f1+d0/f1-d1d2/f1/f2-1+d2/f2)\}-x(d1/f1+d2/f1-d1d2/f1/f2-1+d2/f2)$) is A=B or A=−B, wherein f1 and f2 represent the focal lengths of the converging lens and the second lens, L represents the distance between the position at which the light beam is reflected and the photodetector means, d0 represents the distance between the position at which the light beam is reflected and the converging lens, d1 represents the distance between the converging lens and the second lens, d2 represents the distance between the second lens and the second photodetector means, x represents the shift of the position at which the light beam is reflected based on the movement of the interface in the vertical direction, and θ represents the longitudinal tilt of the interface.

12. A measuring apparatus as defined in claim 11 in which the converging lens, the second lens and the second photodetector means are positioned so that d1−f1, d2=f2 and d0=f1+L.

13. A measuring apparatus as defined in claim 1 in which the longitudinal tilt measuring means comprises a second light beam projecting means which causes a second light beam different from said light beam to impinge upon a part of the sensor well unit and a second photodetector means receives the second light beam reflected at the part of the sensor well unit to detect the position of the second light beam.

14. A measuring apparatus utilizing light reflected in total internal reflection comprising
   a sensor well unit having a plurality of one-dimensionally or two-dimensionally arranged sample wells, which are formed in a dielectric block to open in a flat upper surface of the dielectric block, and a thin film layer provided on the inner bottom surface of each sample well,
   a light beam projecting means which causes a plurality of light beams to enter the dielectric block in parallel to impinge upon the interfaces of the inner bottom surfaces of the one-dimensionally arranged sample wells out of the plurality of one-dimensionally or two-dimensionally arranged sample wells and the thin film layers thereon at an angle of incidence where total internal reflection conditions are satisfied at each of the interfaces, and
   a photodetector means which is provided with a plurality of photodetector elements each positioned in correspondence to one of the interfaces to receive the light beam reflected at the interface, wherein the improvement comprises
   a longitudinal tilt measuring means which measures a longitudinal tilt of the interface from a predetermined reference position changing the angle of incidence of the light beam to the interface, and
   a longitudinal direction adjustment means which adjusts the sensor well unit, the light beam projecting means and the photodetector means according to the longitudinal tilt measured by the longitudinal tilt measuring means to compensate for the longitudinal tilt.

15. A measuring apparatus as defined in claim 14 in which the thin film layer is of metal film.

16. A measuring apparatus as defined in claim 14 in which the thin film layer comprises a clad layer and an optical waveguide layer which is formed on the clad layer.

17. A measuring apparatus as defined in claim 14 in which the light beam comprises a single light beam which includes components impinging upon the interface at various angles and has a predetermined intensity distribution in a direction in which the angle of incidence to the interface changes, and the longitudinal tilt measuring means is a means for measuring the longitudinal tilt on the basis of reflection of the light beam at a part of the sensor well unit.

18. A measuring apparatus as defined in claim 17 in which the longitudinal tilt measuring means measures the longitudinal tilt by the use of a component of the light beam outside the attenuation measuring range.

19. A measuring apparatus as defined in claim 18 in which the longitudinal tilt measuring means measures the longitudinal tilt on the basis of the relation between the intensity and the detecting position of a part of the components of the light beam detected by the photodetector means outside the attenuation measuring range, in which part the amount of light largely changes with change of the angle of incidence.

20. A measuring apparatus as defined in claim 18 in which a part of the components or the light beam outside the attenuation measuring range is cause to impinge upon the interface as a dark line and the position of the dark line included in the reflected components of the light beam is detected by the photodetector means.

21. A measuring apparatus as defined in claim 18 in which the longitudinal tilt measuring means comprises a converging lens which converges at least a part of the light beam reflected at a part of the sensor well unit, and a second photodetector means which receives the light beam converged by the converging lens and detects the position of the light beam.

22. A measuring apparatus as defined in claim 21 in which the converging lens is movable between a position on the optical path of the light beam and a position away from the optical path of the light beam, and the photodetector means doubles as the second photodetector means.

23. A measuring apparatus as defined in claim 21 in which the light beam contains differently polarized components, and the second photodetector means receives only the components other than a predetermined polarization component to detect the position of the light beam.

24. A measuring apparatus as defined in claim 21 in which the longitudinal tilt measuring means further comprises a second lens which is disposed between the converging lens and the second photodetector means in a position where the relation between the shift of the total attenuation angle A (=L tan θ+x) and the shift of the beam spot on the second photodetector means B (=θ{d1+d2−d1d2/f2−d0(d1/f1+d0/f1−d1d2/f1/f2−1+d2/f2)}−x(d1/f1+d2/f1−d1d2/f1/f2−1+d2/f2) is A=B or A=−B, wherein f1 and f2 represent the focal lengths of the converging lens and the second lens, L represents the distance between the position at which the light beam is reflected and the photodetector means, d0 represents the distance between the position at which the light beam is reflected and the converging lens, d1 represents the distance between the converging lens and the second lens, d2 represents the distance between the second lens and the second photodetector means, x represents the shift of the position at which the light beam is reflected based on the movement of the interface in the vertical direction, and θ represents the longitudinal tilt of the interface.

25. A measuring apparatus as defined in claim 24 in which the converging lens, the second lens and the second photodetector means are positioned so that d1=f1, d2=f2 and d0=f1+L.

26. A measuring apparatus as defined in claim 14 in which the longitudinal tilt measuring means comprises a second light beam projecting means which causes a second light beam different from said light beam to impinge upon a part of the sensor well unit and a second photodetector means receives the second light beam reflected at the part of the sensor well unit to detect the position of the second light beam.

27. A measuring apparatus utilizing the phenomenon of attenuation in total internal reflection comprising
   a sensor well unit having a plurality of one-dimensionally or two-dimensionally arranged sample wells, which are formed in a dielectric block to open in a flat upper surface of the dielectric block, and a thin film layer provided on the inner bottom surface of each sample well,
   a light beam projecting means which causes a plurality of light beams to enter the dielectric block in parallel to impinge upon the interfaces of the inner bottom surfaces of the one-dimensionally arranged sample wells out of the plurality of one-dimensionally or two-dimensionally arranged sample wells and the thin film layers thereon at various angles of incidence so that total internal reflection conditions are satisfied at each of the interfaces, and
   a photodetector means which is provided with a plurality of photodetector elements each positioned in correspondence to one of the interfaces to receive the light beam reflected at the interface, wherein the improvement comprises a longitudinal/transverse tilt measuring means which measures a longitudinal tilt of the interface from a predetermined reference position changing the angle of incidence of the light beam to the interface and a transverse tilt of the interface from the predetermined reference position, a transverse direction adjustment means which adjusts the sensor well unit, the light beam projecting means and/or the photodetector means according to the transverse tilt measured by the longitudinal/transverse tilt measuring means to compensate for shift of the light receiving position of the photodetector means due to the transverse tilt, and an operation means which obtains a corrected measured value corrected according to the longitudinal tilt measured by the longitudinal/transverse tilt measuring means.

28. A measuring apparatus as defined in claim 27 in which the thin film layer is of metal film.

29. A measuring apparatus as defined in claim 27 in which the thin film layer comprises a clad layer and an optical waveguide layer which is formed on the clad layer.

30. A measuring apparatus utilizing light reflected in total internal reflection comprising a sensor well unit having a plurality of one-dimensionally or two-dimensionally arranged sample wells, which are formed in a dielectric block to open in a flat upper surface of the dielectric block, and a thin film layer provided on the inner bottom surface of each sample well, a light beam projecting means which causes a plurality of light beams to enter the dielectric block in parallel to impinge upon the interfaces of the inner bottom surfaces of the one-dimensionally arranged sample wells out of the plurality of one-dimensionally or two-dimensionally arranged sample wells and the thin film layers thereon at an angle of incidence where total internal reflection conditions are satisfied at each of the interfaces, and a photodetector means which is provided with a plurality of photodetector elements each positioned in correspondence to one of the interfaces to receive the light beam reflected at the interface, wherein the improvement comprises a longitudinal/transverse tilt measuring means which measures a longitudinal tilt of the interface from a predetermined reference position changing the angle of incidence of the light beam to the interface and a transverse tilt of the interface from the predetermined reference position, and a longitudinal/transverse direction adjustment means which adjusts the sensor well unit, the light beam projecting means and/or the photodetector means according to the longitudinal tilt and the transverse tilt measured by the longitudinal/transverse tilt measuring means to compensate for the longitudinal tilt and to compensate for shift of the light receiving position of the photodetector means due to the transverse tilt.

31. A measuring apparatus as defined in claim 30 in which the thin film layer is of metal film.

32. A measuring apparatus as defined in claim 30 in which the thin film layer comprises a clad layer and an optical waveguide layer which is formed on the clad layer.

* * * * *